US008529912B2

(12) United States Patent
Adderson et al.

(10) Patent No.: US 8,529,912 B2
(45) Date of Patent: Sep. 10, 2013

(54) **GROUP B *STREPTOCOCCUS* POLYPEPTIDES, NUCLEIC ACIDS AND THERAPEUTIC COMPOSITIONS AND VACCINES THEREOF**

(75) Inventors: Elizabeth Adderson, Memphis, TN (US); John Bohnsack, Salt Lake City, UT (US)

(73) Assignees: St. Jude Children's Reseach Hospital, Memphis, TN (US); University of Utah Research Foundation, Salt Lake City, UT (US)

(*) Notice: Subject to any disclaimer, the term of this patent is extended or adjusted under 35 U.S.C. 154(b) by 244 days.

(21) Appl. No.: 13/030,660

(22) Filed: Feb. 18, 2011

(65) Prior Publication Data

US 2013/0129737 A1 May 23, 2013

Related U.S. Application Data

(60) Division of application No. 12/632,269, filed on Dec. 7, 2009, now Pat. No. 7,892,552, which is a division of application No. 11/493,705, filed on Jul. 26, 2006, now Pat. No. 7,645,577, which is a continuation of application No. 10/333,002, filed as application No. PCT/US01/24795 on Aug. 8, 2001, now Pat. No. 7,128,919, which is a continuation of application No. 09/634,341, filed on Aug. 8, 2000, now abandoned.

(51) Int. Cl.
*C07K 14/315* (2006.01)

(52) U.S. Cl.
USPC .................. 424/244.1; 424/185.1; 424/190.1; 424/193.1; 424/203.1; 530/350

(58) Field of Classification Search
None
See application file for complete search history.

(56) References Cited

FOREIGN PATENT DOCUMENTS

| | | |
|---|---|---|
| WO | WO 98/38312 | 3/1998 |
| WO | WO 98/50554 | 11/1998 |
| WO | WO 00/06736 | 2/2000 |
| WO | WO 00/06737 | 2/2000 |
| WO | WO 00/12132 | 9/2000 |
| WO | WO 00/62804 | 10/2000 |
| WO | WO 00/78787 A1 | 12/2000 |

OTHER PUBLICATIONS

Manganelli et al., "Characterization of *emb*, a Gene Encoding the Major Adhesin of *Streptococcus defectivus*," Infection and Immunity 1999 67(1):50-56.

Ozeri et al., "A two-domain mechanism for groupA streptococcal adherence through protein F to the extracellular matrix," The EMBO Journal 1996 15(5):989-998.

Patti J.M., "MSCRAMM-Mediated Adherence of Microorganisms to Host Tissues," Annu. Rev. Microbiol. 1994 58-585-617 XP-001037269.

Patti et al., "Critical Residues in the Ligand-binding Site of the *Staphylococcus aureus* Collagen-binding Adhesion (MSCRAMM)," J. Biol. Chem. 1995 270(20):12005-12011.

Rich et al., "Ace Is a Collagen-binding MSCRAMM from *Enterococcus faecalis*," J. Biol. Chem. 1999 274(38):26939-26945.

Spellerberg et al., "Lmb, a Protein with Similarities to the LraI Adhesin family, Mediates Attachment of *Streptococcus agalactiae* to Human Laminin," Infection and Immunity, Feb. 1999, 67(2):871-878.

NCBI Genbank Accession No. NP_687665 [gi:22536814] Aug. 29, 2002-Jan. 17, 2006 with Revision History.

Maione et al., "Identification of a Universal Group B *Streptococcus* Vaccine by Multiple Genome Screen," Science 2005 309:148-150 and Supporting Online Material.

Greenspan et al (Nature Biotechnology 7: 936-937, 1999).

Chothia et al (The EMBO Journal, 1986, 5/4:823-26).

*Primary Examiner* — Jennifer Graser
(74) *Attorney, Agent, or Firm* — Licata & Tyrrell P.C.

(57) ABSTRACT

This invention provides an isolated nucleic acid encoding a polypeptide comprising amino acid sequences of a streptococcal matrix adhesion E (EmaE) polypeptide. Antibodies to the EmaE polypeptide and immunogenic fragments thereof are also provided. This invention provides pharmaceutical compositions, immunogenic compositions, vaccines, and diagnostic and therapeutic methods of use of the isolated polypeptide, antibodies thereto, and nucleic acids.

10 Claims, 10 Drawing Sheets

EmaA

```
atg acc ctt gtt aaa aat caa gat gct ctt gat aaa gct act gca aat
Met Thr Leu Val Lys Asn Gln Asp Ala Leu Asp Lys Ala Thr Ala Asn
1               5                   10                  15

aca gat gat gcg gca ttt ttg gaa att cca gtt gca tca act att aat
Thr Asp Asp Ala Ala Phe Leu Glu Ile Pro Val Ala Ser Thr Ile Asn
            20                  25                  30

gaa aaa gca gtt tta gga aaa gca att gaa aat act ttt gaa ctt caa
Glu Lys Ala Val Leu Gly Lys Ala Ile Glu Asn Thr Phe Glu Leu Gln
        35                  40                  45

tat gac cat act cct gat aaa gct gac aat cca aaa cca tct aat cct
Tyr Asp His Thr Pro Asp Lys Ala Asp Asn Pro Lys Pro Ser Asn Pro
    50                  55                  60

cca aga aaa cca gaa gtt cat act ggt ggg aaa cga ttt gta aag aaa
Pro Arg Lys Pro Glu Val His Thr Gly Gly Lys Arg Phe Val Lys Lys
65                  70                  75                  80

gac tca aca gaa aca caa aca cta ggt ggt gct gag ttt gat ttg ttg
Asp Ser Thr Glu Thr Gln Thr Leu Gly Gly Ala Glu Phe Asp Leu Leu
                85                  90                  95

gct tct gat ggg aca gca gta aaa tgg aca gat gct ctt att aaa gcg
Ala Ser Asp Gly Thr Ala Val Lys Trp Thr Asp Ala Leu Ile Lys Ala
            100                 105                 110

aat act aat aaa aac tat att gct gga gaa gct gtt act ggg caa cca
Asn Thr Asn Lys Asn Tyr Ile Ala Gly Glu Ala Val Thr Gly Gln Pro
        115                 120                 125

atc aaa ttg aaa tca cat aca gac ggt acg ttt gag att aaa ggt ttg
Ile Lys Leu Lys Ser His Thr Asp Gly Thr Phe Glu Ile Lys Gly Leu
    130                 135                 140

gct tat gca gtt gat gcg aat gca gag ggt aca gca gta act tac aaa
Ala Tyr Ala Val Asp Ala Asn Ala Glu Gly Thr Ala Val Thr Tyr Lys
145                 150                 155                 160

tta aaa gaa aca aaa gca cca gaa ggt tat gta atc cct gat aaa gaa
Leu Lys Glu Thr Lys Ala Pro Glu Gly Tyr Val Ile Pro Asp Lys Glu
                165                 170                 175

atc gag ttt aca gta tca caa aca tct tat aat aca aaa cca act gac
Ile Glu Phe Thr Val Ser Gln Thr Ser Tyr Asn Thr Lys Pro Thr Asp
            180                 185                 190

atc acg gtt gat agt gct gat gca aca cct gat aca att aaa aac aac
Ile Thr Val Asp Ser Ala Asp Ala Thr Pro Asp Thr Ile Lys Asn Asn
        195                 200                 205

aaa cgt cct tca atc cct aat act ggt ggt att ggt acg gct atc ttt
Lys Arg Pro Ser Ile Pro Asn Thr Gly Gly Ile Gly Thr Ala Ile Phe
    210                 215                 220

gtc gct atc ggt gct gcg gtg atg gct ttt gct gtt aag ggg atg aag
Val Ala Ile Gly Ala Ala Val Met Ala Phe Ala Val Lys Gly Met Lys
225                 230                 235                 240

cgt cgt aca aaa gat aac taa
Arg Arg Thr Lys Asp Asn
                245
```

*FIG. 2*

EmaB atg aaa caa aca tta aaa ctt atg ttt tct ttt ctg ttg atg tta ggg
Met Lys Gln Thr Leu Lys Leu Met Phe Ser Phe Leu Leu Met Leu Gly
1 5 10 15 act atg ttt gga att agc caa act gtt tta gcg caa gaa act cat cag
Thr Met Phe Gly Ile Ser Gln Thr Val Leu Ala Gln Glu Thr His Gln
20 25 30 ttg acg att gtt cat ctt gaa gca agg gat att gat cgt cca aat cca
Leu Thr Ile Val His Leu Glu Ala Arg Asp Ile Asp Arg Pro Asn Pro
35 40 45 cag ttg gag att gcc cct aaa gaa ggg act cca att gaa gga gta ctc
Gln Leu Glu Ile Ala Pro Lys Glu Gly Thr Pro Ile Glu Gly Val Leu
50 55 60 tat cag ttg tac caa tta aaa tca act gaa gat ggc gat ttg ttg gca
Tyr Gln Leu Tyr Gln Leu Lys Ser Thr Glu Asp Gly Asp Leu Leu Ala
65 70 75 80 cat tgg aat tcc cta act atc aca gaa ttg aaa aaa cag gcg cag cag
His Trp Asn Ser Leu Thr Ile Thr Glu Leu Lys Lys Gln Ala Gln Gln
85 90 95 gtt ttt gaa gcc act act aat caa caa gga aag gct aca ttt aac caa
Val Phe Glu Ala Thr Thr Asn Gln Gln Gly Lys Ala Thr Phe Asn Gln
100 105 110 cta cca gat gga att tat tat ggt ctg gcg gtt aaa gcc ggt gaa aaa
Leu Pro Asp Gly Ile Tyr Tyr Gly Leu Ala Val Lys Ala Gly Glu Lys
115 120 125 aat cgt aat gtc tca gct ttc ttg gtt gac ttg tct gag gat aaa gtg
Asn Arg Asn Val Ser Ala Phe Leu Val Asp Leu Ser Glu Asp Lys Val
130 135 140 att tat cct aaa atc atc tgg tcc aca ggt gag ttg gac ttg ctt aaa
Ile Tyr Pro Lys Ile Ile Trp Ser Thr Gly Glu Leu Asp Leu Leu Lys
145 150 155 160 gtt ggt gtg gat ggt gat acc aaa aaa cca cta gca ggc gtt gtc ttt
Val Gly Val Asp Gly Asp Thr Lys Lys Pro Leu Ala Gly Val Val Phe
165 170 175 gaa ctt tat gaa aag aat ggt agg act cct att cgt gtg aaa aat ggg
Glu Leu Tyr Glu Lys Asn Gly Arg Thr Pro Ile Arg Val Lys Asn Gly
180 185 190 gtg cat tct caa gat att gac gct gca aaa cat tta gaa aca gat tca
Val His Ser Gln Asp Ile Asp Ala Ala Lys His Leu Glu Thr Asp Ser
195 200 205 tca ggg cat atc aga att tcc ggg ctc atc cat ggg gac tat gtc tta
Ser Gly His Ile Arg Ile Ser Gly Leu Ile His Gly Asp Tyr Val Leu
210 215 220 aaa gaa atc gag aca cag tca gga tat cag atc gga cag gca gag act
Lys Glu Ile Glu Thr Gln Ser Gly Tyr Gln Ile Gly Gln Ala Glu Thr
225 230 235 240

*FIG. 3A*

```
gct gtg act att gaa aaa tca aaa aca gta aca gta acg att gaa aat
Ala Val Thr Ile Glu Lys Ser Lys Thr Val Thr Val Thr Ile Glu Asn
                245                 250                 255

aaa aaa gtt ccg aca cct aaa gtg cca tct cga gga ggt ctt att ccc
Lys Lys Val Pro Thr Pro Lys Val Pro Ser Arg Gly Gly Leu Ile Pro
            260                 265                 270

aaa aca ggt gag caa cag gca atg gca ctt gta att att ggt ggt att
Lys Thr Gly Glu Gln Gln Ala Met Ala Leu Val Ile Ile Gly Gly Ile
        275                 280                 285

tta att gct tta gcc tta cga tta cta tca aaa cat cgg aaa cat caa
Leu Ile Ala Leu Ala Leu Arg Leu Leu Ser Lys His Arg Lys His Gln
    290                 295                 300

aat aag gat tag
Asn Lys Asp
305
```

*FIG. 3B*

EmaC

```
atg gga caa aaa tca aaa ata tct cta gct acg aat att cgt ata tgg
Met Gly Gln Lys Ser Lys Ile Ser Leu Ala Thr Asn Ile Arg Ile Trp
1               5                   10                  15

att ttt cgt tta att ttc tta gcg ggt ttc ctt gtt ttg gca ttt ccc
Ile Phe Arg Leu Ile Phe Leu Ala Gly Phe Leu Val Leu Ala Phe Pro
            20                  25                  30

atc gtt agt cag gtc atg tac ttt caa gcc tct cac gcc aat att aat
Ile Val Ser Gln Val Met Tyr Phe Gln Ala Ser His Ala Asn Ile Asn
        35                  40                  45

gct ttt aaa gaa gct gtt acc aag att gac cgg gtg gag att aat cgg
Ala Phe Lys Glu Ala Val Thr Lys Ile Asp Arg Val Glu Ile Asn Arg
    50                  55                  60

cgt tta gaa ctt gct tat gct tat aac gcc agt ata gca ggt gcc aaa
Arg Leu Glu Leu Ala Tyr Ala Tyr Asn Ala Ser Ile Ala Gly Ala Lys
65                  70                  75                  80

act aat ggc gaa tat cca gcg ctt aaa gac ccc tac tct gct gaa caa
Thr Asn Gly Glu Tyr Pro Ala Leu Lys Asp Pro Tyr Ser Ala Glu Gln
                85                  90                  95

aag cag gca ggg gtc gtt gag tac gcc cgc atg ctt gaa gtc aaa gaa
Lys Gln Ala Gly Val Val Glu Tyr Ala Arg Met Leu Glu Val Lys Glu
            100                 105                 110

caa ata ggt cat gtg att att cca aga att aat cag gat atc cct att
Gln Ile Gly His Val Ile Ile Pro Arg Ile Asn Gln Asp Ile Pro Ile
        115                 120                 125

tac gct ggc tct gct gaa gaa aat ctt cag agg ggc gtt gga cat tta
Tyr Ala Gly Ser Ala Glu Glu Asn Leu Gln Arg Gly Val Gly His Leu
    130                 135                 140

gag ggg acc agt ctt cca gtc ggt ggt gag tca act cat gcc gtt cta
Glu Gly Thr Ser Leu Pro Val Gly Gly Glu Ser Thr His Ala Val Leu
145                 150                 155                 160

act gcc cat cga ggg cta cca acg gcc aag cta ttt acc aat tta gac
Thr Ala His Arg Gly Leu Pro Thr Ala Lys Leu Phe Thr Asn Leu Asp
                165                 170                 175

aag gta aca gta ggt gac cgt ttt tac att gaa cac atc ggc gga aag
Lys Val Thr Val Gly Asp Arg Phe Tyr Ile Glu His Ile Gly Gly Lys
            180                 185                 190

att gct tat cag gta gac caa atc aaa gtt atc gcc cct gat cag tta
Ile Ala Tyr Gln Val Asp Gln Ile Lys Val Ile Ala Pro Asp Gln Leu
        195                 200                 205

gag gat ttg tac gtg att caa gga gaa gat cac gtc acc cta tta act
Glu Asp Leu Tyr Val Ile Gln Gly Glu Asp His Val Thr Leu Leu Thr
    210                 215                 220

tgc aca cct tat atg ata aat agt cat cgc ctc ctc gtt cga ggc aag
Cys Thr Pro Tyr Met Ile Asn Ser His Arg Leu Leu Val Arg Gly Lys
225                 230                 235                 240

cga att cct tat gtg gaa aaa aca gtg cag aaa gat tca aag acc ttc
Arg Ile Pro Tyr Val Glu Lys Thr Val Gln Lys Asp Ser Lys Thr Phe
                245                 250                 255

agg caa caa caa tac cta acc tat gct atg tgg gta gtc gtt gga ctt
Arg Gln Gln Gln Tyr Leu Thr Tyr Ala Met Trp Val Val Val Gly Leu
            260                 265                 270

atc ttg ctg tcg ctt ctc att tgg ttt aaa aag acg aaa cag aaa aag
Ile Leu Leu Ser Leu Leu Ile Trp Phe Lys Lys Thr Lys Gln Lys Lys
        275                 280                 285

cgg aga aag aat gaa aaa gcg gct agt caa aat agt cac aat aat tcg
Arg Arg Lys Asn Glu Lys Ala Ala Ser Gln Asn Ser His Asn Asn Ser
    290                 295                 300

aaa taa
Lys
305
```

FIG. 4

EmaD

| | | | | | | | | | | | | | | | |
|---|---|---|---|---|---|---|---|---|---|---|---|---|---|---|---|
| atg | aaa | aag | cgg | cta | gtc | aaa | ata | gtc | aca | ata | att | cga | aat | aat | aaa |
| Met | Lys | Lys | Arg | Leu | Val | Lys | Ile | Val | Thr | Ile | Ile | Arg | Asn | Asn | Lys |
| 1 | | | | 5 | | | | | 10 | | | | | 15 | |
| atc | aga | acc | ctc | att | ttt | gtg | atg | gga | agt | ctg | att | ctc | tta | ttt | ccg |
| Ile | Arg | Thr | Leu | Ile | Phe | Val | Met | Gly | Ser | Leu | Ile | Leu | Leu | Phe | Pro |
| | | | 20 | | | | | 25 | | | | | 30 | | |
| att | gtg | agc | cag | gta | agt | tac | tac | ctt | gct | tcg | cat | caa | aat | att | aat |
| Ile | Val | Ser | Gln | Val | Ser | Tyr | Tyr | Leu | Ala | Ser | His | Gln | Asn | Ile | Asn |
| | | 35 | | | | | 40 | | | | | 45 | | | |
| caa | ttt | aag | cgg | gaa | gtc | gct | aag | att | gat | act | aat | acg | gtt | gaa | cga |
| Gln | Phe | Lys | Arg | Glu | Val | Ala | Lys | Ile | Asp | Thr | Asn | Thr | Val | Glu | Arg |
| | 50 | | | | | 55 | | | | | 60 | | | | |
| cgc | atc | gct | tta | gct | aat | gct | tac | aat | gag | acg | tta | tca | agg | aat | ccc |
| Arg | Ile | Ala | Leu | Ala | Asn | Ala | Tyr | Asn | Glu | Thr | Leu | Ser | Arg | Asn | Pro |
| 65 | | | | | 70 | | | | | 75 | | | | | 80 |
| ttg | ctt | ata | gac | cct | ttt | acc | agt | aag | caa | aaa | gaa | ggt | ttg | aga | gag |
| Leu | Leu | Ile | Asp | Pro | Phe | Thr | Ser | Lys | Gln | Lys | Glu | Gly | Leu | Arg | Glu |
| | | | | 85 | | | | | 90 | | | | | 95 | |
| tat | gct | cgt | atg | ctt | gaa | gtt | cat | gag | caa | ata | ggt | cat | gtg | gca | atc |
| Tyr | Ala | Arg | Met | Leu | Glu | Val | His | Glu | Gln | Ile | Gly | His | Val | Ala | Ile |
| | | | 100 | | | | | 105 | | | | | 110 | | |
| cca | agt | att | tgg | gtt | gat | att | cca | att | tat | gct | gga | aca | tcc | gaa | act |
| Pro | Ser | Ile | Trp | Val | Asp | Ile | Pro | Ile | Tyr | Ala | Gly | Thr | Ser | Glu | Thr |
| | | 115 | | | | | 120 | | | | | 125 | | | |
| gtg | ctt | cag | aaa | ggt | agt | ggg | cat | ttg | gag | gga | acc | agt | ctt | cca | gtg |
| Val | Leu | Gln | Lys | Gly | Ser | Gly | His | Leu | Glu | Gly | Thr | Ser | Leu | Pro | Val |
| | 130 | | | | | 135 | | | | | 140 | | | | |
| gga | ggt | ttg | tca | acc | cat | tca | gta | cta | act | gcc | cac | cgt | ggc | ttg | cca |
| Gly | Gly | Leu | Ser | Thr | His | Ser | Val | Leu | Thr | Ala | His | Arg | Gly | Leu | Pro |
| 145 | | | | | 150 | | | | | 155 | | | | | 160 |
| aca | gct | agg | cta | ttt | acc | gac | tta | aat | aaa | gtt | aaa | aaa | ggc | cag | att |
| Thr | Ala | Arg | Leu | Phe | Thr | Asp | Leu | Asn | Lys | Val | Lys | Lys | Gly | Gln | Ile |
| | | | | 165 | | | | | 170 | | | | | 175 | |
| ttc | tat | gtg | acg | aac | atc | aag | gaa | aca | ctt | gcc | tac | aaa | gtc | gtg | tct |
| Phe | Tyr | Val | Thr | Asn | Ile | Lys | Glu | Thr | Leu | Ala | Tyr | Lys | Val | Val | Ser |
| | | | 180 | | | | | 185 | | | | | 190 | | |
| atc | aaa | gtt | gtg | gat | cca | aca | gct | tta | agt | gag | gtt | aag | att | gtc | aat |
| Ile | Lys | Val | Val | Asp | Pro | Thr | Ala | Leu | Ser | Glu | Val | Lys | Ile | Val | Asn |
| | | 195 | | | | | 200 | | | | | 205 | | | |
| ggt | aag | gat | tat | ata | acc | ttg | ctg | act | tgc | aca | cct | tac | atg | atc | aat |
| Gly | Lys | Asp | Tyr | Ile | Thr | Leu | Leu | Thr | Cys | Thr | Pro | Tyr | Met | Ile | Asn |
| | 210 | | | | | 215 | | | | | 220 | | | | |
| agt | cat | cgt | ctc | ttg | gta | aaa | gga | gag | cgt | att | cct | tat | gat | tct | acc |
| Ser | His | Arg | Leu | Leu | Val | Lys | Gly | Glu | Arg | Ile | Pro | Tyr | Asp | Ser | Thr |
| 225 | | | | | 230 | | | | | 235 | | | | | 240 |
| gag | gcg | gaa | aag | cac | aaa | gaa | caa | acc | gta | caa | gat | tat | cgt | ttg | tca |
| Glu | Ala | Glu | Lys | His | Lys | Glu | Gln | Thr | Val | Gln | Asp | Tyr | Arg | Leu | Ser |
| | | | | 245 | | | | | 250 | | | | | 255 | |
| cta | gtg | ttg | aag | ata | cta | cta | gta | tta | tta | att | gga | ctc | ttc | atc | gtg |
| Leu | Val | Leu | Lys | Ile | Leu | Leu | Val | Leu | Leu | Ile | Gly | Leu | Phe | Ile | Val |
| | | | 260 | | | | | 265 | | | | | 270 | | |
| ata | atg | atg | aga | aga | tgg | atg | caa | cat | cgt | caa | taa | | | | |
| Ile | Met | Met | Arg | Arg | Trp | Met | Gln | His | Arg | Gln | | | | | |
| | | 275 | | | | | 280 | | | | | | | | |

FIG. 5

EmaE

```
atg atg att gtg aat aat ggt tat cta gaa ggg aga aaa atg aaa aag
Met Met Ile Val Asn Asn Gly Tyr Leu Glu Gly Arg Lys Met Lys Lys
1               5                   10                  15

aga caa aaa ata tgg aga ggg tta tca gtt act tta cta atc ctg tcc
Arg Gln Lys Ile Trp Arg Gly Leu Ser Val Thr Leu Leu Ile Leu Ser
            20                  25                  30

caa att cca ttt ggt ata ttg gta caa ggt gaa acc caa gat acc aat
Gln Ile Pro Phe Gly Ile Leu Val Gln Gly Glu Thr Gln Asp Thr Asn
        35                  40                  45

caa gca ctt gga aaa gta att gtt aaa aaa acg gga gac aat gct aca
Gln Ala Leu Gly Lys Val Ile Val Lys Lys Thr Gly Asp Asn Ala Thr
    50                  55                  60

cca tta ggc aaa gcg act ttt gtg tta aaa aat gac aat gat aag tca
Pro Leu Gly Lys Ala Thr Phe Val Leu Lys Asn Asp Asn Asp Lys Ser
65                  70                  75                  80

gaa aca agt cac gaa acg gta gag ggt tct gga gaa gca acc ttt gaa
Glu Thr Ser His Glu Thr Val Glu Gly Ser Gly Glu Ala Thr Phe Glu
                85                  90                  95

aac ata aaa cct gga gac tac aca tta aga gaa gaa aca gca cca att
Asn Ile Lys Pro Gly Asp Tyr Thr Leu Arg Glu Glu Thr Ala Pro Ile
            100                 105                 110

ggt tat aaa aaa act gat aaa acc tgg aaa gtt aaa gtt gca gat aac
Gly Tyr Lys Lys Thr Asp Lys Thr Trp Lys Val Lys Val Ala Asp Asn
        115                 120                 125

gga gca aca ata atc gag ggt atg gat gca gat aaa gca gag aaa cga
Gly Ala Thr Ile Ile Glu Gly Met Asp Ala Asp Lys Ala Glu Lys Arg
    130                 135                 140

aaa gaa gtt ttg aat gcc caa tat cca aaa tca gct att tat gag gat
Lys Glu Val Leu Asn Ala Gln Tyr Pro Lys Ser Ala Ile Tyr Glu Asp
145                 150                 155                 160

aca aaa gaa aat tac cca tta gtt aat gta gag ggt tcc aaa gtt ggt
Thr Lys Glu Asn Tyr Pro Leu Val Asn Val Glu Gly Ser Lys Val Gly
                165                 170                 175

gaa caa tac aaa gca ttg aat cca ata aat gga aaa gat ggt cga aga
Glu Gln Tyr Lys Ala Leu Asn Pro Ile Asn Gly Lys Asp Gly Arg Arg
            180                 185                 190

gag att gct gaa ggt tgg tta tca aaa aaa aat aca ggg gtc aat gat
Glu Ile Ala Glu Gly Trp Leu Ser Lys Lys Asn Thr Gly Val Asn Asp
        195                 200                 205

ctc gat aag aat aaa tat aaa att gaa tta act gtt gag ggt aaa acc
Leu Asp Lys Asn Lys Tyr Lys Ile Glu Leu Thr Val Glu Gly Lys Thr
    210                 215                 220

act gtt gaa acg aaa gaa ctt aat caa cca cta gat gtc gtt gtg cta
Thr Val Glu Thr Lys Glu Leu Asn Gln Pro Leu Asp Val Val Val Leu
225                 230                 235                 240
```

FIG. 6A

```
tta gat aat tca aat agt atg aat aat gaa aga gcc aat aat tct caa
Leu Asp Asn Ser Asn Ser Met Asn Asn Glu Arg Ala Asn Asn Ser Gln
                245                 250                 255

aga gca tta aaa gct ggg gaa gca gtt gaa aag ctg att gat aaa att
Arg Ala Leu Lys Ala Gly Glu Ala Val Glu Lys Leu Ile Asp Lys Ile
            260                 265                 270

aca tca aat aaa gac aat aga gta gct ctt gtg aca tat gcc tca acc
Thr Ser Asn Lys Asp Asn Arg Val Ala Leu Val Thr Tyr Ala Ser Thr
        275                 280                 285

att ttt gat ggt act gaa gcg acc gta tca aag gga gtt gcc gat caa
Ile Phe Asp Gly Thr Glu Ala Thr Val Ser Lys Gly Val Ala Asp Gln
    290                 295                 300

aat ggt aaa gcg ctg aat gat agt gta tca tgg gat tat cat aaa act
Asn Gly Lys Ala Leu Asn Asp Ser Val Ser Trp Asp Tyr His Lys Thr
305                 310                 315                 320

act ttt aca gca act aca cat aat tac agt tat tta aat tta aca aat
Thr Phe Thr Ala Thr Thr His Asn Tyr Ser Tyr Leu Asn Leu Thr Asn
                325                 330                 335

gat gct aac gaa gtt aat att cta aag tca aga att cca aag gaa gcg
Asp Ala Asn Glu Val Asn Ile Leu Lys Ser Arg Ile Pro Lys Glu Ala
            340                 345                 350

gag cat ata aat ggg gat cgc acg ctc tat caa ttt ggt gcg aca ttt
Glu His Ile Asn Gly Asp Arg Thr Leu Tyr Gln Phe Gly Ala Thr Phe
        355                 360                 365

act caa aaa gct cta atg aaa gca aat gaa att tta gag aca caa agt
Thr Gln Lys Ala Leu Met Lys Ala Asn Glu Ile Leu Glu Thr Gln Ser
    370                 375                 380

tct aat gct aga aaa aaa ctt att ttt cac gta act gat ggt gtc cct
Ser Asn Ala Arg Lys Lys Leu Ile Phe His Val Thr Asp Gly Val Pro
385                 390                 395                 400

acg atg tct tat gcc ata aat ttt aat cct tat ata tca aca tct tac
Thr Met Ser Tyr Ala Ile Asn Phe Asn Pro Tyr Ile Ser Thr Ser Tyr
                405                 410                 415

caa aac cag ttt aat tct ttt tta aat aaa ata cca gat aga agt ggt
Gln Asn Gln Phe Asn Ser Phe Leu Asn Lys Ile Pro Asp Arg Ser Gly
            420                 425                 430

att ctc caa gag gat ttt ata atc aat ggt gat gat tat caa ata gta
Ile Leu Gln Glu Asp Phe Ile Ile Asn Gly Asp Asp Tyr Gln Ile Val
        435                 440                 445

aaa gga gat gga gag agt ttt aaa ctg ttt tcg gat aga aaa gtt cct
Lys Gly Asp Gly Glu Ser Phe Lys Leu Phe Ser Asp Arg Lys Val Pro
    450                 455                 460

gtt act gga gga acg aca caa gca gct tat cga gta ccg caa aat caa
Val Thr Gly Gly Thr Thr Gln Ala Ala Tyr Arg Val Pro Gln Asn Gln
465                 470                 475                 480
```

FIG. 6B

```
ctc tct gta atg agt aat gag gga tat gca att aat agt gga tat att
Leu Ser Val Met Ser Asn Glu Gly Tyr Ala Ile Asn Ser Gly Tyr Ile
                485                 490                 495

tat ctc tat tgg aga gat tac aac tgg gtc tat cca ttt gat cct aag
Tyr Leu Tyr Trp Arg Asp Tyr Asn Trp Val Tyr Pro Phe Asp Pro Lys
            500                 505                 510

aca aag aaa gtt tct gca acg aaa caa atc aaa act cat ggt gag cca
Thr Lys Lys Val Ser Ala Thr Lys Gln Ile Lys Thr His Gly Glu Pro
        515                 520                 525

aca aca tta tac ttt aat gga aat ata aga cct aaa ggt tat gac att
Thr Thr Leu Tyr Phe Asn Gly Asn Ile Arg Pro Lys Gly Tyr Asp Ile
    530                 535                 540

ttt act gtt ggg att ggt gta aac gga gat cct ggt gca act cct ctt
Phe Thr Val Gly Ile Gly Val Asn Gly Asp Pro Gly Ala Thr Pro Leu
545                 550                 555                     560

gaa gct gag aaa ttt atg caa tca ata tca agt aaa aca gaa aat tat
Glu Ala Glu Lys Phe Met Gln Ser Ile Ser Ser Lys Thr Glu Asn Tyr
                565                 570                 575

act aat gtt gat gat aca aat aaa att tat gat gag cta aat aaa tac
Thr Asn Val Asp Asp Thr Asn Lys Ile Tyr Asp Glu Leu Asn Lys Tyr
            580                 585                 590

ttt aaa aca att gtt gag gaa aaa cat tct att gtt gat gga aat gtg
Phe Lys Thr Ile Val Glu Glu Lys His Ser Ile Val Asp Gly Asn Val
        595                 600                 605

act gat cct atg gga gag atg att gaa ttc caa tta aaa aat ggt caa
Thr Asp Pro Met Gly Glu Met Ile Glu Phe Gln Leu Lys Asn Gly Gln
    610                 615                 620

agt ttt aca cat gat gat tac gtt ttg gtt gga aat gat ggc agt caa
Ser Phe Thr His Asp Asp Tyr Val Leu Val Gly Asn Asp Gly Ser Gln
625                 630                 635                     640

tta aaa aat ggt gtg gct ctt ggt gga cca aac agt gat ggg gga att
Leu Lys Asn Gly Val Ala Leu Gly Gly Pro Asn Ser Asp Gly Gly Ile
                645                 650                 655

tta aaa gat gtt aca gtg act tat gat aag aca tct caa acc atc aaa
Leu Lys Asp Val Thr Val Thr Tyr Asp Lys Thr Ser Gln Thr Ile Lys
            660                 665                 670

atc aat cat ttg aac tta gga agt gga caa aaa gta gtt ctt acc tat
Ile Asn His Leu Asn Leu Gly Ser Gly Gln Lys Val Val Leu Thr Tyr
        675                 680                 685

gat gta cgt tta aaa gat aac tat ata agt aac aaa ttt tac aat aca
Asp Val Arg Leu Lys Asp Asn Tyr Ile Ser Asn Lys Phe Tyr Asn Thr
    690                 695                 700

aat aat cgt aca acg cta agt ccg aag agt gaa aaa gaa cca aat act
Asn Asn Arg Thr Thr Leu Ser Pro Lys Ser Glu Lys Glu Pro Asn Thr
705                 710                 715                     720
```

FIG. 6C att cgt gat ttc cca att ccc aaa att cgt gat gtt cgt gag ttt ccg
Ile Arg Asp Phe Pro Ile Pro Lys Ile Arg Asp Val Arg Glu Phe Pro
725 730 735 gta cta acc atc agt aat cag aag aaa atg ggt gag gtt gaa ttt att
Val Leu Thr Ile Ser Asn Gln Lys Lys Met Gly Glu Val Glu Phe Ile
740 745 750 aaa gtt aat aaa gac aaa cat tca gaa tcg ctt ttg gga gct aag ttt
Lys Val Asn Lys Asp Lys His Ser Glu Ser Leu Leu Gly Ala Lys Phe
755 760 765 caa ctt cag ata gaa aaa gat ttt tct ggg tat aag caa ttt gtt cca
Gln Leu Gln Ile Glu Lys Asp Phe Ser Gly Tyr Lys Gln Phe Val Pro
770 775 780 gag gga agt gat gtt aca aca aag aat gat ggt aaa att tat ttt aaa
Glu Gly Ser Asp Val Thr Thr Lys Asn Asp Gly Lys Ile Tyr Phe Lys
785 790 795 800 gca ctt caa gat ggt aac tat aaa tta tat gaa att tca agt cca gat
Ala Leu Gln Asp Gly Asn Tyr Lys Leu Tyr Glu Ile Ser Ser Pro Asp
805 810 815 ggc tat ata gag gtt aaa acg aaa cct gtt gtg aca ttt aca att caa
Gly Tyr Ile Glu Val Lys Thr Lys Pro Val Val Thr Phe Thr Ile Gln
820 825 830 aat gga gaa gtt acg aac ctg aaa gca gat cca aat gct aat aaa aat
Asn Gly Glu Val Thr Asn Leu Lys Ala Asp Pro Asn Ala Asn Lys Asn
835 840 845 caa atc ggg tat ctt gaa gga aat ggt aaa cat ctt att acc aac act
Gln Ile Gly Tyr Leu Glu Gly Asn Gly Lys His Leu Ile Thr Asn Thr
850 855 860 ccc aaa cgc cca cca ggt gtt ttt cct aaa aca ggg gga att ggt aca
Pro Lys Arg Pro Pro Gly Val Phe Pro Lys Thr Gly Gly Ile Gly Thr
865 870 875 880 att gtc tat ata tta gtt ggt tct act ttt atg ata ctt acc att tgt
Ile Val Tyr Ile Leu Val Gly Ser Thr Phe Met Ile Leu Thr Ile Cys
885 890 895 tct ttc cgt cgt aaa caa ttg taa
Ser Phe Arg Arg Lys Gln Leu
900

FIG. 6D

GROUP B *STREPTOCOCCUS* POLYPEPTIDES, NUCLEIC ACIDS AND THERAPEUTIC COMPOSITIONS AND VACCINES THEREOF

INTRODUCTION

This application is a divisional of U.S. patent application Ser. No. 12/632,269, filed Dec. 7, 2009, which is a divisional of U.S. patent application Ser. No. 11/493,705 filed Jul. 26, 2006, now U.S. Pat. No. 7,645,577, which is a continuation application of U.S. patent application Ser. No. 10/333,002, filed Jul. 8, 2003, now U.S. Pat. No. 7,128,919, which is a U.S. National Stage application of PCT/US2001/024795 filed Aug. 8, 2001, which claims the benefit of priority to U.S. application Ser. No. 09/634,341, filed Aug. 8, 2000, each of which are herein incorporated by reference in their entirety.

The research leading to the present invention was supported, at least in part, by a grant from NAID, Grant No. A140918. Accordingly, the Government has certain rights in the invention.

FIELD OF THE INVENTION

This invention relates generally to extracellular matrix adhesin (Ema) proteins, antibodies thereto and to vaccines, compositions and therapeutics. The Group B streptococcal Ema polypeptides are EmaA, EmaB, EmaC, EmaD and EmaE. The invention further relates to Ema polypeptides from various species of bacteria, including *S. pneumoniae, S. pyogenes, E. faecalis* and *C. diptheriae*. The invention also relates to the identification and prevention of infections by streptococci. Isolated nucleic acids encoding Group B streptococcal Ema polypeptides, particularly EmaA, EmaB, EmaC, EmaD and EmaE and to other bacterial Ema homologs are included herein. Assays for compounds which modulate the polypeptides of the present invention for use in therapy are also provided.

BACKGROUND OF THE INVENTION

Streptococci are catalase negative gram positive cocci. They may be classified by the type of hemolysis exhibited on blood agar, by the serologic detection of carbohydrate antigens, or by certain biochemical reactions. Medically important streptococci include Groups A, B, D, *S. pneumoniae* and the viridans group of streptococci. Lancefield type A (Group A) *Streptococcus* pyogenes is an important human pathogen—the cause of streptococcal pharyngitis, impetigo and more severe infections such as bacterernia and necrotizing fascitis. The immunologic sequelae of Group A Streptococcal infections are also important health problems—rheumatic carditis is the most common cause of acquired cardiac disease worldwide and post-streptococcal glomerulonephritis is a cause of hypertension and renal dysfunction. Group B *Streptococcus* agalactiae are the most common cause of serious bacterial infections in newborns, and important pathogens in pregnant women and nonpregnant adults with underlying medical problems such as diabetes and cardiovascular disease. Group D streptococci include the enterococci (*Streptococcus faecalis* and *faecium*) and the "nonenterococcal" Group D streptococci. *Streptococcus pneumoniae* (*pneumococcus*) is not classified by group in the Lancefield system. Pneumococci are extremely important human pathogens, the most common cause of bacterial pneumonia, middle ear infections and meningitis beyond the newborn period. The viridans group of streptococci include *S. milleri, S. mitis, S. sanguis* and others. They cause bacteremia, endocarditis, and dental infections. Enterococci are important causes of urinary tract infections, bacteremia and wound infections (predominantly as nosocomial infections in hospitalized patients), and endocarditis. Over the past decade enterococci have developed resistance to many conventional antibiotics and there are some strains resistant to all known antibiotics.

Group B streptococci (GBS) are the most common cause of serious bacterial disease in neonates, and are important pathogens in pregnant women and adults with underlying illnesses (Baker C J. (2000) "Group B streptococcal infections" in Streptococcal infections. Clinical aspects, microbiology, and molecular pathogenesis. (D. L. Stevens and E. L. Kaplan), New York: Oxford University Press, 222-237). Common manifestations of these infections include bacteremia, pneumonia, meningitis, endocarditis, and osteoarticular infections (Baker C J. (2000) "Group B streptococcal infections" in Streptococcal infections. Clinical aspects, microbiology, and molecular pathogenesis. (D. L. Stevens and E. L. Kaplan), New York: Oxford University Press, 222-237; Blumberg H. M. et al. (1996) J Infect Dis 173:365-373). The incidence of invasive GBS disease is approximately 2.6 in 1000 live births and 7.7 in 100,000 in the overall population, with mortality rates that vary from 6 to 30% (Baker C J. (2000) "Group B streptococcal infections" in Streptococcal infections. Clinical aspects, microbiology, and molecular pathogenesis. (D. L. Stevens and E. L. Kaplan), New York: Oxford University Press, 222-237; Blumberg H. M. et al. (1996) J Infect Dis 173:365-373). Although much neonatal disease is preventable by administration of prophylactic antibiotics to women in labor, antibiotic prophylaxis programs can be inefficient, suffer from poor compliance, or fail if antibiotic resistance emerges. No effective prophylaxis strategy for adult infections has been established.

During childbirth, GBS can pass from the mother to the newborn. By one estimate, up to 30% of pregnant women carry GBS at least temporarily in the vagina or rectum without symptoms. Infants born to these women become colonized with GBS during delivery (Baker, C. J. and Edwards, M. S. (1995) "Group B Streptococcal Infections" in Infectious Disease of the Fetus and Newborn Infant (J. S. Remington and J. O Klein), 980-1054). Aspiration of infected amniotic fluid or vaginal secretions allow GBS to gain access to the lungs. Adhesion to, and invasion of, respiratory epithelium and endothelium appear to be critical factors in early onset neonatal infection. (Baker, C. J. and Edwards, M. S. (1995) "Group B Streptococcal Infections" in Infectious Disease of the Fetus and Newborn Infant (J. S. Remington and J. O Klein), 980-1054; Rubens, C. E. et al. (1991) J Inf Dis 164: 320-330). Subsequent steps in infection, such as blood stream invasion and the establishment of metastatic local infections have not been clarified. The pathogenesis of neonatal infection occurring after the first week of life is also not well understood. Gastrointestinal colonization may be more important than a respiratory focus in late onset neonatal disease (Baker, C. J. and Edwards, M. S. (1995) "Group B Streptococcal Infections" in Infectious Disease of the Fetus and Newborn Infant (J. S. Remington and J. O Klein), 980-1054). Considerable evidence suggests that invasion of brain microvascular endothelial cells by GBS is the initial step in the pathogenesis of meningitis. GBS are able to invade human brain microvascular endothelial cells and type III GBS, which are responsible for the majority of meningitis, accomplish this 2-6 times more efficiently than other serotypes (Nizet, V. et al. (1997) Infect Immun 65:5074-5081).

Because GBS is widely distributed among the population and is an important pathogen in newborns, pregnant women are commonly tested for GBS at 35-37 weeks of pregnancy.

Much of GBS neonatal disease is preventable by administration of prophylactic antibiotics during labor to women who test positive or display known risk factors. However, these antibiotics programs do not prevent all GBS disease. The programs are deficient for a number of reasons. First, the programs can be inefficient. Second, it is difficult to ensure that all healthcare providers and patients comply with the testing and treatment. And finally, if new serotypes or antibiotic resistance emerges, the antibiotic programs may fail altogether. Currently available tests for GBS are inefficient. These tests may provide false negatives. Furthermore, the tests are not specific to virulent strains of GBS. Thus, antibiotic treatment may be given unnecessarily and add to the problem of antibiotic resistance. Although a vaccine would be advantageous, none are yet commercially available.

Traditionally, GBS are divided into 9 serotypes according to the immunologic reactivity of the polysaccharide capsule (Baker C J. (2000) "Group B streptococcal infections" in Streptococcal infections. Clinical aspects, microbiology, and molecular pathogenesis. (D. L. Stevens and E. L. Kaplan), New York: Oxford University Press, 222-237; Blumberg H. M. et al. (1996) J Infect Dis 173:365-373; Kogan, G. et al. (1996) J Biol Chem 271:8786-8790). Serotype III GBS are particularly important in human neonates, causing 60-70% of all infections and almost all meningitis (Baker C J. (2000) "Group B streptococcal infections" in Streptococcal infections Clinical aspects, microbiology, and molecular pathogenesis. (D. L. Stevens and E. L. Kaplan), New York: Oxford University Press, 222-237). Type III GBS can be subdivided into three groups of related strains based on the analysis of restriction digest patterns (RDPs) produced by digestion of chromosomal DNA with Hind III and Sse8387. (I. Y. Nagano et al. (1991) J Med Micro 35:297-303; S. Takahashi et al. (1998) J Inf Dis 177:1116-1119).

Over 90% of invasive type III GBS neonatal disease in Tokyo, Japan and in Salt Lake City, Utah is caused by bacteria from one of three RDP types, termed RDP type III-3, while RDP type III-2 are significantly more likely to be isolated from vagina than from blood or CSF. These results suggest that this genetically-related cluster of type III-3 GBS are more virulent than III-2 strains and could be responsible for the majority of invasive type III disease globally.

Preliminary vaccines for GBS used unconjugated purified polysaccaride. GBS poly- and oligosaccharides are poorly immunogenic and fail to elicit significant memory and booster responses. Baker et al immunized 40 pregnant women with purified serotype III capsular polysaccharide (Baker, C. J. et al. (1998) New Engl J of Med 319:1180-1185). Overall, only 57% of women with low levels of specific antibody responded to the vaccine. The poor immunogenicity of purified polysaccharide antigen was further demonstrated in a study in which thirty adult volunteers were immunized with a tetravalent vaccine composed of purified polysaccharide from serotypes Ia, Ib, II, and III (Kotloff, K. L. et al. (1996) Vaccine 14:446-450). Although safe, this vaccine was only modestly immunogenic, with only 13% of subjects responding to type Ib, 17% to type II, 33% responding to type Ia, and 70% responding to type III polysaccharide. The poor immunogenicity of polysaccharide antigens prompted efforts to develop polysaccharide conjugate vaccines, whereby these poly- or oligosaccharides are conjugated to protein carriers. Ninety percent of healthy adult women immunized with a type III polysaccharide-tetanus toxoid conjugate vaccine responded with a 4-fold rise in antibody concentration, compared to 50% immunized with plain polysaccharide (Kasper, D. L. et al (1996) J of Clin Invest 98:2308-2314). A type Ia/Ib polysaccharide-tetanus toxoid conjugate vaccine was similarly more immunogenic in healthy adults than plain polysaccharide (Baker, C. J. et al (1999) J Infect Dis 179:142-150).

The disadvantage of polysaccharide-protein conjugate vaccines is that the process of purifying and conjugating polysaccharides is difficult, time-consuming and expensive. A protein antigen which could be cheaply and easily produced would be an improvement.

If one were to make a polysaccharide-protein conjugate vaccine, a GBS-specific carrier protein may be preferable to one of the commonly used carriers such as tetanus or diphtheria toxoids because of the potential problems associated with some of these carrier proteins, particularly variable immunogenicity and the problems associated with repeated vaccination with the same carrier protein. Selection of appropriate carrier proteins is important for the development of polysaccharide-protein vaccine formulations. For example, *Haemophilus influenzae* type b poly- or oligosaccharide conjugated to different protein carriers has variable immunogenicity and elicits antibody with varying avidity (Decker, M. D. et al (1992) J Pediatrics 120:184-189; Schlesinger, Y. (1992) JAMA 267:1489-1494). Repeated immunization with the same carrier protein may also suppress immune responses by competition for specific B cells (epitopic suppression) or other mechanisms. This is of particular concern for the development of GBS vaccines since recently developed poly/oligosaccharide-protein conjugate vaccines against the bacteria *H. influenzae, S. pneumoniae*, and *N. meningitidis* all utilize a restricted number of carrier proteins (tetanus toxoid, CRM197, diptheria toxoid), increasing the number of exposures to these carriers an individual is likely to receive. Additionally, using tetanus as a carrier protein offers no specific advantage beyond the improved immunogenicity of the vaccine. A second-generation vaccine containing a GBS-specific carrier protein would enhance immunogenicity and have an advantage in that a GBS-specific immune response would be generated against both the carrier protein and the poly/oligosaccharide.

Therefore, in view of the aforementioned deficiencies attendant with prior art vaccines and methods, it should be apparent that there still exists a need in the art for an effective and immunogenic GBS vaccine. The availability and use of a GBS polypeptide in a conjugate vaccine is desirable. A GBS polypeptide which is present or expressed in all GBS serotypes would have the added advantage of providing broad, general immunity across many GBS serotypes. It would be particularly relevant and useful to provide a streptococcal vaccine or immunogen which is expressed broadly in various streptococcal species, whereby broad or general immunity against multiple and unique groups of streptococci (for instance, Group A, Group B and *S. pneumoniae*), particularly against distinct virulent and clinically relevant streptococcal bacteria, could thereby be generated.

The citation of references herein shall not be construed as an admission that such is prior art to the present invention.

SUMMARY OF THE INVENTION

In accordance with the present invention, streptococcal polypeptides termed extracellular matrix adhesins (Ema) are provided which are particularly useful in the identification and prevention of infections by streptococci.

In its broadest aspect, the present invention encompasses isolated polypeptides comprising an amino acid sequence of a streptococcal polypeptide selected from the group of EmaA, EmaB, EmaC, EmaD and EmaE. The isolated peptides, including combinations of one or more thereof, are suitable for use in immunizing animals and humans against bacterial infection, particularly streptococci.

The present invention is directed to an isolated streptococcal EmaA polypeptide which comprises the amino acid sequence set out in SEQ ID NO:2, and analogs, variants and immunogenic fragments thereof.

The present invention is directed to an isolated streptococcal EmaB polypeptide which comprises the amino acid sequence set out in SEQ ID NO:4, and analogs, variants and immunogenic fragments thereof.

The present invention is directed to an isolated streptococcal EmaC polypeptide which comprises the amino acid sequence set out in SEQ ID NO:6, and analogs, variants and immunogenic fragments thereof.

The present invention is directed to an isolated streptococcal EmaD polypeptide which comprises the amino acid sequence set out in SEQ ID NO:8, and analogs, variants and immunogenic fragments thereof.

The present invention is directed to an isolated streptococcal EmaE polypeptide which comprises the amino acid sequence set out in SEQ ID NO:10, and analogs, variants and immunogenic fragments thereof.

The present invention also provides Ema polypeptide homologs from distinct bacterial species, particularly including distinct streptococcal species, more particularly including Group B *streptococcus*, Group A *streptococcus* (particularly *S. pyogenes*) and *S. pneumoniae*. The present invention also provides Ema polypeptides from additional distinct bacterial species, particularly including *Enterococcus faecalis* and *Corynebacterium diptheriae*. Nucleic acids encoding Ema polypeptide homologs from distinct bacterial species are also provided.

The present invention thus provides an isolated streptococcal Ema polypeptide comprising the amino acid sequence set out in SEQ ID NO:23. An isolated nucleic acid which encodes the streptococcal polypeptide set out in SEQ ID NO:23 is further provided.

The invention thus further provides an isolated streptococcal Ema polypeptide comprising the amino acid sequence set out in SEQ ID NO:26. An isolated nucleic acid which encodes the streptococcal polypeptide set out in SEQ ID NO:26 is further provided.

The present invention further provides an isolated streptococcal Ema polypeptide comprising the amino acid sequence set out in SEQ ID NO:37. An isolated nucleic acid which encodes the streptococcal polypeptide set out in SEQ ID NO:37 is further provided.

An enterococcal Ema polypeptide is further provided comprising the amino acid sequence set out in SEQ ID NO:29. An isolated nucleic acid which encodes the enterococcal polypeptide set out in SEQ ED NO:29 is also provided.

The invention provides an isolated *Corynebacterium* Ema polypeptide comprising the amino acid sequence set out in SEQ ID NO:32. Also provided is an isolated nucleic acid which encodes the *Corynebacterium* polypeptide set out in SEQ ID NO:32.

The invention provides an isolated bacterial polypeptide comprising the amino acid sequence TLLTCTPYMINS/THRLLVR/KG (SEQ ID NO:34), wherein the polypeptide is not isolated from *Actinomyces*.

The invention further provides an isolated streptococcal polypeptide comprising the amino acid sequence TLLTCTPYMINS/THRLLVR/KG (SEQ ID NO:34).

Also provided is an isolated bacterial polypeptide comprising the amino acid sequence TLVTCTPYGINTHRLLVTA. (SEQ ID NO:35)

The present invention includes an isolated bacterial polypeptide comprising the amino acid sequence TLVTCTPYGVNTKRLLVRG (SEQ ID NO:36). An isolated streptococcal polypeptide comprising the amino acid sequence TLVTCTPYGVNTKRLLVRG (SEQ ID NO:36) is also provided.

The invention further includes an isolated polypeptide having the amino acid sequence selected from the group of TLLTCTPYMINS/THRLLVR/KG (SEQ ID NO:34), TLVTCTPYGINTHRLLVTA (SEQ ID NO:35), and TLVTCTPYGVNTKRLLVRG (SEQ ID NO: 36).

The present invention contemplates the use of the polypeptides of the present invention in diagnostic tests and methods for determining and/or monitoring of streptococcal infection. Thus, the present invention provides an isolated Ema polypeptide, particularly selected from the group of EmaA, EmaB, EmaC, EmaD and EmaE, labeled with a detectable label.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

The present invention extends to an immunogenic Ema polypeptide, particularly selected from the group of EmaA, EmaB, EmaC, EmaD and EmaE, or a fragment thereof. The present invention also extends to immunogenic Ema polypeptides wherein such polypeptides comprise a combination of at least one immunogenic Ema polypeptide, selected from the group of EmaA, EmaB, EmaC, EmaD and EmaE, or immunogenic polypeptide fragment thereof, and a GBS polypeptide selected from the group of Spb1, Spb2, C protein alpha antigen, Rib, Lmb, C5a-ase, or immunogenic fragments thereof.

In a further aspect, the present invention extends to vaccines based on the Ema proteins described herein. The present invention provides a vaccine comprising one or more streptococcal polypeptides selected from the group of EmaA, EmaB, EmaC, EmaD and EmaE, and a pharmaceutically acceptable adjuvant. The present invention provides a vaccine comprising one or more streptococcal polypeptides selected from the group of the polypeptide of SEQ ID NO:23, 26, and 37, and a pharmaceutically acceptable adjuvant.

The present invention further provides a streptococcal vaccine comprising one or more Group B streptococcal polypeptides selected from the group of EmaA, EmaB, EmaC, EmaD and EmaE, further comprising one or more additional streptococcal antigens.

The present invention further provides a GBS vaccine comprising one or more Group B streptococcal polypeptides selected from the group of EmaA, EmaB, EmaC, EmaD and EmaE, further comprising one or more additional GBS antigens. In a particular embodiment, the GBS antigen is selected from the group of the polypeptide Spb1 or an immunogenic fragment thereof, the polypeptide Spb2 or an immunogenic fragment thereof, C protein alpha antigen or an immunogenic fragment thereof, Rib or an immunogenic fragment thereof. Lmb or an immunogenic fragment thereof, C5a-ase or an immunogenic fragment thereof and Group B streptococcal polysaccharides or oligosaccharides.

In another aspect, the invention is directed to a vaccine for protection of an animal subject from infection with streptococci comprising an immunogenic amount of one or more Ema polypeptide EmaA, EmaB, EmaC, EmaD or EmaE, or a derivative or fragment thereof. Such a vaccine may contain the protein conjugated covalently to a GBS bacterial polysaccharide or oligosaccharide or polysaccharide or oligosaccharide from one or more GBS serotypes.

In a still further aspect, the present invention provides an immunogenic composition comprising one of more streptococcal polypeptides selected from the group of EmaA, EmaB, EmaC, EmaD and EmaE, and a pharmaceutically acceptable adjuvant.

The present invention further provides an immunogenic composition comprising one or more Group B streptococcal polypeptide selected from the group of EmaA, EmaB, EmaC, EmaD and EmaE, further comprising one or more antigens selected from the group of the polypeptide Spb1 or an immunogenic fragment thereof, the polypeptide Spb2 or an immunogenic fragment thereof, C protein alpha antigen or an immunogenic fragment thereof, Rib or an immunogenic fragment thereof. Lmb or an immunogenic fragment thereof, C5a-ase or an immunogenic fragment thereof, and Group B streptococcal polysaccharides or oligosaccharides.

The invention further provides pharmaceutical compositions, vaccines, and diagnostic and therapeutic methods of use thereof.

The invention provides pharmaceutical compositions comprising a bacterial Ema polypeptide and a pharmaceutically acceptable carrier. The invention provides pharmaceutical compositions comprising a streptococcal polypeptide selected from the group of EmaA, EmaB, EmaC, EmaD and EmaE, the polypeptide of SEQ ID NO:23, the polypeptide of SEQ ID NO:26, the polypeptide of SEQ ID NO:37, and a pharmaceutically acceptable carrier. The invention provides pharmaceutical compositions comprising a streptococcal polypeptide selected from the group of EmaA, EmaB, EmaC, EmaD and EmaE, and a pharmaceutically acceptable carrier. The present invention further provides pharmaceutical compositions comprising one or more GBS Ema polypeptide, or a fragment thereof, in combination with one or more of GBS polypeptide Spb1, Spb2, C protein alpha antigen, Rib, Lmb, C5a-ase, a Group B streptococcal polysaccharide or oligosaccharide vaccine, and an anti-streptococcal vaccine.

In a still further aspect, the present invention provides a purified antibody to a streptococcal polypeptide selected from the group of EmaA, EmaB, EmaC, EmaD and EmaE. In a still further aspect, the present invention provides a purified antibody to a streptococcal polypeptide selected from the group of the polypeptide of SEQ ID NO:23, the polypeptide of SEQ ID NO:26, and the polypeptide of SEQ ID NO:37.

Antibodies against the isolated polypeptides of the present invention include naturally raised and recombinantly prepared antibodies. These may include both polyclonal and monoclonal antibodies prepared by known genetic techniques, as well as bi-specific (chimeric) antibodies, and antibodies including other functionalities suiting them for diagnostic use. Such antibodies can be used in immunoassays to diagnose infection with a particular strain or species of bacteria. The antibodies can also be used for passive immunization to treat an infection with streptococcal bacteria including Group B *streptococcus*, Group A *streptococcus*, and *S. pneumoniae*. These antibodies may also be suitable for modulating bacterial adherence and/or invasion including but not limited to acting as competitive agents.

The present invention provides a monoclonal antibody to a streptococcal polypeptide selected from the group of EmaA, EmaB, EmaC, EmaD and EmaE. The invention thereby extends to an immortal cell line that produces a monoclonal antibody to a streptococcal polypeptide selected from the group of EmaA, EmaB, EmaC, EmaD and EmaE.

An antibody to a streptococcal Ema polypeptide EmaA, EmaB, EmaC, EmaD or EmaE labeled with a detectable label is further provided. In particular embodiments, the label may selected from the group consisting of an enzyme, a chemical which fluoresces, and a radioactive element.

The present invention provides a pharmaceutical composition comprising one or more antibodies to a streptococcal protein selected from the group of EmaA, EmaB, EmaC, EmaD and EmaE, and a pharmaceutically acceptable carrier. The invention further provides a pharmaceutical composition comprising a combination of at least two antibodies to Group B streptococcal proteins and a pharmaceutically acceptable carrier, wherein at least one antibody to a protein selected from the group of EmaA, EmaB, EmaC, EmaD, and EmaE is combined with at least one antibody to a protein selected from the group of Spb1, Spb2, Rib, Lmb, C5a-ase and a C protein alpha antigen.

The present invention also relates to isolated nucleic acids, such as recombinant DNA molecules or cloned genes, or degenerate variants thereof, mutants, analogs, or fragments thereof, which encode the isolated polypeptide of the present invention or which competitively inhibit the activity of the polypeptide. The present invention further relates to isolated nucleic acids, such as recombinant DNA molecules or cloned genes, or degenerate variants thereof, mutants, analogs, or fragments thereof, which encode a bacterial Ema polypeptide. The present invention further relates to isolated nucleic acids, such as recombinant DNA molecules or cloned genes, or degenerate variants thereof, mutants, analogs, or fragments thereof, which encode a streptococcal Ema polypeptide. The present invention further relates to isolated nucleic acids, such as recombinant DNA molecules or cloned genes, or degenerate variants thereof, mutants, analogs, or fragments thereof, which encode a streptococcal Ema polypeptide, particularly selected from the group of EmaA, EmaB, EmaC, EmaD and EmaE. Preferably, the isolated nucleic acid, which includes degenerates, variants, mutants, analogs, or fragments thereof, has a sequence as set forth in SEQ ID NOS: 1, 3, 5, 7 or 9. In a further embodiment of the invention, the DNA sequence of the recombinant DNA molecule or cloned gene may be operatively linked to an expression control sequence which may be introduced into an appropriate host. The invention accordingly extends to unicellular hosts transformed with the cloned gene or recombinant DNA molecule comprising a DNA sequence encoding an Ema protein, particularly selected from the group of EmaA, EmaB, EmaC, EmaD and EmaE, and more particularly, the DNA sequences or fragments thereof determined from the sequences set forth above.

In a particular embodiment, the nucleic acid encoding the EmaA polypeptide has the sequence selected from the group comprising SEQ ID NO:1; a sequence that hybridizes to SEQ ID NO:1 under moderate stringency hybridization conditions; DNA sequences capable of encoding the amino acid sequence encoded by SEQ ID NO:1 or a sequence that hybridizes to SEQ ID NO:1 under moderate stringency hybridization conditions; degenerate variants thereof; alleles thereof; and hybridizable fragments thereof. In a particular embodiment, the nucleic acid encoding the EmaA polypeptide has the sequence selected from the group comprising SEQ ID NO:1; a sequence complementary to SEQ ID NO:1; or a homologous sequence which is substantially similar to SEQ ID NO:1. In a further embodiment, the nucleic acid has the sequence consisting of SEQ ID NO:1.

In a particular embodiment, the nucleic acid encoding the EmaB polypeptide has the sequence selected from the group comprising SEQ ID NO:3; a sequence that hybridizes to SEQ ID NO:3 under moderate stringency hybridization conditions; DNA sequences capable of encoding the amino acid sequence encoded by SEQ ID NO:3 or a sequence that hybridizes to SEQ ID NO:3 under moderate stringency hybridization conditions; degenerate variants thereof; alleles thereof; and hybridizable fragments thereof. In a particular embodiment, the nucleic acid encoding the EmaB polypeptide has the sequence selected from the group comprising SEQ ID NO:3; a sequence complementary to SEQ ID NO:3; or a homologous sequence which is substantially similar to SEQ ID NO:3. In a further embodiment, the nucleic acid has the sequence consisting of SEQ ID NO:3.

In a particular embodiment, the nucleic acid encoding the EmaC polypeptide has the sequence selected from the group comprising SEQ ID NO:5; a sequence that hybridizes to SEQ ID NO:5 under moderate stringency hybridization conditions; DNA sequences capable of encoding the amino acid sequence encoded by SEQ ID NO:5 or a sequence that hybridizes to SEQ ID NO:5 under moderate stringency hybridization conditions; degenerate variants thereof; alleles thereof; and hybridizable fragments thereof. In a particular embodiment, the nucleic acid encoding the EmaC polypeptide has the sequence selected from the group comprising SEQ ID NO:5; a sequence complementary to SEQ ID NO:5; or a homologous sequence which is substantially similar to SEQ ID NO:5. In a further embodiment, the nucleic acid has the sequence consisting of SEQ ID NO:5.

In a particular embodiment, the nucleic acid encoding the EmaD polypeptide has the sequence selected from the group comprising SEQ ID NO:7; a sequence that hybridizes to SEQ ID NO:7 under moderate stringency hybridization conditions; DNA sequences capable of encoding the amino acid sequence encoded by SEQ ID NO:7 or a sequence that hybridizes to SEQ ID NO:7 under moderate stringency hybridization conditions; degenerate variants thereof; alleles thereof; and hybridizable fragments thereof. In a particular embodiment, the nucleic acid encoding the EmaD polypeptide has the sequence selected from the group comprising SEQ ID NO:7; a sequence complementary to SEQ ID NO:7; or a homologous sequence which is substantially similar to SEQ ID NO:7. In a further embodiment, the nucleic acid has the sequence consisting of SEQ ID NO:7.

In a particular embodiment, the nucleic acid encoding the EmaE polypeptide has the sequence selected from the group comprising SEQ ID NO:9; a sequence that hybridizes to SEQ ID NO:9 under moderate stringency hybridization conditions; DNA sequences capable of encoding the amino acid sequence encoded by SEQ ID NO:9 or a sequence that hybridizes to SEQ ID NO:9 under moderate stringency hybridization conditions; degenerate variants thereof, alleles thereof; and hybridizable fragments thereof. In a particular embodiment, the nucleic acid encoding the EmaE polypeptide has the sequence selected from the group comprising SEQ ID NO:9; a sequence complementary to SEQ ID NO:9; or a homologous sequence which is substantially similar to SEQ ID NO:9 In a further embodiment, the nucleic acid has the sequence consisting of SEQ ID NO:9.

In a further embodiment, the nucleic acid encoding the bacterial Ema polypeptide comprises the sequence selected from the group comprising SEQ ID NO: 24, 27, 30 and 33. In a further embodiment, the nucleic acid encoding the bacterial Ema polypeptide has the sequence selected from the group comprising SEQ ID NO: 24, 27, 30 and 33.

A nucleic acid capable of encoding a streptococcal polypeptide EmaA, EmaB, EmaC, EmaD or EmaE which is a recombinant DNA molecule is further provided. Such a recombinant DNA molecule wherein the DNA molecule is operatively linked to an expression control sequence is also provided herein.

The present invention relates to nucleic acid vaccines or DNA vaccines comprising nucleic acids encoding immunogenic streptococcal Ema polypeptides, particularly selected from the group of EmaA, EmaB, EmaC, EmaD and EmaE. The present invention relates to nucleic acid vaccines or DNA vaccines comprising nucleic acids encoding one or more immunogenic Ema polypeptide or a fragment thereof or any combination of one or more Ema polypeptide EmaA, EmaB, EmaC, EmaD or EmaE with at least one other polypeptide, particularly a GBS polypeptide, more particularly wherein said other GBS polypeptide is selected from the group of Spb1, Spb2, C protein alpha antigen, Rib, Lmb, C5a-ase, and immunogenic polypeptide fragments thereof.

The invention further relates to a vaccine for protection of an animal subject from infection with a streptococcal bacterium comprising a vector containing a gene encoding an Ema polypeptide selected from the group of EmaA, EmaB, EmaC, EmaD and EmaE operatively associated with a promoter capable of directing expression of the gene in the subject. The present invention further provides a nucleic acid vaccine comprising a recombinant DNA molecule capable of encoding a GBS polypeptide EmaA, EmaB, EmaC, EmaD or EmaE.

The invention further relates to a vaccine for protection of an animal subject from infection with a Group B streptococcal bacterium comprising a vector containing a gene encoding an Ema polypeptide selected from the group of EmaA, EmaB, EmaC, EmaD and EmaE operatively associated with a promoter capable of directing expression of the gene in the subject. The present invention further provides a nucleic acid vaccine comprising a recombinant DNA molecule capable of encoding a GBS polypeptide EmaA, EmaB, EmaC, EmaD or EmaE.

The present invention provides a vector which comprises the nucleic acid capable of encoding an Ema polypeptide selected from the group of EmaA, EmaB, EmaC, EmaD and EmaE and a promoter. The present invention provides a vector which comprises the nucleic acid of any of SEQ ID NO: 1, 3, 5, 7 or 9 and a promoter. The invention contemplates a vector wherein the promoter comprises a bacterial, yeast, insect or mammalian promoter. The invention contemplates a vector wherein the vector is a plasmid, cosmid, yeast artificial chromosome (YAC), bacteriophage or eukaryotic viral DNA.

The present invention further provides a host vector system for the production of a polypeptide which comprises the vector capable of encoding an Ema polypeptide, particularly selected from the group of EmaA, EmaB, EmaC, EmaD and EmaE in a suitable host cell. A host vector system is provided wherein the suitable host cell comprises a prokaryotic or eukaryotic cell. A unicellular host transformed with a recombinant DNA molecule or vector capable of encoding an Ema polypeptide selected from the group of EmaA, EmaB, EmaC, EmaD and EmaE is thereby provided.

The present invention includes methods for determining and monitoring infection by streptococci by detecting the presence of a streptococcal polypeptide selected from the group of EmaA, EmaB, EmaC, EmaD and EmaE. In a particular such method, the streptococcal Ema polypeptide is measured by:

a. contacting a sample in which the presence or activity of a Streptococcal polypeptide selected from the group of EmaA, EmaB, EmaC, EmaD and EmaE is suspected with an antibody to the said streptococcal polypeptide under conditions that allow binding of the streptococcal polypeptide to the antibody to occur; and b. detecting whether binding has occurred between the streptococcal polypeptide from the sample and the antibody; wherein the detection of binding indicates the presence or activity of the streptococcal polypeptide in the sample.

The present invention includes methods for determining and monitoring infection by streptococci by detecting the presence of a streptococcal polypeptide selected from the group of EmaA, EmaB, EmaC, EmaD and EmaE. In a particular such method, the streptococcal Ema polypeptide is measured by:

a. contacting a sample in which the presence or activity of a Streptococcal polypeptide selected from the group of EmaA, EmaB, EmaC, EmaD and EmaE is suspected with an antibody to the said streptococcal polypeptide under conditions that allow binding of the streptococcal polypeptide to the antibody to occur; and b. detecting whether binding has occurred between the streptococcal polypeptide from the sample and the antibody; wherein the detection of binding indicates the presence or activity of the streptococcal polypeptide in the sample.

The present invention includes methods for determining and monitoring infection by Group streptococci by detecting the presence of a Group B streptococcal polypeptide selected from the group of EmaA, EmaB, EmaC, EmaD and EmaE. In a particular such method, the streptococcal Ema polypeptide is measured by:

a. contacting a sample in which the presence or activity of a Group B streptococcal polypeptide selected from the group of EmaA, EmaB, EmaC, EmaD and EmaE is suspected with an antibody to the said Group B streptococcal polypeptide under conditions that allow binding of the Group B streptococcal polypeptide to the antibody to occur; and b. detecting whether binding has occurred between the Group B streptococcal polypeptide from the sample and the antibody; wherein the detection of binding indicates the presence or activity of the Group B streptococcal polypeptide in the sample.

The present invention further provides a method for detecting the presence of a bacterium having a gene encoding a streptococcal polypeptide selected from the group of emaA, emaB, emaC, emaD and emaE, comprising:

a. contacting a sample in which the presence or activity of the bacterium is suspected with an oligonucleotide which hybridizes to a streptococcal polypeptide gene selected from the group of emaA, emaB, emaC, emaD and emaE, under conditions that allow specific hybridization of the oligonucleotide to the gene to occur; and b. detecting whether hybridization has occurred between the oligonucleotide and the gene; wherein the detection of hybridization indicates that presence or activity of the bacterium in the sample.

The invention includes an assay system for screening of potential compounds effective to modulate the activity of a streptococcal protein EmaA, EmaB, EmaC, EmaD or EmaE of the present invention. In one instance, the test compound, or an extract containing the compound, could be administered to a cellular sample expressing the particular Ema protein to determine the compound's effect upon the activity of the protein by comparison with a control. In a further instance the test compound, or an extract containing the compound, could be administered to a cellular sample expressing the Ema protein to determine the compound's effect upon the activity of the protein, and thereby on adherence of said cellular sample to host cells, by comparison with a control.

It is still a further object of the present invention to provide a method for the prevention or treatment of mammals to control the amount or activity of streptococci, so as to treat or prevent the adverse consequences of invasive, spontaneous, or idiopathic pathological states.

It is still a further object of the present invention to provide a method for the prevention or treatment of mammals to control the amount or activity of Group B streptococci, so as to treat or prevent the adverse consequences of invasive, spontaneous, or idiopathic pathological states.

The invention provides a method for preventing infection with a bacterium that expresses a streptococcal Ema polypeptide comprising administering an immunogenically effective dose of a vaccine comprising an Ema polypeptide selected from the group of EmaA, EmaB, EmaC, EmaD and EmaE to a subject.

The invention further provides a method for preventing infection with a bacterium that expresses a Group B streptococcal Ema polypeptide comprising administering an immunogenically effective dose of a vaccine comprising an Ema polypeptide selected from the group of EmaA, EmaB, EmaC, EmaD and EmaE to a subject.

The present invention is directed to a method for treating infection with a bacterium that expresses a streptococcal Ema polypeptide comprising administering a therapeutically effective dose of a pharmaceutical composition comprising an Ema polypeptide selected from the group of EmaA, EmaB, EmaC, EmaD and EmaE, and a pharmaceutically acceptable carrier to a subject.

The invention further provides a method for treating infection with a bacterium that expresses a streptococcal Ema polypeptide comprising administering a therapeutically effective dose of a pharmaceutical composition comprising an antibody to an Ema polypeptide selected from the group of EmaA, EmaB, EmaC, EmaD and EmaE, and a pharmaceutically acceptable carrier to a subject.

In a further aspect, the invention provides a method of inducing an immune response in a subject which has been exposed to or infected with a streptococcal bacterium comprising administering to the subject an amount of the pharmaceutical composition comprising an Ema polypeptide selected from the group of EmaA, EmaB, EmaC, EmaD and EmaE, and a pharmaceutically acceptable carrier, thereby inducing an immune response.

The invention still further provides a method for preventing infection by a streptococcal bacterium in a subject comprising administering to the subject an amount of a pharmaceutical composition comprising an antibody to an Ema polypeptide selected from the group of EmaA, EmaB, EmaC, EmaD and EmaE and a pharmaceutically acceptable carrier or diluent, thereby preventing infection by a streptococcal bacterium.

In a further aspect, the invention provides a method of inducing an immune response in a subject which has been exposed to or infected with a Group B streptococcal bacterium comprising administering to the subject an amount of the pharmaceutical composition comprising an Ema polypeptide selected from the group of EmaA, EmaB, EmaC, EmaD and EmaE, and a pharmaceutically acceptable carrier, thereby inducing an immune response.

The invention still further provides a method for preventing infection by a Group B streptococcal bacterium in a subject comprising administering to the subject an amount of a pharmaceutical composition comprising an antibody to an Ema polypeptide selected from the group of EmaA, EmaB, EmaC, EmaD and EmaE and a pharmaceutically acceptable carrier or diluent, thereby preventing infection by a streptococcal bacterium.

The invention further provides an ema mutant bacteria which is non-adherent and/or non-invasive to cells, particularly which is mutated in one or more genes selected from the group of emaA, emaB, emaC, emaD and emaE. Particularly, such ema mutant is a streptococcal bacteria. More particularly, such ema mutant is a Group B streptococcal bacteria. Such non-adherent and/or non-invasive ema mutant bacteria can further be utilized in expressing other immunogenic or therapeutic proteins for the purposes of eliciting immune responses to any such other proteins in the context of vaccines and in other forms of therapy.

Other objects and advantages will become apparent to those skilled in the art from a review of the following description which proceeds with reference to the following illustrative drawings.

BRIEF DESCRIPTION OF THE DRAWINGS

FIG. 3). The same pattern of hybridization was observed using probe DY1-11.

FIG. 2 depicts the nucleic acid (SEQ ID NO:1) and predicted amino acid (SEQ ID NO:2) sequence of emaA.

FIGS. 3A and 3B depict the nucleic acid (SEQ ID NO:3) and predicted amino acid (SEQ ID NO:4) sequence of emaB.

FIG. 4 depicts the nucleic acid (SEQ ID NO:5) and predicted amino acid (SEQ ID NO:6) sequence of emaC.

FIG. 5 depicts the nucleic acid (SEQ ID NO:7) and predicted amino acid (SEQ ID NO:8) sequence of emaD.

FIGS. 6A-D depict the nucleic acid (SEQ ID NO:9) and predicted amino acid (SEQ ID NO:10) sequence of emaE.

DETAILED DESCRIPTION

Figure 1:
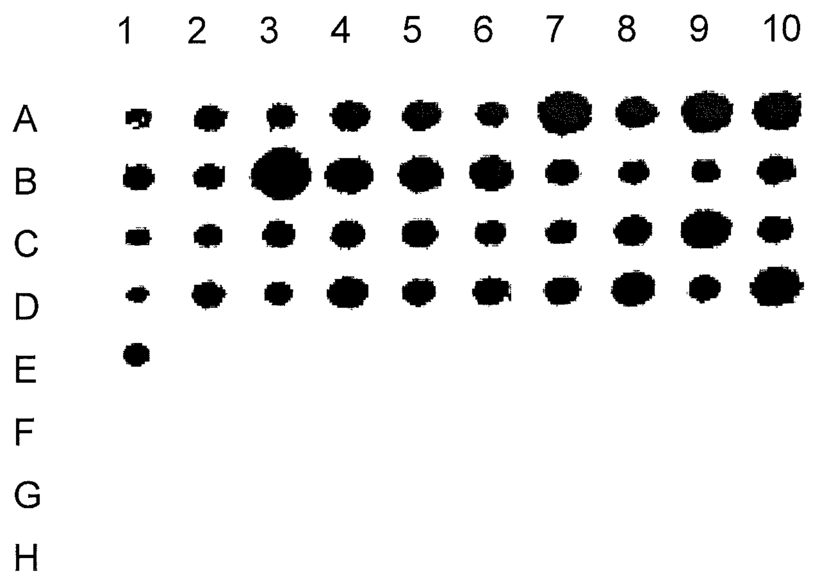
FIG. 1 depicts the restriction digest pattern (RDP) type III-3 specific probes. Dot blot hybridization of probe DY1-1 with genomic DNA isolated from type III GBS. 10 ug of genomic DNA from each of 62 type III GBS strains was transferred to nylon membrane. Radiolabeled probe DY1-1 hybridized with DNA from all III-3 strains (rows A-D) including the original type III-3 strain (well E-1). The probe failed to hybridize with DNA from III-2 strains (F1-F10, G1-7) including the original strain used in the subtraction hybridization (well E10) and III-1 strains (wells H1-3; cf.

The present invention provides novel Group B streptococcal Ema polypeptides and their Ema homologs in distinct bacterial species, including distinct streptococcal species. The present invention relates to novel streptococcal Ema polypeptides, particularly selected from the group of EmaA, EmaB, EmaC, EmaD and EmaE, and fragments thereof. Nucleic acids encoding Ema polypeptides, and diagnostic and therapeutic compositions and methods based thereon for identification and prevention of infections by virulent forms of streptococci are provided. In particular, the present invention includes Group B streptococcal Ema polypeptides. The invention further includes polypeptide homologs of the GBS Ema polypeptides, particularly streptococcal homologs, more particularly Ema homologs of *S. pneumoniae* and *S. pyogenes*. Bacterial Ema polypeptide homologs in *E. faecalis* and *C. diptheriae* are also provided.

Polypeptides

The present invention is directed to an isolated polypeptide comprising an amino acid sequence of a bacterial Ema polypeptide. Bacterial Ema polypeptides are provided from *streptococcus, enterococcus* and *corynebacterium*. The present invention is particularly directed to an isolated polypeptide comprising an amino acid sequence of a streptococcal Ema polypeptide selected from the group of EmaA, EmaB, EmaC, EmaD and EmaE. The present invention is particularly directed to an isolated polypeptide comprising an amino acid sequence of a Group streptococcal Ema polypeptide selected from the group of EmaA, EmaB, EmaC, EmaD and EmaE. Additional *S. pneumoniae* and *S. pyogenes* Ema polypeptides are included in the invention. *E. faecalis* and *C. diptheriae* Ema polypeptides are also included in the invention.

The polypeptides of the present invention are suitable for use in immunizing animals broadly against streptococcal infection. The polypeptides of the present invention are suitable for use in immunizing animals broadly against Group B, Group A, and *S. pneumoniae* streptococcal infection. The polypeptides of the present invention are suitable for use in immunizing animals against Group B streptococci. These polypeptide or peptide fragments thereof, when formulated with an appropriate adjuvant, are used in vaccines for protection against streptococci, particularly Group B streptococci, and against other bacteria with cross-reactive proteins.

GBS proteins with streptococcal homologs outside of Group B have been previously identified (Lachenauer C S and Madoff L C (1997) Adv Exp Med. Biol. 418:615-8; Brady L. J. et al (1991) Infect Immun 59(12):4425-35; Stahlhammer-Carlemalm M. et al (2000) J Infect Dis 182(1):142-129). Stahlhammer-Carlemalm et al have demonstrated cross-protection between Group A and Group B streptococci due to cross-reacting surface proteins (Stahlhammer-Carlemalm M. et al (2000) J Infect Dis 182(1):142-129). The R28 protein of group A *streptococcus* (GAS) and the Rib protein of group B *streptococcus* (GBS) are surface molecules that elicit protective immunity to experimental infection. These proteins are members of the same family and cross-react immunologically. In spite of extensive amino acid residue identity, the cross-reactivity between R28 and Rib was found to be limited, as shown by analysis with highly purified proteins and specific antisera. Nevertheless, immunization of mice with purified R28 conferred protection against lethal infection with Rib-expressing GBS strains, and immunization with Rib conferred protection against R28-expressing GAS. Thus, R28 and Rib elicited cross-protective immunity.

The present invention is directed to an isolated streptococcal EmaA polypeptide which comprises the amino acid sequence set out in SEQ ID NO:2, and analogs, variants and immunogenic fragments thereof.

The present invention is directed to an isolated streptococcal EmaB polypeptide which comprises the amino acid sequence set out in SEQ ID NO:4, and analogs, variants and immunogenic fragments thereof.

The present invention is directed to an isolated streptococcal EmaC polypeptide which comprises the amino acid sequence set out in SEQ ID NO:6, and analogs, variants and immunogenic fragments thereof.

The present invention is directed to an isolated streptococcal EmaD polypeptide which comprises the amino acid sequence set out in SEQ ID NO:8, and analogs, variants and immunogenic fragments thereof.

The identity or location of one or more amino acid residues may be changed or modified to include variants such as, for example, deletions containing less than all of the residues specified for the protein, substitutions wherein one or more residues specified are replaced by other residues and additions wherein one or more amino acid residues are added to a terminal or medial portion of the polypeptide. These molecules include: the incorporation of codons “preferred” for expression by selected non-mammalian hosts; the provision of sites for cleavage by restriction endonuclease enzymes; and the provision of additional initial, terminal or intermediate DNA sequences that facilitate construction of readily expressed vectors.

The present invention is directed to an isolated Group B streptococcal EmaE polypeptide which comprises the amino acid sequence set out in SEQ ID NO:10, and analogs, variants and immunogenic fragments thereof.

The present invention thus provides an isolated streptococcal Ema polypeptide comprising the amino acid sequence, set out in SEQ ID NO:23. An isolated nucleic acid which encodes the streptococcal polypeptide set out in SEQ ID NO:23 is further provided.

The invention thus further provides an isolated streptococcal Ema polypeptide comprising the amino acid sequence set out in SEQ ID NO:26. An isolated nucleic acid which encodes the streptococcal polypeptide set out in SEQ ID NO:26 is further provided.

The present invention further provides an isolated streptococcal Ema polypeptide comprising the amino acid sequence set out in SEQ ID NO:37. An isolated nucleic acid which encodes the streptococcal polypeptide set out in SEQ ID NO:37 is further provided.

An enterococcal Ema polypeptide is further provided comprising the amino acid sequence set out in SEQ ID NO:29. An isolated nucleic acid which encodes the enterococcal polypeptide set out in SEQ ID NO:29 is also provided.

The invention provides an isolated *Corynebacterium* Ema polypeptide comprising the amino acid sequence set out in SEQ ID NO:32. Also provided is an isolated nucleic acid which encodes the *Corynebacterium* polypeptide set out in SEQ ID NO:32.

The invention provides an isolated bacterial polypeptide comprising the amino acid sequence TLLTCTPYMINS/THRLLVR/KG (SEQ ID NO:34), wherein the polypeptide is not isolated from *Actinomyces*.

The invention further provides an isolated streptococcal polypeptide comprising the amino acid sequence TLLTCTPYMINS/THRLLVR/KG (SEQ ID NO:34).

Also provided is an isolated bacterial polypeptide comprising the amino acid sequence TLVTCTPYGINTHRLLVTA (SEQ ID NO:35).

The present invention includes an isolated bacterial polypeptide comprising the amino acid sequence TLVTCTPYGVNTKRLLVRG (SEQ ID NO:36). An isolated streptococcal polypeptide comprising the amino acid sequence TLVTCTPYGVNTKRLLVRG (SEQ ID NO:36) is also provided.

The invention further includes an isolated polypeptide having the amino acid sequence selected from the group of TLLTCTPYMNS/TH LLVRIKG (SEQ ID NO:34), TLVTCTPYGINTHRLLVTA (SEQ ID NO:35), and TLVTCTPYGVNTKRLLVRG (SEQ ID NO:36).

The present invention contemplates the use of the streptococcal polypeptides of the present invention in diagnostic tests and methods for determining and/or monitoring of streptococcal infection. Thus, the present invention provides an isolated GBS Ema polypeptide, particularly selected from the group of EmaA, EmaB, EmaC, EmaD and EmaE, labeled with a detectable label.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectro-photometric, amperometric or gasometric techniques known in the art.

The present invention extends to an immunogenic bacterial Ema polypeptide. The present invention extends to an immunogenic streptococcal Ema polypeptide, particularly selected from the group of EmaA, EmaB, EmaC, EmaD and EmaE, or a fragment thereof. The present invention also extends to immunogenic GBS Ema polypeptides wherein such polypeptides comprise a combination of at least one immunogenic GBS Ema polypeptide, selected from the group of EmaA, EmaB, EmaC, EmaD and EmaE, or immunogenic polypeptide fragment thereof and GBS polypeptide Spb1, Spb2, C protein alpha antigen, Rib or immunogenic fragments thereof.

As defined herein, "adhesion" means noncovalent binding of a bacteria to a human cell or secretion that is stable enough to withstand washing.

The term "extracellular matrix adhesin", "Ema", "ema" and any variants not specifically listed, may be used herein interchangeably, and as used throughout the present application and claims refer to proteinaceous material including single or multiple proteins, and extends to those proteins having the amino acid sequence data described herein and particularly identified by (SEQ ID NOS: 2, 4, 6, 8, 10, 23, 26, 29, 32 and 37), and the profile of activities set forth herein and in the Claims. In particular the Ema proteins provided herein include EmaA, EmaB, EmaC, EmaD and EmaE. The Ema proteins include bacterial Ema homologs. Bacterial Ema homologs include those from streptococcal species and other bacterial species. Accordingly, proteins and polypeptides displaying substantially equivalent or altered activity are likewise contemplated. These modifications may be deliberate, for example, such as modifications obtained through site-directed mutagenesis, or may be accidental, such as those obtained through mutations in hosts that are producers of one or more Ema polypeptide. Also, the term "extracellular matrix adhesin (Ema)" is intended to include within its scope proteins specifically recited herein as well as all substantially homologous analogs and allelic variations.

This invention provides an isolated immunogenic polypeptide comprising an amino acid sequence of a bacterial Ema polypeptide. This invention provides an isolated immunogenic polypeptide comprising an amino acid sequence of a streptococcal Ema polypeptide, particularly selected from the group of EmaA, EmaB, EmaC, EmaD and EmaE. It is contemplated by this invention that the immunogenic polypeptide has the amino acid sequence set forth in any of SEQ ID NOS: 2, 4, 6, 8, 10, 23, 26, 29, 32 and 37, including immunogenic fragments, mutants, variants, analogs, or derivatives, thereof.

This invention is directed to analogs of the polypeptide which comprise the amino acid sequence as set forth above. The analog polypeptide may have an N-terminal methionine or a polyhistidine optionally attached to the N or COOH terminus of the polypeptide which comprise the amino acid sequence.

In another embodiment, this invention contemplates peptide fragments of the polypeptide which result from proteolytic digestion products of the polypeptide. In another embodiment, the derivative of the polypeptide has one or more chemical moieties attached thereto. In another embodiment the chemical moiety is a water soluble polymer. In another embodiment the chemical moiety is polyethylene glycol. In another embodiment the chemical moiety is mono-, di-, tri- or tetrapegylated. In another embodiment the chemical moiety is N-terminal monopegylated.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention may be delivered in a microencapsulation device so as to reduce or prevent an host immune response against the compound or against cells which may produce the compound. The compound of the present invention may also be delivered microencapsulated in a membrane, such as a liposome. Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

In one embodiment, the amino acid residues of the polypeptide described herein are preferred to be in the "L" isomeric form. In another embodiment, the residues in the "D" isomeric form can be substituted for any L-amino acid residue, as long as the desired functional property of lectin activity is retained by the polypeptide. $NH_2$ refers to the free amino group present at the amino terminus of a polypeptide. COOH refers to the free carboxy group present at the carboxy terminus of a polypeptide. Abbreviations used herein are in keeping with standard polypeptide nomenclature, J. Biol. Chem., 243:3552-59 (1969).

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

Synthetic polypeptide, prepared using the well known techniques of solid phase, liquid phase, or peptide condensation techniques, or any combination thereof, can include natural and unnatural amino acids. Amino acids used for peptide synthesis may be standard Boc ($N^{\alpha}$-amino protected $N^{\alpha}$-t-butyloxycarbonyl) amino acid resin with the standard deprotecting, neutralization, coupling and wash protocols of the original solid phase procedure of Merrifield (1963, J. Am. Chem. Soc. 85:2149-2154), or the base-labile $N^{\alpha}$-amino protected 9-fluorenylmethoxycarbonyl (Fmoc) amino acids first described by Carpino and Han (1972, J. Org. Chem. 37:3403-3409). Thus, polypeptide of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In one aspect of the invention, the peptides may comprise a special amino acid at the C-terminus which incorporates either a $CO_2H$ or $CONH_2$ side chain to simulate a free glycine or a glycine-amide group. Another way to consider this special residue would be as a D or L amino acid analog with a side chain consisting of the linker or bond to the bead. In one embodiment, the pseudo-free C-terminal residue may be of the D or the L optical configuration; in another embodiment, a racemic mixture of D and L-isomers may be used.

In an additional embodiment, pyroglutamate may be included as the N-terminal residue of the peptide. Although pyroglutamate is not amenable to sequence by Edman degradation, by limiting substitution to only 50% of the peptides on a given bead with N-terminal pyroglutamate, there will remain enough non-pyroglutamate peptide on the bead for sequencing. One of ordinary skill would readily recognize that this technique could be used for sequencing of any peptide that incorporates a residue resistant to Edman degradation at the N-terminus. Other methods to characterize individual peptides that demonstrate desired activity are described in detail infra. Specific activity of a peptide that comprises a blocked N-terminal group, e.g., pyroglutamate, when the particular N-terminal group is present in 50% of the peptides, would readily be demonstrated by comparing activity of a completely (100%) blocked peptide with a non-blocked (0%) peptide.

In addition, the present invention envisions preparing peptides that have more well defined structural properties, and the use of peptidomimetics, and peptidornimetic bonds, such as ester bonds, to prepare peptides with novel properties. In another embodiment, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a molecule would be resistant to peptide bond hydrolysis, e.g., protease activity. Such peptides would provide ligands with unique function and activity, such as extended half-lives in vivo due to resistance to metabolic breakdown, or protease activity. Furthermore, it is well known that in certain systems constrained peptides show enhanced functional activity (Hruby, 1982, Life Sciences 31:189-199; Hruby et al., 1990, Biochem J. 268:249-262); the present invention provides a method to produce a constrained peptide that incorporates random sequences at all other positions.

A constrained, cyclic or rigidized peptide may be prepared synthetically, provided that in at least two positions in the sequence of the peptide an amino acid or amino acid analog is inserted that provides a chemical functional group capable of cross-linking to constrain, cyclize or rigidize the peptide after treatment to form the cross-link. Cyclization will be favored when a turn-inducing amino acid is incorporated. Examples of amino acids capable of cross-linking a peptide are cysteine to form disulfide, aspartic acid to form a lactone or a lactase, and a chelator such as γ-carboxyl-glutamic acid (Gla) (Bachem) to chelate a transition metal and form a cross-link. Protected γ-carboxyl-glutamic acid may be prepared by modifying the synthesis described by Zee-Cheng and Olson (1980, Biophys. Biochem. Res. Commun. 94:1128-1132). A peptide in which the peptide sequence comprises at least two amino acids capable of cross-linking may be treated, e.g., by oxidation of cysteine residues to form a disulfide or addition of a metal ion to form a chelate, so as to cross-link the peptide and form a constrained, cyclic or rigidized peptide.

The present invention provides strategies to systematically prepare cross-links. For example, if four cysteine residues are incorporated in the peptide sequence, different protecting groups may be used (Hiskey, 1981, in The Peptides: Analysis, Synthesis, Biology, Vol. 3, Gross and Meienhofer, eds., Academic Press: New York, pp. 137-167; Ponsanti et al., 1990, Tetrahedron 46:8255-8266). The first pair of cysteine may be deprotected and oxidized, then the second set may be deprotected and oxidized. In this way a defined set of disulfide cross-links may be formed. Alternatively, a pair of cysteine and a pair of collating amino acid analogs may be incorporated so that the cross-links are of a different chemical nature.

The following non-classical amino acids may be incorporated in the peptide in order to introduce particular conformational motifs: 1,2,3,4-tetrahydroisoquinoline-3-carboxylate (Kazmierski et al., 1991, J. Am. Chem. Soc. 113:2275-2283); (2S,3S)-methyl-phenylalanine, (2S,3R)-methyl-phenylalanine, (2R,3S)-methyl-phenylalanine and (2R,3R)-methyl-phenylalanine (Kazmierski and Hruby, 1991, Tetrahedron Lett.); 2-aminotetrahydronaphthalene-2-carboxylic acid (Landis, 1989, Ph.D. Thesis, University of Arizona); hydroxy-1,2,3,4-tetrahydroisoquinoline-3-carboxylate (Miyake et al., 1989, J. Takeda Res. Labs. 43:53-76); β-carboline (D and L) (Kazmierski, 1988, Ph.D. Thesis, University of Arizona); HIC (histidine isoquinoline carboxylic acid) (Zechel et al., 1991, Int. J. Pep. Protein Res. 43); and HIC (histidine cyclic urea) (Dharanipragada).

The following amino acid analogs and peptidomimetics may be incorporated into a peptide to induce or favor specific secondary structures: LL-Acp (LL-3-amino-2-propenidone-6-carboxylic acid), a β-turn inducing dipeptide analog (Kemp et al., 1985, J. Org. Chem. 50:5834-5838); β-sheet inducing analogs (Kemp et al., 1988, Tetrahedron Lett. 29:5081-5082); β-turn inducing analogs (Kemp et al., 1988, Tetrahedron Lett. 29:5057-5060); helix inducing analogs (Kemp et al., 1988, Tetrahedron Lett. 29:4935-4938); γ-turn inducing analogs (Kemp et al., 1989, J. Org. Chem. 54:109:115); and analogs provided by the following references: Nagai and Sato, 1985, Tetrahedron Lett. 26:647-650; DiMaio et al., 1989, J. Chem. Soc. Perkin Trans. p. 1687; also a Gly-Ala turn analog (Kahn et al., 1989, Tetrahedron Lett. 30:2317); amide bond isostere (Jones et al., 1988, Tetrahedron Lett. 29:3853-3856); tetrazol (Zabrocki et al., 1988, J. Am. Chem. Soc. 110:5875-5880); DTC (Samanen et al., 1990, Int. J. Protein Pep. Res. 35:501: 509); and analogs taught in Olson et al., 1990, J. Am. Chem. Sci. 112:323-333 and Garvey et al., 1990, J. Org. Chem. 56:436. Conformationally restricted mimetics of beta turns and beta bulges, and peptides containing them, are described in U.S. Pat. No. 5,440,013, issued Aug. 8, 1995 to Kahn.

The present invention further provides for modification or derivatization of the polypeptide or peptide of the invention. Modifications of peptides are well known to one of ordinary skill, and include phosphorylation, carboxymethylation, and acylation. Modifications may be effected by chemical or enzymatic means. In another aspect, glycosylated or fatty acylated peptide derivatives may be prepared. Preparation of glycosylated or fatty acylated peptides is well known in the art. Fatty acyl peptide derivatives may also be prepared. For example, and not by way of limitation, a free amino group (N-terminal or lysyl) may be acylated, e.g., myristoylated. In another embodiment an amino acid comprising an aliphatic side chain of the structure $—(CH_2)_nCH_3$ may be incorporated in the peptide. This and other peptide-fatty acid conjugates suitable for use in the present invention are disclosed in U.K. Patent GB-8809162.4, International Patent Application PCT/AU89/00166, and reference 5, supra.

Chemical Moieties For Derivatization. Chemical moieties suitable for derivatization may be selected from among water soluble polymers. The polymer selected should be water soluble so that the component to which it is attached does not precipitate in an aqueous environment, such as a physiological environment. Preferably, for therapeutic use of the end-product preparation, the polymer will be pharmaceutically acceptable. One skilled in the art will be able to select the desired polymer based on such considerations as whether the polymer/component conjugate will be used therapeutically, and if so, the desired dosage, circulation time, resistance to proteolysis, and other considerations. For the present component or components, these may be ascertained using the assays provided herein.

The water soluble polymer may be selected from the group consisting of, for example, polyethylene glycol, copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols and polyvinyl alcohol. Polyethylene glycol propionaldenhyde may have advantages in manufacturing due to its stability in water.

The polymer may be of any molecular weight, and may be branched or unbranched. For polyethylene glycol, the preferred molecular weight is between about 2 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The number of polymer molecules so attached may vary, and one skilled in the art will be able to ascertain the effect on function. One may mono-derivative, or may provide for a di-, tri-, tetra- or some combination of derivatization, with the same or different chemical moieties (e.g., polymers, such as different weights of polyethylene glycols). The proportion of polymer molecules to component or components molecules will vary, as will their concentrations in the reaction mixture. In general, the optimum ratio (in terms of efficiency of reaction in that there is no excess unreacted component or components and polymer) will be determined by factors such as the desired degree of derivatization (e.g., mono, di-, tri-, etc.), the molecular weight of the polymer selected, whether the polymer is branched or unbranched, and the reaction conditions.

The polyethylene glycol molecules (or other chemical moieties) should be attached to the component or components with consideration of effects on functional or antigenic domains of the protein. There are a number of attachment methods available to those skilled in the art, e.g., EP 0 401 384 herein incorporated by reference (coupling PEG to G-CSF), see also Malik et al., 1992, Exp. Hematol. 20:1028-1035 (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group include lysine residues and the—terminal amino acid residues; those having a free carboxyl group include aspartic acid residues glutamic acid residues and the C-terminal amino acid residue. Sulfhydryl groups may also be used as a reactive group for attaching the polyethylene glycol molecule(s). Preferred for therapeutic purposes is attachment at an amino group, such as attachment at the N-terminus or lysine group.

Nucleic Acids

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Mutations can be made in a nucleic acid encoding the polypeptide of the present invention such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free—OH can be maintained; and

Gln for Asn such that a free $NH_2$ can be maintained.

Synthetic DNA sequences allow convenient construction of genes which will express analogs or "muteins". A general method for site-specific incorporation of unnatural amino acids into proteins is described in Noren, et al. Science, 244: 182-188 (April 1989). This method may be used to create analogs with unnatural amino acids.

This invention provides an isolated nucleic acid encoding a polypeptide comprising an amino acid sequence of a streptococcal Ema polypeptide. This invention provides an isolated nucleic acid encoding a polypeptide comprising an amino acid sequence of a streptococcal Ema polypeptide. This invention provides an isolated nucleic acid encoding a polypeptide comprising an amino acid sequence of a Group B streptococcal Ema polypeptide selected from the group of EmaA, EmaB, EmaC, EmaD and EmaE. This invention provides an isolated nucleic acid encoding a polypeptide comprising an amino acid sequence of a Group B streptococcal Ema protein selected from the group of Ema proteins EmA, EmaB, EmaC. EmaD and EmaE as set forth in FIGS. 2-6. The invention provides an isolated nucleic acid encoding a polypeptide comprising an amino acid sequence of a bacterial Ema polypeptide selected from the group of SEQ ID NO: 23, 26, 29, 32 and 37. In particular embodiments the nucleic acid is set forth in any of SEQ ID NOS: 1, 3, 5, 7, 9, 24, 27, 30, and 33, including fragments, mutants, variants, analogs, or derivatives, thereof. The nucleic acid is DNA, cDNA, genomic DNA, RNA. Further, the isolated nucleic acid may be operatively linked to a promoter of RNA transcription.

The present invention also relates to isolated nucleic acids, such as recombinant DNA molecules or cloned genes, or degenerate variants thereof, mutants, analogs, or fragments thereof, which encode the isolated polypeptide or which competitively inhibit the activity of the polypeptide. The present invention further relates to isolated nucleic acids, such as recombinant DNA molecules or cloned genes, or degenerate variants thereof, mutants, analogs, or fragments thereof, which encode a GBS Ema polypeptide, particularly selected from the group of EmaA, EmaB, EmaC, EmaD and EmaE. Preferably, the isolated nucleic acid, which includes degenerates, variants, mutants, analogs, or fragments thereof, has a sequence as set forth in SEQ ID NOS:1, 3, 5, 7 or 9. In a further embodiment of the invention, the DNA sequence of the recombinant DNA molecule or cloned gene may be operatively linked to an expression control sequence which may be introduced into an appropriate host. The invention accordingly extends to unicellular hosts transformed with the cloned gene or recombinant DNA molecule comprising a DNA sequence encoding an Ema protein, particularly selected from the group of EmaA, EmaB, EmaC, EmaD and EmaE, and more particularly, the DNA sequences or fragments thereof determined from the sequences set forth above.

In a particular embodiment, the nucleic acid encoding the EmaA polypeptide has the sequence selected from the group comprising SEQ ID NO:1; a sequence that hybridizes to SEQ ID NO:1 under moderate stringency hybridization conditions; DNA sequences capable of encoding the amino acid sequence encoded by SEQ ID NO:1 or a sequence that hybridizes to SEQ ID NO:1 under moderate stringency hybridization conditions; degenerate variants thereof, alleles thereof; and hybridizable fragments thereof. In a particular embodiment, the nucleic acid encoding the EmaA polypeptide has the sequence selected from the group comprising SEQ ID NO:1; a sequence complementary to SEQ ID NO:1; or a homologous sequence which is substantially similar to SEQ ID NO:1. In a further embodiment, the nucleic acid has the sequence consisting of SEQ ID NO:1.

In a particular embodiment, the nucleic acid encoding the EmaB polypeptide has the sequence selected from the group comprising SEQ ID NO:3; a sequence that hybridizes to SEQ ID NO:3 under moderate stringency hybridization conditions; DNA sequences capable of encoding the amino acid sequence encoded by SEQ ID NO:3 or a sequence that hybridizes to SEQ ID NO:3 under moderate stringency hybridization conditions; degenerate variants thereof, alleles thereof, and hybridizable fragments thereof. In a particular embodiment, the nucleic acid encoding the EmaB polypeptide has the sequence selected from the group comprising SEQ ID NO:3; a sequence complementary to SEQ ID NO:3; or a homologous sequence which is substantially similar to SEQ ID NO:3. In a further embodiment, the nucleic acid has the sequence consisting of SEQ ID NO:3.

In a particular embodiment, the nucleic acid encoding the EmaC polypeptide has the sequence selected from the group comprising SEQ ID NO:5; a sequence that hybridizes to SEQ ID NO:5 under moderate stringency hybridization conditions; DNA sequences capable of encoding the amino acid sequence encoded by SEQ ID NO:5 or a sequence that hybridizes to SEQ ID NO:5 under moderate stringency hybridization conditions; degenerate variants thereof, alleles thereof; and hybridizable fragments thereof. In a particular embodiment, the nucleic acid encoding the EmaC polypeptide has the sequence selected from the group comprising SEQ ID NO:5; a sequence complementary to SEQ ID NO:5; or a homologous sequence which is substantially similar to SEQ ID NO:5. In a further embodiment, the nucleic acid has the sequence consisting of SEQ ID NO:5.

In a particular embodiment, the nucleic acid encoding the EmaD polypeptide has the sequence selected from the group comprising SEQ ID NO:7; a sequence that hybridizes to SEQ ID NO:7 under moderate stringency hybridization conditions; DNA sequences capable of encoding the amino acid sequence encoded by SEQ ID NO:7 or a sequence that hybridizes to SEQ ID NO:7 under moderate stringency hybridization conditions; degenerate variants thereof, alleles thereof, and hybridizable fragments thereof. In a particular embodiment, the nucleic acid encoding the EmaD polypeptide has the sequence selected from the group comprising SEQ ID NO:7; a sequence complementary to SEQ ID NO:7; or a homologous sequence which is substantially similar to SEQ ID NO:7. In a further embodiment, the nucleic acid has the sequence consisting of SEQ ID NO:7.

In a particular embodiment, the nucleic acid encoding the EmaE polypeptide has the sequence selected from the group comprising SEQ ID NO:9; a sequence that hybridizes to SEQ ID NO:9 under moderate stringency hybridization conditions; DNA sequences capable of encoding the amino acid sequence encoded by SEQ ID NO:9 or a sequence that hybridizes to SEQ ID NO:9 under moderate stringency hybridization conditions; degenerate variants thereof; alleles thereof; and hybridizable fragments thereof. In a particular embodiment, the nucleic acid encoding the EmaE polypeptide has the sequence selected from the group comprising SEQ ID NO:9; a sequence complementary to SEQ ID NO:9; or a homologous sequence which is substantially similar to SEQ ID NO:9 In a further embodiment, the nucleic acid has the sequence consisting of SEQ ID NO:9.

A nucleic acid capable of encoding a GBS polypeptide EmaA, EmaB, EmaC, EmaD or EmaE which is a recombinant DNA molecule is further provided. Such a recombinant DNA molecule wherein the DNA molecule is operatively linked to an expression control sequence is also provided herein.

The present invention relates to nucleic acid vaccines or DNA vaccines comprising nucleic acids encoding immunogenic bacterial Ema polypeptides, particularly immunogenic streptococcal Ema polypeptides. The present invention relates to nucleic acid vaccines or DNA vaccines comprising nucleic acids encoding immunogenic GBS Ema polypeptides, particularly selected from the group of EmaA, EmaB, EmaC, EmaD and EmaE. The present invention relates to nucleic acid vaccines or DNA vaccines comprising nucleic acids encoding one or more immunogenic GBS Ema polypeptide or a fragment thereof or any combination of one or more Ema polypeptide EmaA, EmaB, EmaC, EmaD or EmaE with at least one other GBS polypeptide, particularly wherein said other GBS polypeptide is selected from the group of Spb1, Spb2, C protein alpha antigen, Rib and immunogenic polypeptide fragments thereof.

The invention further relates to a vaccine for protection of an animal subject from infection with a streptococcal bacterium comprising a vector containing a gene encoding an Ema polypeptide, particularly selected from the group of EmaA, EmaB, EmaC, EmaD and EmaE, operatively associated with a promoter capable of directing expression of the gene in the subject. The invention further relates to a vaccine for protection of an animal subject from infection with a Group B streptococcal bacterium comprising a vector containing a gene encoding an Ema polypeptide selected from the group of EmaA, EmaB, EmaC, EmaD and EmaE operatively associated with a promoter capable of directing expression of the gene in the subject. The present invention further provides a nucleic acid vaccine comprising a recombinant DNA molecule capable of encoding a GBS polypeptide EmaA, EmaB, EmaC, EmaD or EmaE.

The present invention provides a vector which comprises the nucleic acid capable of encoding a bacterial Ema polypeptide, particularly a streptococcal Ema polypeptide. The present invention provides a vector which comprises the nucleic acid capable of encoding an Ema polypeptide selected from the group of EmaA, EmaB, EmaC, EmaD and EmaE and a promoter. The present invention provides a vector which comprises the nucleic acid of any of SEQ ID NO: 1, 3, 5, 7, 9, 24, 27, 30, and 33, and a promoter. The invention contemplates a vector wherein the promoter comprises a bacterial, yeast, insect or mammalian promoter. The invention contemplates a vector wherein the vector is a plasmid, cosmid, yeast artificial chromosome (YAC), bacteriophage or eukaryotic viral DNA.

The present invention further provides a host vector system for the production of a polypeptide which comprises the vector capable of encoding an Ema polypeptide, particularly selected from the group of EmaA, EmaB, EmaC, EmaD and EmaE, in a suitable host cell. A host vector system is provided wherein the suitable host cell comprises a prokaryotic or eukaryotic cell. A unicellular host transformed with a recombinant DNA molecule or vector capable of encoding an Ema polypeptide, particularly selected from the group of EmaA, EmaB, EmaC, EmaD and EmaE, is thereby provided.

A "vector" is a replicon, such as plasmid, phage or cosmid, to which another DNA segment may be attached so as to bring about the replication of the attached segment.

A "DNA" or "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence in the case of eukaryotic mRNA.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, in the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

It should be appreciated that also within the scope of the present invention are DNA sequences encoding an Ema polypeptide EmaA, EmaB, EmaC, EmaD or EmaE which code for an Ema polypeptide having the same amino acid sequence as any of SEQ ID NOS:2, 4, 6, 8 or 10, but which are degenerate to any of SEQ ID NOS: 1, 3, 5, 7 or 9. By "degenerate to" is meant that a different three-letter codon is used to specify a particular amino acid. It is well known in the art that the following codons can be used interchangeably to code for each specific amino acid: Phenylalanine (Phe or F) UUU or UUC; Leucine (Leu or L) UUA or UUG or CUU or CUC or CUA or CUG; Isoleucine (Ile or I) AUU or AUC or AUA; Methionine (Met or M) AUG; Valine (Val or V) GUU or GUC of GUA or GUG; Serine (Ser or S) UCU or UCC or UCA or UCG or AGU or AGC; Proline (Pro or P) CCU or CCC or CCA or CCG; Threonine (Thr or T) ACU or ACC or ACA or ACG; Alanine (Ala or A) GCU or GCG or GCA or GCG; Tyrosine (Tyr or Y) UAU or UAC; Histidine (H is or H) CAU or CAC; Glutamine (Gln or Q) CAA or CAG; Asparagine (Asn or N) AAU or AAC; Lysine (Lys or K) AAA or AAG; Aspartic Acid (Asp or D) GAU or GAC; Glutamic Acid (Glu or E) GAA or GAG; Cysteine (Cys or C) UGU or UGC; Arginine (Arg or R) CGU or CGC or CGA or CGG or AGA or AGG; Glycine (Gly or G) GGU or GGC or GGA or GGG; Tryptophan (Trp or W) UGG; Termination codon UAA (ochre) or UAG (amber) or UGA (opal).

It should be understood that the codons specified above are for RNA sequences. The corresponding codons for DNA have a T substituted for U.

Mutations can be made in SEQ ID NOS: 1, 3, 5, 7 or 9 such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the genie.

Further this invention also provides a vector which comprises the above-described nucleic acid molecule. The promoter may be, or is identical to, a bacterial, yeast, insect or mammalian promoter. Further, the vector may be a plasmid, cosmid, yeast artificial chromosome (YAC), bacteriophage or eukaryotic viral DNA. Other numerous vector backbones known in the art as useful for expressing protein may be employed. Such vectors include, but are not limited to: adenovirus, simian virus 40 (SV40), cytomegalovirus (CMV), mouse mammary tumor virus (MMTV), Moloney murine leukemia virus, DNA delivery systems, i.e. liposomes, and expression plasmid delivery systems. Such vectors may be obtained commercially or assembled from the sequences described by methods well-known in the art.

This invention also provides a host vector system for the production of a polypeptide which comprises the vector of a suitable host cell. A wide variety of unicellular host cells are also useful in expressing the DNA sequences of this invention. These hosts may include well known eukaryotic and prokaryotic hosts, such as strains of *E. coli, Pseudomonas, Bacillis, Streptomyces*, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAs, e.g., the numerous derivatives of phage λ, M13 and filamentous single stranded phage DNA; yeast plasmids such as the 2 .mu. plasmid or derivatives thereof, vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

This invention further provides a method of producing a polypeptide which comprises growing the above-described host vector system under suitable conditions permitting the production of the polypeptide and recovering the polypeptide so produced.

As used herein, "pg" means picogram, "ng" means nanogram, "ug" or "μg" mean microgram, "mg" means milligram, "ul" or "μl" mean microliter, "ml" means milliliter, "l" means liter.

The present invention extends to the preparation of antisense oligonucleotides and ribozymes that may be used to interfere with the expression of one or more Ema protein at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into Ema-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

Antibodies

This invention further provides an antibody capable of specifically recognizing or binding to the isolated Ema polypeptide of the present invention. The antibody may be a monoclonal or polyclonal antibody. Further, the antibody may be labeled with a detectable marker that is either a radioactive, calorimetric, fluorescent, or a luminescent marker. The labeled antibody may be a polyclonal or monoclonal antibody. In one embodiment, the labeled antibody is a purified labeled antibody. Methods of labeling antibodies are well known in the art.

In a further aspect, the present invention provides a purified antibody to a bacterial Ema polypeptide, particularly a streptococcal Ema polypeptide. In a still further aspect, the present invention provides a purified antibody to a Group B streptococcal polypeptide selected from the group of EmaA, EmaB, EmaC, EmaD and EmaE.

Antibodies against the isolated polypeptides of the present invention include naturally raised and recombinantly prepared antibodies. These may include both polyclonal and monoclonal antibodies prepared by known genetic techniques, as well as bi-specific (chimeric) antibodies, and antibodies including other functionalities suiting them for diagnostic use. Such antibodies can be used in immunoassays to diagnose infection with a particular strain or species of bacteria. The antibodies can also be used for passive immunization to treat an infection with Group B streptococcal bacteria. These antibodies may also be suitable for modulating bacterial adherence and/or invasion including but not limited to acting as competitive agents.

The present invention provides a monoclonal antibody to a Group B streptococcal polypeptide selected from the group of EmaA, EmaB, EmaC, EmaD and EmaE. The invention thereby extends to an immortal cell line that produces a monoclonal antibody to a Group B streptococcal polypeptide selected from the group of EmaA, EmaB, EmaC, EmaD and EmaE.

An antibody to an Ema polypeptide, particularly selected from EmaA, EmaB, EmaC, EmaD or EmaE, labeled with a detectable label is further provided. In particular embodiments, the label may selected from the group consisting of an enzyme, a chemical which fluoresces, and a radioactive element.

The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. Such antibodies include but are not limited to polyclonal, monoclonal, chimeric, single chain, Fab fragments, and an Fab expression library. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein. Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from $F(ab')_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

Various procedures known in the art may be used for the production of polyclonal antibodies to polypeptide or derivatives or analogs thereof (see, e.g., Antibodies—A Laboratory Manual, Harlow and Lane, eds., Cold Spring Harbor Laboratory Press: Cold Spring Harbor, N.Y., 1988). For the production of antibody, various host animals can be immunized by injection with the Group B streptococcal Ema polypeptide, an immunogenic fragment thereof, or a derivative (e.g., fragment or fusion protein) thereof, including but not limited to rabbits, mice, rats, sheep, goats, etc. In one embodiment, the polypeptide can be conjugated to an immunogenic carrier, e.g., bovine serum albumin (BSA) or keyhole limpet hemocyanin (KLH). Various adjuvant may be used to increase the immunological response, depending on the host species.

For preparation of monoclonal antibodies, or fragment, analog, or derivative thereof, any technique that provides for the production of antibody molecules by continuous cell lines in culture may be used (see, e.g., Antibodies—A Laboratory Manual, Harlow and Lane, eds., Cold Spring Harbor Laboratory Press: Cold Spring Harbor, N.Y., 1988). These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Monoclonal antibodies can be produced in germ-free animals utilizing recent technology (PCT/US90/02545). Human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al, 1984, J. Bacteriol. 159-870; Neuberger et al, 1984, Nature 312:604-608; Takeda et al., 1985, Nature 314:452-454) by splicing the genes from a mouse antibody molecule specific for a polypeptide together with genes from a human antibody molecule of appropriate biological activity can be used; such antibodies are within the scope of this invention. Such human or humanized chimeric antibodies are preferred for use in therapy of human infections or diseases, since the human or humanized antibodies are much less likely than xenogeneic antibodies to induce an immune response, in particular an allergic response, themselves. An additional embodiment of the invention utilizes the techniques described for the construction of Fab expression libraries (Huse et al., 1989, Science 246:1275-1281) to allow rapid and easy identification of monoclonal Fab fragments with the desired specificity for the polypeptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme B-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

Antibodies can be labeled for detection in vitro, e.g., with labels such as enzymes, fluorophores, chromophores, radioisotopes, dyes, colloidal gold, latex particles, and chemiluminescent agents. Alternatively, the antibodies can be labeled for detection in vivo, e.g., with radioisotopes (preferably technetium or iodine); magnetic resonance shift reagents (such as gadolinium and manganese); or radio-opaque reagents.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The polypeptide can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{58}Co$, $^{59}Fe$, $^{9}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be tilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

Diagnostic Applications

The present invention also relates to, a variety of diagnostic applications, including methods for identifying or monitoring streptococcal infections. The present invention also relates to a variety of diagnostic applications, including methods for identifying or monitoring Group B streptococcal infections. The present invention further relates to diagnostic applications or methods utilizing the polypeptides of the present invention, immunogenically recognized fragments thereof, or antibodies thereto. Such methods include the analysis and evaluation of agents, analogs or compounds which modulate the activity of the Ema polypeptides. The Ema polypeptides may also be utilized in diagnostic methods and assays for monitoring and determining immunological response and antibody response upon streptococcal infection or vaccination.

As described in detail above, antibody(ies) to the Ema polypeptides or fragments thereof can be produced and isolated by standard methods including the well known hybridoma techniques. For convenience, the antibody(ies) to the Ema polypeptides will be referred to herein as $Ab_1$, and antibody(ies) raised in another species as $Ab_2$.

The presence of streptococci in cells can be ascertained by the usual immunological procedures applicable to such determinations. A number of useful procedures are known. Procedures which are especially useful utilize either the Ema polypeptides labeled with a detectable label, antibody against the Ema polypeptides labeled with a detectable label, or secondary antibody labeled with a detectable label.

The procedures and their application are all familiar to those skilled in the art and accordingly may be utilized within the scope of the present invention. The “competitive” procedure, is described in U.S. Pat. Nos. 3,654,090 and 3,850,752. The “sandwich” procedure, is described in U.S. Pat. Nos. RE 31,006 and 4,016,043. Still other procedures are known such as the “double antibody,” or “DASP” procedure.

In each instance, the Ema polypeptides forms complexes with one or more antibody(ies) or binding partners and one member of the complex is labeled with a detectable label. The fact that a complex has formed and, if desired, the amount thereof, can be determined by known methods applicable to the detection of labels.

In a further embodiment of this invention, commercial test kits suitable for use by a medical specialist may be prepared to determine the presence or absence of streptococci, particularly of streptococci expressing one or more Ema polypeptide selected from the group of EmaA, EmaB, EmaC, EmaD and EmaE. In as much as the ema locus, as described herein, is found in the genomic DNA of many, if not all, serotypes of Group B streptococci, it is a useful general marker for Group B streptococci. In as much as Ema homologs exist in other species of streptococci, including Group A and *S. pneumoniae*, it is a useful general marker for streptococci. Therefore, commercial test kits for determining the presence or absence of streptococci, and thereby determining whether an individual is infected with streptococci are contemplated and provided by this invention. Therefore, commercial test kits for determining the presence or absence of Group B streptococci, and thereby determining whether an individual is infected with Group B streptococci are contemplated and provided by this invention.

The present invention includes methods for determining and monitoring infection by streptococci by detecting the presence of a streptococcal polypeptide selected from the group of EmaA, EmaB, EmaC, EmaD and EmaE. In a particular such method, the streptococcal Ema polypeptide is measured by:

a. contacting a sample in which the presence or activity of a Streptococcal polypeptide selected from the group of EmaA, EmaB, EmaC, EmaD and EmaE is suspected with an antibody to the said streptococcal polypeptide under conditions that allow binding of the streptococcal polypeptide to the antibody to occur; and b. detecting whether binding has occurred between the streptococcal polypeptide from the sample and the antibody; wherein the detection of binding indicates the presence or activity of the streptococcal polypeptide in the sample.

The present invention includes methods for determining and monitoring infection by Group B streptococci by detecting the presence of a Group B streptococcal polypeptide selected from the group of EmaA, EmaB, EmaC, EmaD and EmaE. In a particular such method, the streptococcal Ema polypeptide is measured by:

a. contacting a sample in which the presence or activity of a Group B Streptococcal polypeptide selected from the group of EmaA, EmaB, EmaC, EmaD and EmaE is suspected with an antibody to the said Group B streptococcal polypeptide under conditions that allow binding of the Group B streptococcal polypeptide to the antibody to occur; and b. detecting whether binding has occurred between the Group B streptococcal polypeptide from the sample and the antibody; wherein the detection of binding indicates the presence or activity of the Group B streptococcal polypeptide in the sample.

The present invention further provides a method for detecting the presence of a bacterium having a gene encoding a Group B polypeptide selected from the group of emaA, emaB, emaC, emaD and emaE, comprising:

a. contacting a sample in which the presence or activity of the bacterium is suspected with an oligonucleotide which hybridizes to a Group B streptococcal polypeptide gene selected from the group of emaA, emaB, emaC, emaD and emaE, under conditions that allow specific hybridization of the oligonucleotide to the gene to occur; and b. detecting whether hybridization has occurred between the oligonucleotide and the gene; wherein the detection of hybridization indicates that presence or activity of the bacterium in the sample.

The invention includes an assay system for screening of potential compounds effective to modulate the activity of a bacterial Ema protein of the present invention. In one instance, the test compound, or an extract containing the compound, could be administered to a cellular sample expressing the particular Ema protein to determine the compound's effect upon the activity of the protein by comparison with a control. In a further instance the test compound, or an extract containing the compound, could be administered to a cellular sample expressing the Ema protein to determine the compound's effect upon the activity of the protein, and thereby on adherence of said cellular sample to host cells, by comparison with a control.

Accordingly, a test kit may be prepared for the demonstration of the presence of Ema polypeptide or Ema activity in cells, comprising:

a. a predetermined amount of at least one labeled immunochemically reactive component obtained by the direct or indirect attachment of the Ema polypeptide or a specific binding partner thereto, to a detectable label;

b. other reagents; and c. directions for use of said kit.

More specifically, the diagnostic test kit may comprise:

a. a known amount of the Ema polypeptide as described above (or a binding partner) generally bound to a solid phase to form an immunosorbent, or in the alternative, bound to a suitable tag, or plural such end products, etc. (or their binding partners) one of each;

b. if necessary, other reagents; and c. directions for use of said test kit.

In a further variation, the test kit may be prepared and used for the purposes stated above, which operates according to a predetermined protocol (e.g. "competitive," "sandwich," "double antibody," etc.), and comprises:

a. a labeled component which has been obtained by coupling the Ema polypeptide to a detectable label;

b. one or more additional immunochemical reagents of which at least one reagent is a ligand or an immobilized ligand, which ligand is selected from the group consisting of:

(i) a ligand capable of binding with the labeled component a.;

(ii) a ligand capable of binding with a binding partner of the labeled component a.;

(iii) a ligand capable of binding with at least one of the component(s) to be determined; and (iv) a ligand capable of binding with at least one of the binding partners of at least one of the component(s) to be determined; and c. directions for the performance of a protocol for the detection and/or determination of one or more components of an immunochemical reaction between the Ema polypeptide and a specific binding partner thereto.

In accordance with the above, an assay system for screening potential drugs effective to modulate the activity of the Ema polypeptide may be prepared. The Ema polypeptide may be introduced into a test system, and the prospective drug may also be introduced into the resulting cell culture, and the culture thereafter examined to observe any changes in the Ema polypeptide activity of the cells, due either to the addition of the prospective drug alone, or due to the effect of added quantities of the known Ema polypeptide.

Therapeutic Applications

The therapeutic possibilities that are raised by the existence of the Group B streptococcal Ema polypeptides EmaA, EmaB, EmaC, EmaD and EmaE derive from the fact that the Ema polypeptides of the present invention are found generally in various serotypes of Group B streptococci. In addition, broader therapeutic possibilities that are raised by the existence of Ema homologous polypeptides in various distinct species of streptococci including *S. pneumoniae* and *S. pyogenes*. In addition Ema homologous polypeptides have been identified in *E. faecalis* and *C. diptheriae*. Of particular relevance to their suitability in vaccine and immunological therapy is that the Ema A, EmaB, and EmaC polypeptides possess N-terminal sequences consistent with a signal peptide, indicating secretion from the bacterial cell and at least partial extracellular localization. In addition, the EmaA, EmaB, EmaC, EmaD and EmaE polypeptides demonstrate homology to distinct bacterial proteins involved in or implicated in bacterial adhesion and invasion. Thus, the Ema polypeptides are anticipated to be involved in or required for streptococcal adhesion to and/or invasion of cells, critical for bacterial survival and virulence in the human host.

Modulators of Extracellular Matrix Adhesin Protein

Thus, in instances where it is desired to reduce or inhibit the effects resulting from the extracellular matrix adhesin protein Ema of the present invention, an appropriate inhibitor of one or more of the Ema proteins, particularly EmaA, EmaB, EmaC, EmaD and EmaE could be introduced to block the activity of one or more Ema protein.

The present invention contemplates screens for a modulator of an Ema polypeptide, in particular modulating adhesion or invasion facilitated by EmaA, EmaB, EmaC, EmaD or EmaE. In one such embodiment, an expression vector containing the Ema polypeptide of the present invention, or a derivative or analog thereof, is placed into a cell in the presence of at least one agent suspected of exhibiting Ema polypeptide modulator activity. The cell is preferably a bacterial cell, most preferably a streptococcal cell, or a bacterial host cell. The amount of adhesion or binding activity is determined and any such agent is identified as a modulator when the amount of adhesion or binding activity in the presence of such agent is different than in its absence. The vectors may be introduced by any of the methods described above. In a related embodiment the GBS Ema polypeptide is expressed in streptococci and the step of determining the amount of adhesion or binding activity is performed by determining the amount of binding to bacterial host cells in vitro.

When the amount of adhesion or binding activity in the presence of the modulator is greater than in its absence, the modulator is identified as an agonist or activator of the Ema polypeptide, whereas when the amount of adhesion binding activity in the presence of the modulator is less than in its absence, the modulator is identified as an antagonist or inhibitor of the Ema polypeptide. As any person having skill in the art would recognize, such determinations as these and those below could require some form of statistical analysis, which is well within the skill in the art.

Natural effectors found in cells expressing Ema polypeptide can be fractionated and tested using standard effector assays as exemplified herein, for example. Thus an agent that is identified can be a naturally occurring adhesion or binding modulator. Alternatively, natural products libraries can be screened using the assays of the present invention for screening such agents.

Another approach uses recombinant bacteriophage to produce large libraries. Using the "phage method" [Scott and Smith, 1990, Science 249:386-390 (1990); Cwirla, et al., Proc. Natl. Acad. Sci., 87:6378-6382 (1990); Devlin et al., Science, 249:404-406 (1990)], very large libraries can be constructed ($10^6$-$10^8$ chemical entities). Yet another approach uses primarily chemical methods, of which the Geysen method [Geysen et al., Molecular Immunology 23:709-715 (1986); Geysen et al. J. Immunologic Method 102:259-274 (1987)] and the method of Fodor et al. [Science 251:767-773 (1991)] are examples. Furka et al. [14th International Congress of Biochemistry, Volume 5, Abstract FR:013 (1988); Furka, Int. J. Peptide Protein Res. 37:487-493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested.

In another aspect, synthetic libraries [Needels et al., Proc. Natl. Acad. Sci. USA 90:10700-4 (1993); Ohlmeyer et al., Proc. Natl. Acad. Sci. USA 90:10922-10926 (1993); Lam et al., International Patent Publication No. WO 92/00252; Kocis et al., International Patent Publication No. WO 9428028, each of which is incorporated herein by reference in its entirety], and the like can be used to screen for such an agent.

This invention provides antagonist or blocking agents which include but are not limited to: peptide fragments, mimetic, a nucleic acid molecule, a ribozyme, a polypeptide, a small molecule, a carbohydrate molecule, a monosaccharide, an oligosaccharide or an antibody. Also, agents which competitively block or inhibit streptococcal bacterium are contemplated by this invention. This invention provides an agent which comprises an inorganic compound, a nucleic acid molecule, an oligonucleotide, an organic compound, a peptide, a peptidomimetic compound, or a protein which inhibits the polypeptide.

Vaccines

In a further aspect, the present invention extends to vaccines based on the Ema proteins described herein. The present invention provides a vaccine comprising one or more Group B streptococcal polypeptide selected from the group of EmaA, EmaB, EmaC, EmaD and EmaE, and a pharmaceutically acceptable adjuvant. The present invention provides a vaccine comprising one or more bacterial Ema polypeptide selected from the group of polypeptides comprising the amino acid sequence set out in any of SEQ ID NO:23, 26, 29, 32 and 37, and a pharmaceutically acceptable adjuvant.

The present invention further provides a vaccine comprising one or more Group B streptococcal polypeptide selected from the group of EmaA, EmaB, EmaC, EmaD and EmaE, further comprising one or more additional GBS antigen. The present invention further provides a vaccine comprising one or more Group B streptococcal polypeptide selected from the group of EmaA, EmaB, EmaC, EmaD and EmaE, further comprising one or more antigens selected from the group of the polypeptide Spb1 or an immunogenic fragment thereof, the polypeptide Spb2 or an immunogenic fragment thereof, C protein alpha antigen or an immunogenic fragment thereof, Rib or an immunogenic fragment thereof, Lmb or an immunogenic fragment thereof, C5a-ase or an immunogenic fragment thereof, and Group B streptococcal polysaccharides or oligosaccharides.

In another aspect, the invention is directed to a vaccine for protection of an animal subject from infection with streptococci comprising an immunogenic amount of one or more streptococcal Ema polypeptide, or a derivative or fragment thereof. The Erna polypeptide may be particularly selected from the group of EmaA, EmaB, EmaC, EmaD or EmaE, or a derivative or fragment thereof. In a further aspect, the invention is directed to a vaccine for protection of an animal subject from infection with streptococci comprising an immunogenic amount of one or more Ema polypeptide EmaA, EmaB, EmaC, EmaD or EmaE, or a derivative or fragment thereof. In a further aspect, the invention is directed to a vaccine for protection of an animal subject from infection with GBS comprising an immunogenic amount of one or more Ema polypeptide EmaA, EmaB, EmaC, EmaD or EmaE, or a derivative or fragment thereof. Such a vaccine may contain the protein conjugated covalently to a streptococcal or GBS bacterial polysaccharide or oligosaccharide or polysaccharide or oligosaccharide from one or more streptococcal or GBS serotypes.

This invention provides a vaccine which comprises a polypeptide bacterial Ema protein and a pharmaceutically acceptable adjuvant or carrier. In particular, a vaccine is provided which comprises one or more Ema polypeptides selected from the group of EmaA, EmaB, EmaC, EmaD and EmaE. This invention provides a vaccine which comprises a combination of at least one bacterial Ema protein selected from the group of EmaA, EmaB, EmaC, EmaD and EmaE and at least one other Group B streptococcal protein particularly Spb1 and/or Spb2 and/or C protein alpha antigen, and a pharmaceutically acceptable adjuvant or carrier. The Ema polypeptide may comprise an amino acid sequence of a Ema protein EmaA, EmaB, EmaC, EmaD, EmaE as set forth in FIGS. 2-6 and SEQ ID NOS:2, 4, 6, 8 and 10.

This invention further provides a vaccine comprising an isolated nucleic acid encoding a bacterial Ema polypeptide and a pharmaceutically acceptable adjuvant or carrier. This invention further provides a vaccine comprising an isolated nucleic acid encoding a streptococcal Ema polypeptide and a pharmaceutically acceptable adjuvant or carrier. This invention further provides a vaccine comprising an isolated nucleic acid encoding a GBS Ema polypeptide and a pharmaceutically acceptable adjuvant or carrier. This invention further provides a vaccine comprising isolated nucleic acid encoding one or more GBS Ema polypeptide, particularly selected from the group of EmaA, EmaB, EmaC, EmaD and EmaE and a pharmaceutically acceptable adjuvant or carrier. The nucleic acid may comprise a nucleic acid sequence of a GBS Ema polypeptide as set forth in any of SEQ ID NOS:1, 3, 5, 7, or 9.

Active immunity against streptococci can be induced by immunization (vaccination) with an immunogenic amount of the polypeptide, or peptide derivative or fragment thereof, and an adjuvant, wherein the polypeptide, or antigenic derivative or fragment thereof, is the antigenic component of the vaccine. The polypeptide, or antigenic derivative or fragment thereof, may be one antigenic component, in the presence of other antigenic components in a vaccine. For instance, the polypeptide of the present invention may be combined with other known streptococcal polypeptides or poly/oligosaccharides, or immunogenic fragments thereof, including for instance GBS capsular polysaccharide, Spb1, Spb2, C protein alpha antigen, Rib, Lmb, and C5a-ase in a multi-component vaccine. Such multi-component vaccine may be utilized to enhance immune response, even in cases where the polypeptide of the present invention elicits a response on its own. The polypeptide of the present invention may also be combined with existing vaccines, whole bacterial or capsule-based vaccines, alone or in combination with other GBS polypeptides, particularly Spb1 and/or Spb2 and/or C protein alpha antigen and/or Rib to enhance such existing vaccines.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., Immunology, Second Ed, 1984, Benjamin/Cummings: Menlo Park, Calif., p. 384). Often, a primary challenge with an antigen alone, in the absence of an adjuvant, will fail to elicit a humoral or cellular immune response.

Adjuvant include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calniette-Guerin) and *Corynebacterium parvum*. Preferably, the adjuvant is pharmaceutically acceptable.

The invention further provides a vaccine which comprises a non-adherent, non-virulent mutant, including but not limited to the $ema^-$ mutants herein described and contemplated. Medaglini et al (Madaglini et al (1995) Proc Natl Acad Sci USA 92; 6868-6872) and Oggioni and Pozzi (Oggioni, M. R. and Pozzi, G. (1996) Gene 169:85-90) have previously described the use of *Streptococcus gordonii*, a commensal bacterium of the human oral cavity, as live vaccine delivery vehicles and for heterologous gene expression. Such $ema^-$ mutant can therefore be utilized as a vehicle for expression of immunogenic proteins for the purposes of eliciting an immune response to such other proteins in the context of vaccines. Active immunity against Group B streptococci, can be induced by immunization (vaccination) with an immunogenic amount of the $ema^-$ vehicle expressing an immunogenic protein. Also contemplated by the present invention is the use of any such $ema^-$ mutant in expressing a therapeutic protein in the host in the context of other forms of therapy.

The polypeptide of the present invention, or fragments thereof, can be prepared in an admixture with an adjuvant to prepare a vaccine. Preferably, the polypeptide or peptide derivative or fragment thereof, used as the antigenic component of the vaccine is an antigen common to all or many serotypes of GBS bacteria, or common to closely related species of bacteria, for instance *Streptococcus*.

Vectors containing the nucleic acid-based vaccine of the invention can be introduced into the desired host by methods known in the art, e.g., transfection, electroporation, micro injection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

The modes of administration of the vaccine or compositions of the present invention may comprise the use of any suitable means and/or methods for delivering the vaccine or composition to the host animal whereby they are immumostimulatively effective. Delivery modes may include, without limitation, parenteral administration methods, such as paracancerally, transmucosally, transdermally, intramuscularly, intravenously, intradermally, subcutaneously, intraperitonealy, intraventricularly, intracranially and intratumorally. Preferably, since the desired result of vaccination is to elucidate an immune response to the antigen, and thereby to the pathogenic organism, administration directly, or by targeting or choice of a viral vector, indirectly, to lymphoid tissues, e.g., lymph nodes or spleen, is desirable. Since immune cells are continually replicating, they are ideal target for retroviral vector-based nucleic acid vaccines, since retroviruses require replicating cells. These vaccines and compositions can be used to immunize mammals, for example, by the intramuscular or parenteral routes, or by delivery to mucosal surfaces using microparticles, capsules, liposomes and targeting molecules, such as toxins and antibodies. The vaccines and immunogenic compositions may be administered to mucosal surfaces by, for example, the nasal or oral (intragastric) routes. Alternatively, other modes of administration including suppositories may be desirable. For suppositories, binders and carriers may include, for example, polyalkylene glycols and triglycerides. Oral formulations may include normally employed incipients, such as pharmaceutical grades of saccharine, cellulose and magnesium carbonate.

These compositions may take the form of solutions, suspensions, tablets, pills, capsules, sustained release formulations or powders and contain 1 to 95% of the immunogenic compositions of the present invention. The immunogenic compositions are administered in a manner compatible with the dosage formulation, and in such amount as to be therapeutically effective, protective and immunogenic. The quantity to be administered depends on the subject to the immunized, including, for example, the capacity of the subject's immune system to synthesize antibodies, and if needed, to produce a cell-mediated, humoral or antibody-mediated immune response. Precise amounts of antigen and immunogenic composition to be administered depend on the judgement of the practitioner. However, suitable dosage ranges are readily determinable by those skilled in the art and may be of the order of micrograms to milligrams. Suitable regimes for initial administration and booster doses are also variable, but may include an initial administration followed by subsequent administrations. The dosage of the vaccine may also depend on the route of administration and will vary according to the size of the host.

Passive immunity can be conferred to an animal subject suspected of suffering an infection with streptococci by administering antiserum, polyclonal antibodies, or a neutralizing monoclonal antibody against one or more Ema polypeptide of the invention to the patient. A combination of antibodies directed against one or more Ema polypeptide selected from the group of EmaA, EmaB, EmaC, EmaD and EmaE, in combination with one or more of antibodies against Spb1, Spb2, Rib and C protein alpha antigen is also contemplated by the present invention. Although passive immunity does not confer long term protection, it can be a valuable tool for the treatment of a bacterial infection in a subject who has not been vaccinated. Passive immunity is particularly important for the treatment of antibiotic resistant strains of bacteria, since no other therapy may be available. Preferably, the antibodies administered for passive immune therapy are autologous antibodies. For example, if the subject is a human, preferably the antibodies are of human origin or have been "humanized," in order to minimize the possibility of an immune response against the antibodies. The active or passive vaccines of the invention can be used to protect an animal subject from infection by *streptococcus*, particularly Group B *streptococcus*.

Vaccines for GBS have been previously generated and tested. Preliminary vaccines used unconjugated purified polysaccaride. GBS polysaccharides and oligosaccharides are poorly immunogenic and fail to elicit significant memory and booster responses. Baker et al immunized 40 pregnant women with purified serotype III capsular polysaccharide (Baker, C. J. et al. (1998) New Engl J of Med 319:1180-1185). Overall, only 57% of women with low levels of specific antibody responded to the vaccine. The poor immunogenicity of purified polysaccharide antigen was further demonstrated in a study in which thirty adult volunteers were immunized with a tetravalent vaccine composed of purified polysaccharide from serotypes Ia, Ib, II, and III (Kotloff, K. L. et al. (1996) Vaccine 14:446-450). Although safe, this vaccine was only modestly immunogenic, with only 13% of subjects responding to type Ib, 17% to type II, 33% responding to type Ia, and 70% responding to type III polysaccharide. The poor immunogenicity of polysaccaride antigens prompted efforts to develop polysaccharide conjugate vaccines, whereby these polysaccharides or oligosaccharides are conjugated to protein carriers. Ninety percent of healthy adult women immunized with a type III polysaccharide-tetanus toxoid conjugate vaccine responded with a 4-fold rise in antibody concentration, compared to 50% immunized with plain polysaccharide (Kasper, D. L. et al (1996) J of Clin Invest 98:2308-2314). A type Ia/Ib polysaccharide-tetanus toxoid conjugate vaccine was similarly more immunogenic in healthy adults than plain polysaccharide (Baker, C. J. et al (1999) J Infect Dis 179:142-150).

The general method for the conjugation of polysaccharide is described in Wessels et al (Wessels, M. R. et al (1990) J. Clin Investigation 86: 1428-1433). Prior to coupling with tetanus toxoid, aldehyde groups are introduced on the polysaccharide by controlled periodate oxidation, resulting in the conversion of a portion of the sialic acid residues of the polysaccharide to residues of the 8-carbon analogue of sialic acid, 5-acetamido-3,5-dideoxy-D-galactosyloctulosonic acid. Tetanus toxoid is conjugated to the polysaccharide by reductive amination using free aldehyde groups present on the partially oxidized sialic acid residues. The preparation and conjugation of oligosaccharides is described in Paoletti et al (Paoletti, L. C. et al (1990) J. Biol Chem 265: 18278-18283). Purified capsular polysaccharide is depolymerized by enzymatic digestion using endo-beta-galactosidase produced by *Citrobacter freundii*. Following digestion, oligosaccharides are fractionated by gel filtration chromatography. Tetanus toxoid was covalently coupled via a synthetic spacer molecule to the reducing end of the oligosaccharide by reductive amination.

Methods and vaccines comprising GBS conjugate vaccines, comprising capsular polysaccharide and protein are provided and described in U.S. Pat. Nos. 5,993,825, 5,843,461, 5,795,580, 5,302,386 and 4,356,263, which are incorporated herein by reference in their entirety. These conjugate vaccines include polysaccharide-tetanus toxoid conjugate vaccines.

One polypeptide proposed to be utilized in a GBS vaccine is the repetitive GBS C protein alpha antigen, which contains up to nine tandemly repeated units of 82 amino acids (Michel, J. K. et al (1992) PNAS USA 89: 10060-10064). The polypeptide, methods and vaccines thereof, including polysaccharide-conjugate vaccines generated therewith, are provided and described in U.S. Pat. Nos. 5,968,521, 5,908,629, 5,858,362, 5,847,081, 5,843,461, 5,843,444, 5,820,860, and 5,648,241, which are herein incorporated by reference in their entirety. Antibodies generated against C protein alpha antigen with a large numbers of repeats protect against infection, but GBS are able to change the structure of the protein by deleting one or more of the repeat regions and escape detection by these antibodies (Madoff, L. C. et al (1996) PNAS USA 93: 4131-4136). This effect could theoretically be prevented by immunization with a protein with a lower number of repeat units, but the immunogenicity of the C protein alpha antigen is inversely related to the number of repeats—65% of mice responded to immunization with the 9-repeat protein, but only 11% to a 1-repeat protein (Cravekamp, C. et al (1997) Infect Immunity 65: 5216-5221). This is a disadvantage with any protein with a repetitive structure—it is common for bacteria to be able to alter or reassort these genes to alter the proteins exposed on their surface.

Typical doses for a vaccine composed of a protein antigen are in the range of 2.5-50 ug of total protein per dose. Typical doses for a polysaccharide-protein conjugate vaccine are 7.5-25 ug of polysaccharide and 1.25-250 ug of carrier protein. These types of vaccines are almost always given intramuscularly. Dosing schedules of a vaccine can be readily determined by the skilled artisan, particularly by comparison of similar vaccines, including other GBS vaccines. If used as a universal vaccine, a GBS vaccine would be integrated into the routine immunization schedule. Most similar vaccines require a primary series of immunizations (usually 2 or 3 doses at 2 month intervals beginning at 1 or 2 months of age) and a single booster at 12-18 months of age. A smaller number of doses or a single dose may be adequate in older children (over a year of age). For immunization of pregnant women, an exemplary immunization schedule would be a single dose given in the second or early third trimester. For immunization of non-pregnant adults, a single dose would probably be used. The requirement for subsequent booster doses in adults is difficult to predict—this would be based on the immunogenicity of the vaccine and ongoing surveillance of vaccine efficacy.

Immunogenic Compositions

In a further aspect, the present invention provides an immunogenic composition comprising one of more bacterial Ema polypeptides. In a still further aspect, the present invention provides an immunogenic composition comprising one of more streptococcal Ema polypeptides. In a particular aspect, the present invention provides an immunogenic composition comprising one of more Group B streptococcal polypeptides selected from the group of EmaA, EmaB, EmaC, EmaD, EmaE and a fragment thereof, and a pharmaceutically acceptable adjuvant. Immunogenic compositions may comprise a combination of one or more Group B Ema polypeptide, or an immunogenic polypeptide fragment thereof, with one or more additional GBS polypeptide or GBS capsular polysaccharide or oligosaccharide.

The present invention further provides an immunogenic composition comprising one or more Group B streptococcal polypeptide selected from the group of EmaA, EmaB, EmaC, EmaD and EmaE, further comprising one or more antigens selected from the group of the polypeptide Spb1 or an immunogenic fragment thereof, the polypeptide Spb2 or an immunogenic fragment thereof, C protein alpha antigen or an immunogenic fragment thereof, Rib or an immunogenic fragment thereof, and Group B streptococcal polysaccharides or oligosaccharides.

Pharmaceutical Compositions

The invention provides pharmaceutical compositions comprising a bacterial Ema polypeptide, particularly a streptococcal Ema polypeptide, and a pharmaceutically acceptable carrier. The invention provides pharmaceutical compositions comprising a Group B streptococcal polypeptide selected from the group of EmaA, EmaB, EmaC, EmaD and EmaE, and a pharmaceutically acceptable carrier. The present invention further provides pharmaceutical compositions comprising one or more GBS Ema polypeptide, or a fragment thereof, in combination with one or more of GBS polypeptide Spb1, Spb2, C protein alpha antigen, Rib, a Group B streptococcal polysaccharide or oligosaccharide vaccine, and an anti-streptococcal vaccine.

Such pharmaceutical composition for preventing streptococcal attachment to mucosal surface may include antibody to Ema polypeptide EmaA, EmaB, EmaC, EmaD or EmaE or any combination of antibodies to one or more such Ema polypeptide. In addition, any such composition may further include antibody to GBS polypeptides Spb1, Spb2, C protein alpha antigen, or Rib. Blocking adherence using such antibody blocks the initial step in infection thereby reducing colonization. This in turn decreases person to person transmission and prevents development of symptomatic disease.

The present invention provides a pharmaceutical composition comprising an antibody to a Group B streptococcal protein selected from the group of EmaA, EmaB, EmaC, EmaD and EmaE, and a pharmaceutically acceptable carrier. The invention further provides a pharmaceutical composition comprising a combination of at least two antibodies to Group B streptococcal proteins and a pharmaceutically acceptable carrier, wherein at least one antibody to a protein selected from the group of EmaA, EmaB, EmaC, EmaD, EmaE, is combined with at least one antibody to a protein selected from the group of Spb1, Spb2, Rib, and C protein alpha antigen.

It is still a further object of the present invention to provide a method for the prevention or treatment of mammals to control the amount or activity of streptococci, so as to treat or prevent the adverse consequences of invasive, spontaneous, or idiopathic pathological states.

It is still a further object of the present invention to provide a method for the prevention or treatment of mammals to control the amount or activity of Group B streptococci, so as to treat or prevent the adverse consequences of invasive, spontaneous, or idiopathic pathological states.

The invention provides a method for preventing infection with a bacterium that expresses a streptococcal Ema polypeptide comprising administering an immunogenically effective dose of a vaccine comprising an Ema polypeptide selected from the group of EmaA, EmaB, EmaC, EmaD and EmaE to a subject.

The invention further provides a method for preventing infection with a bacterium that expresses a Group B streptococcal Ema polypeptide comprising administering an immunogenically effective dose of a vaccine comprising an Ema polypeptide selected from the group of EmaA, EmaB, EmaC, EmaD and EmaE to a subject.

The present invention is directed to a method for treating infection with a bacterium that expresses a Group B streptococcal Ema polypeptide comprising administering a therapeutically effective dose of a pharmaceutical composition comprising an Ema polypeptide selected from the group of EmaA, EmaB, EmaC, EmaD and EmaE, and a pharmaceutically acceptable carrier to a subject.

The invention further provides a method for treating infection with a bacterium that expresses a Group B streptococcal Ema polypeptide comprising administering a therapeutically effective dose of a pharmaceutical composition comprising an antibody to an Ema polypeptide selected from the group of EmaA, EmaB, EmaC, EmaD and EmaE, and a pharmaceutically acceptable carrier to a subject.

In a further aspect, the invention provides a method of inducing an immune response in a subject which has been exposed to or infected with a Group B streptococcal bacterium comprising administering to the subject an amount of the pharmaceutical composition comprising an Ema polypeptide selected from the group of EmaA, EmaB, EmaC, EmaD and EmaE, and a pharmaceutically acceptable carrier, thereby inducing an immune response.

The invention still further provides a method for preventing infection by a streptococcal bacterium in a subject comprising administering to the subject an amount of a pharmaceutical composition comprising an antibody to an Ema polypeptide selected from the group of EmaA, EmaB, EmaC, EmaD and EmaE and a pharmaceutically acceptable carrier or diluent, thereby preventing infection by a streptococcal bacterium.

The invention further provides an ema mutant bacterium which is non-adherent and/or non-invasive to cells and which is mutated in one or more genes selected from the group of emaA, emaB, emaC, emaD and emaE. Particularly, such ema mutant is a Group B streptococcal bacterium. Such non-adherent and/or non-invasive ema mutant bacteria can further be utilized in expressing other immunogenic or therapeutic proteins for the purposes of eliciting immune responses to any such other proteins in the context of vaccines and in other forms of therapy.

This invention provides a method of inhibiting colonization of host cells in a subject which has been exposed to or infected with a streptococcal bacterium comprising administering to the subject an amount of a pharmaceutical composition comprising an Ema polypeptide selected from the group of EmaA, EmaB, EmaC, EmaD and EmaE, thereby inducing an immune response. The therapeutic peptide that blocks colonization is delivered by the respiratory mucosal. The pharmaceutical composition comprises the polypeptide selected from the group of SEQ ID NO: 2, 4, 6, 8 and 10.

As used herein, "pharmaceutical composition" could mean therapeutically effective amounts of polypeptide products or antibodies of the invention together with suitable diluents, preservatives, solubilizers, emulsifiers, adjuvant and/or carriers useful in therapy against bacterial infection or in inducing an immune response. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., TWEEN 20, TWEEN 80, PLURONIC F68, bile acid salts), solubilizing agents (e.g., glycerol, polyethylene glycerol), anti-oxidants (e.g., ascorbic acid, sodium metabisulfite), preservatives (e.g., THIMEROSAL, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of the polypeptides of the present invention. The choice of compositions will depend on the physical and chemical properties of the polypeptide. Controlled or sustained release compositions include formulation in lipophilic depots (e.g., fatty acids, waxes, oils). Also comprehended by the invention are particulate compositions coated with polymers (e.g., poloxamers or poloxamines) and the polypeptides of the present invention coupled to antibodies directed against tissue-specific receptors, ligands or antigens or coupled to ligands of tissue-specific receptors. Other embodiments of the compositions of the invention incorporate particulate forms, protective coatings, protease inhibitors or permeation enhancers for various routes of administration, including parenteral, pulmonary, nasal and oral.

Further, as used herein "pharmaceutically acceptable carrier" are well known to those skilled in the art and include, but are not limited to, 0.01-0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant infection by streptococcal bacterium. Alternatively, in the case of a vaccine or immunogenic composition, a therapeutically effective amount is used herein to mean an amount sufficient and suitable to elicit an immune response and antibody response in an individual, and particularly to provide a response sufficient to prevent, and preferably reduce by at least about 30 percent, more preferably by at least 50 percent, most preferably by at least 90 percent, a clinically significant infection by streptococcal bacterium.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

When administered, compounds are often cleared rapidly from mucosal surfaces or the circulation and may therefore elicit relatively short-lived pharmacological activity. Consequently, frequent administrations of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Dosages. The sufficient amount may include but is not limited to from about 1 μg/kg to about 1000 mg/kg. The amount may be 10 mg/kg. The pharmaceutically acceptable form of the composition includes a pharmaceutically acceptable carrier.

As noted above, the present invention provides therapeutic compositions comprising pharmaceutical compositions comprising vectors, vaccines, polypeptides, nucleic acids and antibodies, anti-antibodies, and agents, to compete with the Group B streptococcus bacterium for pathogenic activities, such as adherence to host cells.

The preparation of therapeutic compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An active component can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

A composition comprising "A" (where "A" is a single protein, DNA molecule, vector, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. In the context of the present invention, a deficit in the response of the host is evidenced by continuing or spreading bacterial infection. An improvement in a clinically significant condition in the host includes a decrease in bacterial load, clearance of bacteria from colonized host cells, reduction in fever or inflammation associated with infection, or a reduction in any symptom associated with the bacterial infection.

According to the invention, the component or components of a therapeutic composition of the invention may be introduced parenterally, transmucosally, e.g., orally, nasally, pulmonarailly, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. Oral or pulmonary delivery may be preferred to activate mucosal immunity; since Group B streptococci generally colonize the nasopharyngeal and pulmonary mucosa, particularly that of neonates, mucosal immunity may be a particularly effective preventive treatment. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macronol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Preferably, a controlled release device is introduced into a subject in proximity of the site of inappropriate immune activation or a tumor. Other controlled release systems are discussed in the review by Langer (Science 249:1527-1533 (1990)).

A subject in whom administration of an active component as set forth above is an effective therapeutic regimen for a bacterial infection is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., i.e., for veterinary medical use.

In the therapeutic methods and compositions of the invention, a therapeutically effective dosage of the active component is provided. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing. Generally, for intravenous injection or infusion, dosage may be lower than for intraperitoneal, intramuscular, or other route of administration. The dosing schedule may vary, depending on the circulation half-life, and the formulation used. The compositions are administered in a manner compatible with the dosage formulation in the therapeutically effective amount. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Administration with other compounds. For treatment of a bacterial infection, one may administer the present active component in conjunction with one or more pharmaceutical compositions used for treating bacterial infection, including but not limited to (1) antibiotics; (2) soluble carbohydrate inhibitors of bacterial adhesin; (3) other small molecule inhibitors of bacterial adhesin; (4) inhibitors of bacterial metabolism, transport, or transformation; (5) stimulators of bacterial lysis, or (6) anti-bacterial antibodies or vaccines directed at other bacterial antigens. Other potential active components include anti-inflammatory agents, such as steroids and non-steroidal anti-inflammatory drugs. Administration may be simultaneous (for example, administration of a mixture of the present active component and an antibiotic), or may be in seriatim.

Accordingly, in specific embodiment, the therapeutic compositions may further include an effective amount of the active component, and one or more of the following active ingredients: an antibiotic, a steroid, etc.

Thus, in a specific instance where it is desired to reduce or inhibit the infection resulting from a bacterium mediated binding of bacteria to a host cell, or an antibody thereto, or a ligand thereof or an antibody to that ligand, the polypeptide is introduced to block the interaction of the bacteria with the host cell.

Also contemplated herein is pulmonary delivery of an inhibitor of the polypeptide of the present invention having which acts as adhesin inhibitory agent (or derivatives thereof). The adhesin inhibitory agent (or derivative) is delivered to the lungs of a mammal, where it can interfere with bacterial, i.e., streptococcal, and preferably Group B streptococcal binding to host cells. Other reports of preparation of proteins for pulmonary delivery are found in the art [Adjei et al. (1990) Pharmaceutical Research, 7:565-569; Adjei et al. (1990) International Journal of Pharmaceutics, 63:135-144 (leuprolide acetate); Braquet et al (1989), Journal of Cardiovascular Pharmacology, 13(suppl. 5):143-146 (endothelin-1); Hubbard et al. (1989) Annals of Internal Medicine, Vol. III, pp. 206-212 (.alpha.-1-antitrypsin); Smith et al. (1989) J. Clin. Invest. 84:1145-1146 (.alpha.-1-proteinase); Oswein et al., "Aerosolization of Proteins", Proceedings of Symposium on Respiratory Drug Delivery II, Keystone, Colo., March, (1990) (recombinant human growth hormone); Debs et al. (1988) J. Immunol. 140:3482-3488 (interferon-γ and tumor necrosis factor alpha); Platz et al., U.S. Pat. No. 5,284,656 (granulocyte colony stimulating factor)]. A method and composition for pulmonary delivery of drugs is described in U.S. Pat. No. 5,451,569, issued Sep. 19, 1995 to Wong et al.

All such devices require the use of formulations suitable for the dispensing of adhesin inhibitory agent (or derivative). Typically, each formulation is specific to the type of device employed and may involve the use of an appropriate propellant material, in addition to the usual diluents, adjuvant and/or carriers useful in therapy. Also, the use of liposomes, microcapsules or microspheres, inclusion complexes, or other types of carriers is contemplated. Chemically modified adhesin inhibitory agent may also be prepared in different formulations depending on the type of chemical modification or the type of device employed.

Formulations suitable for use with a, nebulizer, either jet or ultrasonic, will typically comprise adhesin inhibitory agent (or derivative) dissolved in water at a concentration of about 0.1 to 25 mg of biologically active adhesin inhibitory agent per ml of solution. The formulation may also include a buffer and a simple sugar (e.g., for adhesin inhibitory agent stabilization and regulation of osmotic pressure). The nebulizer formulation may also contain a surfactant, to reduce or prevent surface induced aggregation of the adhesin inhibitory agent caused by atomization of the solution in forming the aerosol.

Formulations for use with a metered-dose inhaler device will generally comprise a finely divided powder containing the adhesin inhibitory agent (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

The liquid aerosol formulations contain adhesin inhibitory agent and a dispersing agent in a physiologically acceptable diluent. The dry powder aerosol formulations of the present invention consist of a finely divided solid form of adhesin inhibitory agent and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of pulmonary administration of a drug are well known in the art, and manipulation of formulations, aerosolization means and construction of a delivery device require at most routine experimentation by one of ordinary skill in the art. In a particular embodiment, the mass median dynamic diameter will be 5 micrometers or less in order to ensure that the drug particles reach the lung alveoli [Wearley, L. L. (1991) Crit. Rev. in Ther. Drug Carrier Systems 8:333]. Systems of aerosol delivery, such as the pressurized metered dose inhaler and the dry powder inhaler are disclosed in Newman, S. P., Aerosols and the Lung, Clarke, S. W. and Davia, D. editors, pp. 197-22 and can be used in connection with the present invention.

In a further embodiment, as discussed in detail infra, an aerosol formulation of the present invention can include other therapeutically or pharmacologically active ingredients in addition to adhesin inhibitory agent, such as but not limited to an antibiotic, a steroid, a non-steroidal anti-inflammatory drug, etc.

Liquid Aerosol Formulations. The present invention provides aerosol formulations and dosage forms for use in treating subjects suffering from bacterial, e.g., streptococcal, in particularly streptococcal, infection. In general such dosage forms contain adhesin inhibitory agent in a pharmaceutically acceptable diluent. Pharmaceutically acceptable diluents include but are not limited to sterile water, saline, buffered saline, dextrose solution, and the like. In a specific embodiment, a diluent that may be used in the present invention or the pharmaceutical formulation of the present invention is phosphate buffered saline, or a buffered saline solution generally between the pH 7.0-8.0 range, or water.

The liquid aerosol formulation of the present invention may include, as optional ingredients, pharmaceutically acceptable carriers, diluents, solubilizing or emulsifying agents, surfactants and excipients. The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure. Examples of the agents include but are not limited to salts, such as sodium chloride, or potassium chloride, and carbohydrates, such as glucose, galactose or mannose, and the like.

The present invention further contemplates liquid aerosol formulations comprising adhesin inhibitory agent and another therapeutically effective drug, such as an antibiotic, a steroid, a non-steroidal anti-inflammatory drug, etc.

Aerosol Dry Powder Formulations. It is also contemplated that the present aerosol formulation can be prepared as a dry powder formulation comprising a finely divided powder form of adhesin inhibitory agent and a dispersant.

Formulations for dispensing from a powder inhaler device will comprise a finely divided dry powder containing adhesin inhibitory agent (or derivative) and may also include a bulking agent, such as lactose, sorbitol, sucrose, or mannitol in amounts which facilitate dispersal of the powder from the device, e.g., 50 to 90% by weight of the formulation. The adhesin inhibitory agent (or derivative) should most advantageously be prepared in particulate form with an average particle size of less than 10 mm (or microns), most preferably 0.5 to 5 mm, for most effective delivery to the distal lung. In another embodiment, the dry powder formulation can comprise a finely divided dry powder containing adhesin inhibitory agent, a dispersing agent and also a bulking agent. Bulking agents useful in conjunction with the present formulation include such agents as lactose, sorbitol, sucrose, or mannitol, in amounts that facilitate the dispersal of the powder from the device.

The present invention further contemplates dry powder formulations comprising adhesin inhibitory agent and another therapeutically effective drug, such as an antibiotic, a steroid, a non-steroidal anti-inflammatory drug, etc.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: Modern Pharmaceutics Edited by G. S. Banker and C. T. Rhodes Chapter 10, 1979, herein incorporated by reference. In general, the formulation will include the component or components (or chemically modified forms thereof) and inert ingredients which allow for protection against the stomach environment, and release of the biologically active material in the intestine.

Also specifically contemplated are oral dosage forms of the above derivatized component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Abducts" In: Enzymes as Drugs, Hocenberg and Roberts, eds., Wiley-Interscience, New York, N.Y., pp. 367-383; Newmark, et al. (1982) J. Appl. Biochem. 4:185-189. Other polymers that could be used are poly-1,3-dioxolane and poly-1,3,6-trioxocane. Preferred for pharmaceutical usage, as indicated above, are polyethylene glycol moieties.

For the component (or derivative) the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), BPMCP 50, BPMCP 55, polyvinyl acetate phthalate (PVAP), EUDRAGIT L30D, AQUATERIC, cellulose acetate phthalate (CAP), EUDRAGIT L, EUDRAGIT S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The peptide therapeutic can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextran and starch. Certain inorganic salts may be also be used as fillers including calcium triphosphate, magnesium carbonate and sodium chloride. Some commercially available diluents are Fast-Flo, EMDEX, STA-Rx 1500, EMCOMPRESS and AVICEL.

Disintegrants may be included in the formulation of the therapeutic into a solid dosage form. Materials used as disintegrates include but are not limited to starch, including the commercial disintegrant based on starch, EXPLOTAB. Sodium starch glycolate, AMBERLITE, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An antifrictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular eights, CARBOWAX 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the polypeptide (or derivative) are for instance the fatty acids oleic acid, linoleic acid and linolenic acid.

Pulmonary Delivery. Also contemplated herein is pulmonary delivery of the present polypeptide (or derivatives thereof). The polypeptide (or derivative) is delivered to the lungs of a mammal while inhaling and coats the mucosal surface of the alveoli. Other reports of this include Adjei et al. (1990) Pharmaceutical Research 7:565-569; Adjei et al.

(1990) International Journal of Pharmaceutics 63:135-144 (leuprolide acetate); Braquet et al. (1989) Journal of Cardiovascular Pharmacology, 13 (suppl. 5):143-146 (endothelin-1); Hubbard et al. (1989) Annals of Internal Medicine, Vol. III, pp. 206-212 (a1-antitrypsin); Smith et al. (1989) J. Clin. Invest. 84:1145-1146 (a-1-proteinase); Oswein et al. (1990) "Aerosolization of Proteins", Proceedings of Symposium on Respiratory Drug Delivery II, Keystone, Colo., March, (recombinant human growth hormone); Debs et al. (1988) J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Formulations suitable for use with a nebulizer, either jet or ultrasonic, will typically comprise polypeptide (or derivative) dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the protein caused by atomization of the solution in forming the aerosol.

Formulations for use with a metered-dose inhaler device will generally comprise a finely divided powder containing the polypeptide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing polypeptide (or derivative) and may also include a bulking agent, such as lactose, sorbitol, sucrose, or mannitol in amounts which facilitate dispersal of the powder from the device, e.g., 50 to 90% by weight of the formulation. The protein (or derivative) should most advantageously be prepared in particulate form with an average particle size of less than 10 mm (or microns), most preferably 0.5 to 5 mm, for most effective delivery to the distal lung.

Nasal Delivery. Nasal or nasopharyngeal delivery of the polypeptide (or derivative) is also contemplated. Nasal delivery allows the passage of the polypeptide directly over the upper respiratory tract mucosal after administering the therapeutic product to the nose, without the necessity for deposition of the product in the lung. Formulations for nasal delivery include those with dextran or cyclodextran, tide nomenclature, J. Biol. Chem., 243:3552-59 (1969), abbreviations for amino acid.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of about binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Identification of Group B *Streptococcus* Genes

Comparing the genetic and phenotypic composition of genetically-related groups of a bacterial species facilitates identifying virulence factors present in the most pathogenic groups. Type III GBS can be subdivided into three groups of related strains based on the analysis of restriction digest patterns (RDPs) produced by digestion of chromosomal DNA with Hind III and Sse 8387 (5, 6). Over 90% of invasive type III GBS disease in neonates in Japan and in Salt Lake City is caused by bacteria from one of three RDP types, termed RDP type III-3, while RDP type III-2 are significantly more likely to be isolated from vagina than from blood or CSF (6). These results suggest that this genetically-related cluster of type III-3 GBS are more virulent than III-2 strains and could be responsible for the majority of invasive type III disease globally. We proposed that bacterial factors that contribute to the increased virulence of III-3 strains can be identified by characterizing the differences between the genetic composition of III-3 and III-2 strains. Such genetic differences will be found in the bacterial chromosomes since these strains do not contain plasmids (6).

To identify genes present in virulent type III-3 GBS strains and not in the avirulent type III-2 strains we used a modification of the technique described by Lisitsyn et al (7). High molecular weight genomic DNA from an invasive RDP type III-3 GBS strain (strain 874391) and a colonizing ("avirulent") RDP type III-2 strain (strain 865043) was prepared by cell lysis with mutanolysin and Proteinase K digestion (5). For genetic subtraction, genomic DNA from both strains was digested with Taq I. Taq I-digested DNA from the virulent strain was mixed with two complementary oligonucleotides (TaqA (5'-CTAGGTGGATCCTTCGGCAAT-3' (SEQ ID NO: 11)) and TaqB (5'-CGATTGCCGA-3' (SEQ ID NO: 12)), heated to 50° C. for 5 minutes, then allowed to cool slowly to 16° C. in T4 ligase buffer. Oligonucleotides were ligated to the virulent strain DNA by incubation with 20 units of T4 ligase at 16° C. for 12 hours. After ligation, 500 ng of DNA from the virulent strain, with ligated linkers, and 40 ug of DNA from the avirulent strain, without linkers, was mixed together, denatured by heating, and hybridized at 68° C. for 20 hours.

Ten percent of the resulting hybridization mixture was incubated with Taq DNA polymerase and dNTPs to fill in the ends of annealed virulent strain DNA. The hybridized DNA was amplified by Taq DNA polymerase for 10 cycles using the TaqA oligonucleotide as the forward and reverse amplification primer. After amplification, single stranded products remaining after amplification were digested with mung bean nuclease. Twenty percent of the resulting product was then reamplified for 20 cycles. This process of subtraction followed by PCR amplification results in enhanced amplification of DNA segments from the III-3 strains that do not hybridize with DNA segments from the III-2 strains.

A total of four cycles of subtraction and amplification were carried out, using successively smaller quantities of III-3 specific PCR products and alternating two sets of adaptors (TaqA/B (SEQ ID NOS: 11 and 12, respectively) and TaqE/F (TagE (5'-AGGCAACTGTGCTAACCGAGGGAAT-3' (SEQ ID NO:13)); and TaqF (5'-CGATTCCCTCG-3' (SEQ ID NO:14)). The final amplification products were ligated into pBS KS+ vectors. Thirteen clones were randomly selected for analysis. These probes were used in slot and dot blot experiments to determine whether subtraction was successful and to identify probes hybridizing with all III-3 strains. Each of the 6 unique probes hybridized with the parental III-3 virulent strain, while none of the probes hybridized with the avirulent III-2 strains. Two of the amplified sequence tags (clones DY1-1 and DY1-11) hybridized with genomic DNA from all 62 type III isolates, but did not hybridize with DNA prepared from the III-2 and III-1 isolates (FIG. 1). To obtain additional sequence information, we constructed a genomic GBS III-3 library. Multiple plaques hybridizing with each of the III-GBS-specific probes have been purified for further characterization.

Results

The spb Locus

Three overlapping genomic clones hybridizing with probe DY1-1 were identified. A 6.4 kb Sal I-Bgl II fragment present in each clone was subcloned and sequenced. This genomic DNA is present in all RDP type III-3 strains but not in serotype III-2, III-1 or other GBS serotype strains.

Over 90% of this genomic DNA fragment has been sequenced and found to contain 5 open reading frames (ORFs). Two ORFs appear to be candidates for virulence genes. spb1 is a 1509 by ORF. The predicted protein (502 amino acids and Mr 53,446) has the characteristics of a cell-wall bound protein. The nucleic acid and predicted amino acid sequences of sbp1 are provided, in SEQ ID NOS: 5 and 16, respectively. The N-terminus of the predicted protein is a hydrophilic, basic stretch of 6 amino acids followed by a 23 amino acid hydrophobic, proline-rich core, consistent with a signal peptide. The hydrophilic mature protein terminates in a typical LPXTG (SEQ ID NO:17) domain that immediately precedes a hydrophobic 20 amino acid core and a short, basic hydrophilic terminus. The nucleotide sequence is not homologous to sequences of other known bacterial genes. The translated amino acid sequence, however, shares segmental homology with a number of characterized proteins, including the fimbrial type 2 protein of *Actinomyces naeslundii* (27% identity over 350 amino acids) and the fimbrial type I protein of *Actinomyces viscosus* (25% homology over 420 amino acids) (16), the T6 surface protein of *S. pyogenes* (23% identity over 359 amino acids) (20), and the hsf (27% identity over 260 amino acids) and HMW1 adhesins (25% identity over 285 amino acids) of *Haemophilus influenzae* (21, 22). The function of the *S. pyogenes* T6 protein is unknown. Each of the other homologs plays a role in bacterial adhesion and/or invasion.

A spb1$^-$ isogenic deletion mutant GBS strain was created by homologous recombination (using the method as described in Example 2 below) and the ability of the spb1$^-$ mutant to adhere to and invade A549 respiratory epithelial cells was determined. Compared to the wild type strain, the number of spb1$^-$ bacteria adherent to A549 monolayers was reduced by 60.0% ($p<0.01$) and the number of intracellular invading bacteria was reduced by 53.6% ($p<0.01$). This data suggests spb1 may contribute to the pathogenesis of GBS pneumonia and bacterial entry into the bloodstream.

The second ORF, spb2, terminates 37 by upstream from spb1 and is in the same transcriptional orientation. This 1692 by ORF has a deduced amino acid sequence of 579 residues and Mr 64,492. The nucleic acid and predicted amino acid sequences of sbp2 are provided in SEQ ID NOS:18 and 19, respectively. spb2 shares 50.5% nucleic acid identity and 20.7% amino acid identity with spb1. Conservation is highest in the carboxy-terminal regions, including a shared LPSTGG (SEQ ID NO:20) motif. In contrast to spb1, spb2 does not have a obvious signal sequence. Its secretion may be mediated by carboxy-terminal recognition sequences or by accessory peptides (23). The deduced amino acid sequence of Spb2 is also homologous with *S. pyogenes* T6 and *Actinomyces naeslundii* proteins, and to *Listeria monocytogenes* internalin A (22% identity over 308 amino acids); again, proteins important in adhesion and invasion (24).

The ema Locus

Two genomic clones hybridizing with probe DY1-11 were identified. A 7 kb Hind III fragment present in each clone was subcloned and sequenced. Unlike the serotype III specific spb sequences, this genomic DNA, which is adjacent to a region of serotype III-3 specific DNA, was found to be present in all GBS tested to date, including serotype Ia, Ib, II and V strains. This region of the GBS chromosome, which we have designated the extracellular matrix adhesin (ema) locus, contains 5 significant ORFs.

emaA

The first ORF, emaA, is 738 by long, with a predicted protein product of 246 amino acids and Mr 26.2. The nucleic acid sequence (SEQ ID NO:1) and predicted amino acid sequence (SEQ ID NO:2) of emaA are shown in FIG. 2. The EmaA protein is a non-repetitive protein. The 27 amino acid N-terminus of the predicted protein is consistent with a signal peptide. The mature protein has an imperfect cell wall binding domain (XPXTGG (SEQ ID NO:21)) followed by a transmembrane spanning domain encompassing residues 219-235 and a terminal hydrophilic tail. The emaA nucleotide sequence is not homologous to known sequences of bacterial genes. The translated amino acid sequence, however, shares segmental homology with a number of characterized proteins, including a collagen adhesin, Bbp, of *Staphylococcus aureus* (37% identity over 103 aa) (15), a type 2 fimbrial structural subunit of *Actinomyces naeslandii* (39% homology over 112 aa) (16), and the FimP protein of *Actinomyces viscosus* (28% homology over 228 aa) (17). The function of the *S. pyogenes* T6 protein is unknown. The type 1 and type fimbria of *Actinomyces* mediate bacterial adhesion to salivary glycoproteins and various host cells, contributing to the pathogenesis of dental caries.

emaB

The second ORF, emaB, begins 94 by 3' of emaA and is in the same transcriptional orientation. The nucleic acid sequence (SEQ ID NO:3) and predicted amino acid sequence (SEQ ID NO:4) of emaB are shown in FIG. 3. It is 924 by long with a predicted protein product of 308 amino acids and Mr 33.9. The predicted EmaB protein is a nonrepetitive protein. The 27 amino acids N-terminus of the predicted protein is consistent with a signal peptide. The mature protein has an imperfect cell wall binding domain (XPXTG) followed by a transmembrane spanning domain encompassing residues 279-294. The emaB nucleotide sequence is not homologous to known sequences of bacterial genes. The translated amino acid sequence, however, shares segmental homology with a number of characterized proteins, including a type 2 fimbrial structural subunit of *Actinomyces naeslandii* (28% homology over 222 amino acids), the T6 protein of *S. pyogenes* (26% homology over 266 amino acids) (20), and a *S. epidermidis* putative cell-surface adhesin (24% identity over 197 amino acids). The first of these proteins mediates adhesion of *S. aureus* to collagen and is postulated to contribute to the pathogenesis of osteomyelitis and infectious arthritis.

emaC

The third ORF, emaC, begins 2 by 3' of emaB and is the same transcriptional orientation. It is 918 by long, with a predicted protein product of 305 amino acids and Mr 34.5. The nucleic acid sequence (SEQ ID NO:5) and predicted amino acid sequence (SEQ ID NO:6) of emaC are depicted in FIG. 4. The EmaC protein is a nonrepetitive protein. The 30 amino acid N-terminus of the predicted protein is consistent with a signal peptide. The mature protein has a transmembrane spanning domain encompassing residues 265-281. The emaC nucleotide sequence is not homologous to known sequences of bacterial genes. The translated amino acid sequence, however, shares segmental homology with a number of characterized proteins, including proteins associated with the assembly of type 2 fimbrial structural subunit of *Actinomyces naeslandii* (38% homology over 234 amino acids) (16). These proteins are required for the assembly of type 2 fimbria.

emaD

The fourth ORF, emaD, is 852 by long, overlaps emaC by 47 bp, and is in the same transcriptional orientation. The predicted protein product is 284 amino acids and Mr 33.1. The nucleic acid sequence (SEQ ID NO:7) and predicted amino acid sequence (SEQ ID NO:8) of emaD are shown in FIG. 5. No identifiable N-terminal signal sequence is present and potential transmembrane segments are present at positions 19-35 and 252-280. The mature protein is not repetitive and lacks a cell wall binding domain. The emaD nucleotide sequence is not homologous to known sequences of bacterial genes. The translated amino acid sequence, shares segmental homology with the same fimbria-associated proteins of *Actinomyces* as does EmaC.

emaE

The fifth ORF, emaE, begins 42 by 3' of emaD and is in the same transcriptional orientation. It is 2712 by long, with a predicted protein product of 904 aa and Mr 100.9. FIG. 6 depicts the nucleic acid sequence (SEQ ID NO:9) and predicted amino acid sequence (SEQ ID NO:10) of emaE. The predicted EmaE protein is a nonrepetitive protein. An obvious N-terminal signal peptide is not evident but a putative transmembrane region is located at residues 24-40. The mature protein has an imperfect cell wall binding domain (XPXTGG (SEQ ID NO: 21)) followed by a transmembrane spanning domain encompassing residues 880-896. The emaE nucleotide sequence is not homologous to known sequences of bacterial genes. The translated amino acid sequence, however, shares segmental homology with a number of characterized proteins, including the F1 and F2 fibronectin binding proteins of *S. pyogenes* (31% homology over 207 amino acids) (18, 19). These proteins mediate high affinity binding to fibronectin, and are important in the adhesion of *S. pyogenes* to respiratory cells.

The similarity of the protein products of the ema locus to physiologically important adhesins and invasins of other bacterial species suggests that the Ema proteins have a role in facilitating the adhesion of GBS to extracellular matrix components and to cell surfaces and subsequent invasion of epithelial and endothelial cells, the initial steps in the pathogenesis of infection.

Several lines of evidence suggest the members of the ema and the spb locus may have similar functions, but are likely to represent distinct classes of proteins. The ema and spb locus genes are each and all similar to physiologically important adhesions and invasions of the bacterial species, however, both Spb1 and Spb2 have prototypical gram positive cell-wall binding domains, whereas the members of the ema locus have an unusual motif, suggesting a distinct mechanism of cell surface anchoring. Second, the spb locus is restricted to virulent serotype III-3 strains of GBS, whereas the ema locus appears to be ubiquitous in all GBS serotypes. Third, spb1 and spb2 are more homologous to one another than to members of the ema locus and ema genes are more closely homologous to one another than to spb1 and spb2.

Example 2

Biologic Characterization of Novel GBS Genes

Isogenic Mutant Bacterial Strains

To identify biologic activity of these novel GBS genes, isogenic mutant bacterial strains are created which are identical in all respects except for the presence or absence of a particular gene. Deletion mutants are created by allelic replacement. The relevant gene, with 100-300 by of flanking sequences, is subcloned and modified by the deletion of an intragenic portion of the coding sequence and, in some cases, the insertion of a kanamycin resistance gene. The mutant gene is cloned into the suicide vector pHY304 (kindly provided by Dr. Craig Rubens), a broad host range plasmid containing a temperature sensitive ori, erythromycin resistance gene ($erm^{TS}$), and a pBS multiple cloning site. The pHY304 vector is a derivative of the vector pWV01 (Framson, P. E. et al (1997) Applied Environ Microbiology 63:3539-3547). Plasmids containing mutant genes are electroporated into strain 874391 and single cross-over mutants are selected by antibiotic resistance at 37° C. The resulting antibiotic resistant colonies are subjected to a temperature shift to 30° C. Integration of the plasmid is unstable at this permissive temperature because there are two functional ori's on the chromosome. Excised plasmid is eliminated by growth on nonselective media for many generations, then colonies are screened for the presence of the mutant allele by erythromycin-sensitivity. Double-crossover mutants are stable and do not require maintenance under drug selection. The mutant genotype is confirmed by Southern blotting or PCR demonstrating the appropriate deletion. The resulting mutants are screened for the presence of gene expression by Northern and Western blot analysis. The phenotype of the knockout mutants is then compared with that of the wild type strain 874391 by examining growth rate and colony morphology, and the expression of β-hemolysin and CAMP factor. Surface protein expression is assessed by Western blot, using polyclonal sera from rabbits immunized with whole, heat-killed type III GBS.

In Vitro Models

A. Adherence

Adhesion of GBS to host cells is a prerequisite for invasive disease. Three different cell types have the potential to be important in this process: i) adhesion to respiratory epithelial cells is likely to facilitate most early onset neonatal infections, ii) adhesion to gastrointestinal epithelial cells has been postulated to be important in the pathogenesis of late onset neonatal infections, and iii) adhesion to endothelial cells is necessary for both endocarditis and other endovascular infections, and is likely to be the initial event in GBS meningitis. The ability of wild type and mutant strains to adhere to epithelial and endothelial cells is compared in adhesion assays.

Four different cell lines are used to investigate the role of novel GBS genes in adhesion. GBS adhere to and invade A549 human alveolar epithelial carcinoma cells and surface proteins appear to play an important role in this process (8). GBS binding to A549 cells is used as an in vitro model for respiratory colonization. GBS also adhere to C2BBeL, a human intestinal epithelial cell line, which is used as a model for gastrointestinal colonization, and to HeLa cervical epithelial cells, a model for genital colonization and maternal infection. For endothelial adhesion, two cell lines are studied: freshly isolated human umbilical vein endothelial (HUVE) cells; and an immortalized human brain microvascular endothelial cell line (BMEC). Adhesion assays are performed as described by Tamura et al (9). Cell lines are grown to confluence in 96-well tissue culture plates in recommended media. Monolayers are washed with PBS and fixed with 0.5% gluteraldehyde. Following blocking with 5% BSA in PBS, cells are inoculated with various inocula of GBS, centrifuged for 10 minutes at 2000 rpm and incubated for 1 hour at 4° C. Nonadherent bacteria are removed by washing three times with 5% nonfat dry milk in PBS and bound bacteria are then eluted and plated quantitatively.

B. Invasion

GBS adhere to and invade respiratory epithelium, endothelium and BMEC (8, 10, 11). The ability of wild type and isogenic mutant GBS strains to invade the above epithelial and endothelial cells are tested as previously described (8, 10, 11). Assays that distinguish the ability of GBS to invade eukaryotic cells versus adhere to cells capitalize on the inability of penicillin and gentamicin to enter host cells, allowing quantification of intracellular bacteria after extracellular bacteria are killed. GBS are grown to the desired growth phase in TH broth, washed twice with PBS and resuspended in tissue culture media containing 10% fetal calf serum. Tissue culture monolayers grown to confluence in 24-well plates are inoculated with varying inocula of GBS, centrifuged at 800×g and incubated at 37° C. in 5% $CO_2$ for 2-6 hours. Extracellular bacteria are removed by washing four times with PBS. Cells are then incubated in fresh medium with 5 mg/ml penicillin and 100 mg/ml gentamicin for 2 hours. Media is then removed, monolayers washed, and cells lysed by treatment with 0.025% TRITON X-100. Cell lysates are sonicated to disrupt bacterial chains and aliquots plated quantitatively.

C. Antibody to GBS Proteins

The ability of specific antibody to the novel GBS proteins to promote opsonophagocytic killing of GBS is tested (12). Rabbits are immunized with recombinant or purified GBS proteins produced by standard techniques. Rabbit antiserum of different dilutions (ranging from 1/50 to 1/5,000) that has been exhaustively absorbed with the relevant isogenic mutant strain at 4° C. will be incubated with GBS in the presence of human complement and polymorphonuclear leukocytes ($3\times10^6$). Opsonophagocytic killing is expressed as the log number of CFU surviving following 1 hour of incubation subtracted from the log of the number of CFU at the zero time point. Killing of wild type strains is compared to that of isogenic mutants lacking novel GBS proteins.

In vivo Models

The neonatal rat has been used by numerous laboratories as a model of GBS infection because it closely mimics human neonatal infection (13). The contribution of novel genes to the pathogenesis of GBS infections is tested by comparing wild type and mutant in this system. Rat pups are inoculated by two routes. First, pups are inoculated intranasally to mimic the respiratory infection and sepsis typical of early onset GBS infection. Secondly, intraperitoneal or subcutaneous inoculation reproduces the high grade bacteremia associated with GBS sepsis and that precedes GBS meningitis (14).

Rat pups are inoculated with varying doses of GBS strains and mortality is determined. The level of bacteremia is determined by quantitative blood cultures. Lung, liver, spleen and meningeal tissue are preserved for histologic examination.

The ability of antiserum to the GBS proteins to protect neonatal rats from GBS infection is tested (13). Newborn rats (<18 hours old) receive an intraperitoneal injection of 0.5 ml of undiluted rabbit antiserum, followed by the intraperitoneal inoculation of the equivalent of one LD50 unit of GBS (usually about 5000 bacteria) in PBS. Mortality and morbidity are then determined.

Role of Novel GBS Proteins in Vaccines

Several surface proteins of GBS, including C and Rib are immunogenic and protective against GBS infection in infant rodent models (25, 26). None of these proteins are present in all GBS strains (27). Furthermore, each of these proteins has a repetitive structure. The phenotypic variability of these repetitive proteins allows escape mutants expressing variant forms to evade host immune systems and may limit the effectiveness of these vaccines (28). It is notable that each of the predicted proteins of the spb and ema loci do not have a repetitive structure and would not have this disadvantage.

The novel GBS proteins we describe here may be useful antigens for a GBS vaccine. The data presented herein indicates these proteins have a role in mediating adhesion to and invasion of GBS to human epithelial cells, thus antibody against these antigens may prevent these initial steps in infection. It is highly desirable to develop a vaccine that prevents colonization of pregnant women and other individuals at increased risk of invasive GBS infection, as this would eliminate most infections. Our data suggests that antibody against Spb 1 is effective in reducing colonization or infection following colonization with highly virulent strains of serotype III, and therefore this protein is a particularly useful vaccine antigen. Members of the ema locus, unlike spb 1 and spb2, are ubiquitous in GBS and therefore have a role in the prevention of infection by multiple serotypes of GBS. An optimal vaccine formulation includes combinations of these antigens.

Two strategies are used to design GBS vaccines using these novel proteins. First, purified recombinant or affinity-purified proteins are used as vaccine antigens, singly or in combination (25). Second, these proteins are used as carrier proteins for capsular polysaccharide or oligosaccharide-based vaccines. GBS polysaccharides and oligosaccharides are generally poorly immunogenic and fail to elicit significant memory and booster responses (29). Conjugation of these polysaccharides or oligosaccharides to protein carriers increases immunogenicity. GBS polysaccharide conjugated to tetanus toxoid, for example, has been used to immunize pregnant women and results in high levels of maternal serum anti-polysaccharide antibody which may be transferred to the fetus in the third trimester of pregnancy (30). Selection of appropriate carrier proteins is important for the development of polysaccharide-protein vaccine formulations. For example, *Haemophilus influenzae* type b poly- or oligosaccharide conjugated to different protein carriers has variable immunogenicity and elicits antibody with varying avidity (31, 32). Repeated immunization with the same carrier protein may also suppress immune responses by competition for specific B cells (epitopic suppression) or other mechanisms. This is of particular concern for the development of GBS vaccines since recently developed polysaccharide and oligosaccharide-protein conjugate vaccines against the bacteria *H. influenzae, S. pneumoniae*, and *N. meningitidis* all utilize a restricted number of carrier proteins (tetanus toxoid, CRM 197, diptheria toxoid), increasing the number of exposures to these carriers an individual is likely to receive. A "designer" vaccine, composed of a GBS polysaccharide or oligosaccharide coupled to a GBS-specific carrier protein, such as the novel GBS polypeptides, provided herein, particularly including Spb1, EmaC and EmaE, may be a preferable strategy. The large size of certain of these novel GBS antigens may also be an advantage to traditional carrier proteins as increasing size is associated with improved immunogenicity.

Example 3

EMA Homologs in Streptococci and Other Bacteria

As noted above, the GBS Ema proteins share segmental homology with certain characterized proteins from other bacterial species, including bacterial adhesion and invasion proteins. The segmental homolog is noted as in the range of 24-39%. In addition, the Ema proteins demonstrate some homology to one another. A comparison of the ema genes shows that EmaA and EmaB are 47% homologous, however, due to the difference in their predicted lengths it is necessary to insert gaps in the EmaA sequence in order to line them up. The two Ema proteins which are most similar in structure, EmaC and EmaD share 48.7% amino acid homology to one another. EmaA/B, EmaC/D and EmaE are each ≦20% homologous to one another.

The ema sequences were used to search the unannotated microbial genomes (Eubacteria). The predicted Ema proteins were searched against translations in all six frames (tblast x) of finished and unfinished unannotated microbial genomes available at the web site of the National Center for Biotechnology Information (NCBI). Segmental amino acid homolog was identified.

EmaA has some segmental homolog with *S. pneumoniae, E. faecalis, B. anthiacis* and *C. diptheriae*. Ema B has some segmental homolog with *B. anthracis*. EmaE has segmental homology to *S. pyogeizes* and lesser homology to *B. anthracis*.

Significant homology was identified between the GBS EmaC and EmaD and proteins in other bacterial species. EmaC has significant (55% identity over 149 amino acids) homology to a region of the *S. pneumoniae* chromosome and the *S. pyogenes* chromosome (47% identity over 150 amino acids). Lesser segmental homology was found to *E. faecalis, S. equi*, and *C. diptheriae*. EmaD has strong segmental homology (66% over 184 amino acids) to a region of the *S. pneumoniae* chromosome, and lesser segmental homology to *C. diphtheriae* and *S. pyogenes*.

We have identified two Ema homologs in *S. pneumoniae*. These *S. pneumoniae* homologs show homology to EmaC and EmaD and, like EmaC and EmaD, also demonstrate homology to fimbria-associated protein of *Actinomyces*. The encoding nucleic acid and predicted amino acid sequence of the first *S. pneumoniae* EmaC/D homolog are provided in SEQ ID NOS:24 and 23, respectively. The genome region nucleic acid including the first homolog encoding sequence is provided in SEQ ID NO:22. The nucleic acid and predicted amino acid sequence of the second *S. pneumoniae* EmaC/D homolog are provided in SEQ ID NOS:27 and 26 respectively. The genomic region nucleic acid of this second homolog is found in SEQ ID NO:25. An EmaC/D homolog has been identified in *Enterococcus faecalis* by search and analysis. The *E. faecalis* EmaC/D homolog predicted amino acid sequence is provided in SEQ ID NO:29. The nucleic acid sequence encoding this *E. faecalis* Ema homolog is provided in SEQ ID NO:30. The nucleic acid sequence of *E. faecalis* which genomic region encodes the EmaC/D homolog is provided in SEQ ID NO:28.

We have also identified an EmaD homolog in *Corynebacterium diptheriae*. The predicted amino acid sequence of the *C. diptheriae* EmaD homolog is provided in SEQ ID NO:32. *C. diptheriae* nucleic acid sequence which encodes the homolog is found in SEQ ID NO:33. The corresponding genomic region sequence of *C. diptheriae* is provided in SEQ ID NO: 31.

A predicted EmaC/D homolog has been identified in *S. pyogenes*. The predicted partial amino acid sequence of this Ema homolog provided in SEQ ID NO:37.

A region of amino acids TLLTCTPYMINS/THRLLVR/KG (SEQ ID NO:34) is found in GBS EmaC, GBS EmaD, in both the EmaC/D homologs of *S. pneunoniae*, and in the *E. faecalis* Ema homolog. A similar sequence TLVTCTPYGINTHRLLVTA (SEQ ID NO:35) is also found in the *C. diptheriae* Ema homolog. The *S. pyogenes* predicted Ema homolog has a similar sequence TLVTCTPYGVNTKRLLVRG (SEQ ID NO:36) as well.

The following is a list of the references referred to in this Example section.

REFERENCES

1 Baker C J. Group B streptococcal infections. In Streptococcal infections. Clinical aspects, microbiology, and molecular pathogenesis. (D. L. Stevens and E. L. Kaplan), New York: Oxford University Press, 222-237, 2000.

2 Blumberg H M, Stephens D S, Modansky M, Erwin M, Elliot J, Facklam R R, Schuchat A, Baughman W and Farley M M. Invasive group B streptococcal disease: The emergence of serotype V. Journal of Infectious Diseases 173:365-373, 1996.

3 Kogan G, Uhrin D, Brisson J-R, Paoletti L C, Blodgett A E, Kasper D L and Jennings H J. Structural and immunochemical characterization of the type VIII group B *Streptococcus* capsular polysaccharide. The Journal of Biological Chemistry 271:8786-8790, 1996.

4 Rubens C E, Raff H V, Jackson C J, Chi E Y, Bielitzki J T and Hillier S L. Pathophysiology and histopathology of group B streptococcal sepsis in *Macaca nemestrina* primates induced after intraamniotic inoculation: evidence for bacterial cellular invasion. Journal of Infectious Diseases 164: 320-330, 1991.

5 Nagano Y, Nagano N, Takahashi S, Murono K, Fujita K, Taguchi F and Okuwaki Y. Restriction endonuclease digest patterns of chromosomal DNA from group B b-haemolytic streptococci. Journal of Medical Microbiology 35:297-303, 1991.

6 Takahashi S, Adderson E E, Nagano Y, Nagano N, Briesacher M R and Bohnsack J F. Identification of a highly encapsulated, genetically related group of invasive type III group B streptococci. The Journal of Infectious Diseases 177:1116-1119, 1998.

7 Lisitsyn N, Lisitsyn N and Wigler M. Cloning the differences between two complex genomes. Science 259:946-951, 1993.

8 Rubens C E, Smith S, Hulse M, Chi E Y and van Belle G. Respiratory epithelial cell invasion by group B streptococci. Infection & Immunity 60:5157-63, 1992.

9 Tamura G S, Kuypers J M, Smith S, Raff H and Rubens C E. Adherence of group B streptococci to cultured epithelial cells: roles of environmental factors and bacterial surface components. Infection and Immunity 62:2450-8, 1994.

10 Nizet V, Kim K S, Stins M, Jonas M, Chi E Y, Nguyen D and Rubens C E. Invasion of bran microvascular endothelial cells by group B streptococci. Infection and Immunity 65:5074-5081, 1997.

11 Gibson R L, Lee M K, Soderland C, Chi E Y and Rubens C E. Group B streptococci invade endothelial cells: type III capsular polysaccharide attenuates invasion. Infection & Immunity 61:478-85, 1993.

12 Gravekamp C, Kasper D L, Michel J L, Kling D E, Carey V and Madoff L C. Immunogenicity and protective efficacy of the alpha C protein of group B streptococci are inversely related to the number of repeats. Infection and Immunity 65:5216-5221, 1997.

13 Hill H R, Gonzales L A, Knappe W A, Fischer G W, Kelsey D K and Raff H V. Comparative protective activity of human monoclonal and hyperimmune polyclonal antibody against group B streptococci. Journal of Infectious Diseases 163:792-797, 1991.

14 Kim K S, Wass C A and Cross A S. Blood-brain barrier permeability during the development of experimental bacterial meningitis in the rat. Experimental Neurology 145: 253-257, 1997.

15 Patti J M, Jonsson H, Guss B, Switalski L M, Wiberg K, Lindberg M and Hook M. Molecular characterization and expression of a gene encoding a *Staphylococcus aureus* collagen adhesin. The Journal of Biologic Chemistry 267: 47664772, 1992.

16 Yeung M K and Cisar J O, Sequence homology between the subunits of two immunologically and functionally distinct types of fimbrae of *Actinomyces* spp. The Journal of Bacteriology 172:2462-8, 1990.

17 Li T, Johansson I, Hay D I and Stromberg N. Strains of *Actinomyces naeslundii* and *Actinomyces viscosus* exhibit structurally variant fimbrial subunit proteins and bind to different peptide motifs in salivary proteins. Infection and Immunity 67:2053-2059, 1999.

18 Jaffe J, Natanson-Yaron S, Caparon M G and Hanski E. Protein F2, a novel fibronectin-binding protein from *Streptococcus pyogenes*, possesses two binding domains Molecular Microbiology 21:2720-728, 1996.

19 Rocha C L and Fischetti V A. Identification and characterization of a novel fibronectin-binding protein on the surface of Group A streptococci. Infection and Immunity 66:1482-1491, 1999.

20 Schneewind O, Jones K F and Fischetti V A. Sequence and structural characteristics of the trypsin-resistant T6 protein of group A streptococci. The Journal of Bacteriology 172: 3310-7, 1990.

21 St. Geme III J W, Cutter D and Barenkamp S J. Characterization of the genetic locus encoding *Haemophilus influenzae* type b surface fibrils. The Journal of Bacteriology 178:6281-6287, 1996.

22 Barenkamp S J and Leininger E. Cloning, expression, and DNA sequence analysis of genes encoding nontypeable *Haemophilus influenzae* high-molecular-weight surface-exposed proteins related to filamentous hemagglutinin of *Bordatella pertussis*. Infection and Immunity 60:1302-1313, 1992.

23 Micheils T, Wattiau P, Brasseur R, Ruysschaert J M and Cornelis G. Secretion of Yop proteins by Yersiniae. Infection and Immunity 58:2840-2849, 1990.

24 Gaillard J L, Berche P, Frehel C, Gouin E and Cossart P. Entry of *L. monocytogenes* into cells is mediated by internalin, a repeat protein reminiscent of surface antigens from gram-positive cocci. Cell 65:1127-1141, 1991.

25 Madoff L C, Michel J L, Gong E W, Rodewald A K and Kasper D L. Protection of neonatal mice from group B streptococcal infection by maternal immunization with beta C protein. Infection and Immunity 60:49894994, 1992.

26 Stalhammar-Carlemalm M, Stenberg L and Lindahl G. Protein Rib: A novel group B streptococcal cell surface protein that confers protective immunity and is expressed by most strains causing invasive infections. The Journal of Experimental Medicine 177:1593-1603, 1993.

27 Ferrieri P and Flores A E. Surface protein expression in group B streptococcal invasive isolates. Advances in Experimental Medicine 418:635-637, 1997.

28 Madoff L C, Michel J T, Gong E W, Kling D E and Kasper D L. Group B streptococci escape host immunity by deletion of tandem repeat elements of the alpha C protein. Proceedings of the National Academy of Science U.S.A. 93:4131-4136, 196.

29 Baker C J, Rench M A and Edwards M S. Immunization of pregnant women with a polysaccharide vaccine of group B *Streptococcus*. New England Journal of Medicine 319: 1180-1185, 1988.

30 Baker C J, Paoletti L C, Wessels M R, Guttormsen H-K, Rench M A, Hickman M E and Kasper D L. Safety and immunogenicity of capsular polysaccharide-tetanus toxoid conjugate vaccines for group B streptococcal types Ia and Ib. The Journal of Infectious Diseases 179:142-150, 1999.

31 Decker M D, Edwards K M, Bradley R and Palmer P. Comparative trial in infants of four conjugate *Haemophilus influenzae* type b vaccines. The Journal of Pediatrics 120: 184-189, 1992.

32 Schlesinger Y, Granoff D M and Group T V S. Avidity and bactericidal activity of antibody elicited by different *Haemophilus influenzae* type b conjugate vaccines. Journal of the American Medical Association 267:1489-1494, 1992.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. An isolated streptococcal Extracellular Matrix Adhesion Protein E (EmaE) which comprises the amino acid sequence set forth in SEQ ID NO:10.

2. A vaccine comprising an isolated streptococcal polypeptide EmaE comprising the amino acid sequence set forth in SEQ ID NO:10 and a pharmaceutically acceptable adjuvant.

3. The vaccine of claim 2, further comprising an antigen selected from the group consisting of:

a) the polypeptide Spb1 or an immunogenic fragment thereof;

b) the polypeptide Spb2 or an immunogenic fragment thereof;

c) the polypeptide C protein alpha antigen or an immunogenic fragment thereof;

d) the polypeptide Rib or an immunogenic fragment thereof;

e) the polypeptide Lmb or an immunogenic fragment thereof;

f) the polypeptide C5a-ase or an immunogenic fragment thereof;

g) Group B streptococcal polysaccharides or oligosaccharides; and h) any combination of one or more of the foregoing.

4. An immunogenic composition comprising an isolated streptococcal polypeptide EmaE comprising the amino acid sequence set forth in SEQ ID NO:10 and a pharmaceutically acceptable adjuvant.

5. The immunogenic composition of claim 4, further comprising an antigen selected from the group consisting of:

a) the polypeptide Spb1 or an immunogenic fragment thereof;

b) the polypeptide Spb2 or an immunogenic fragment thereof;

c) the polypeptide C protein alpha antigen or an immunogenic fragment thereof;

d) the polypeptide Rib or an immunogenic fragment thereof;

e) the polypeptide Lmb or an immunogenic fragment thereof;

f) the polypeptide C5A-ase or an immunogenic fragment thereof;

g) Group B streptococcal polysaccharides or oligosaccharides; and h) any combination of one or more of the foregoing.

6. A pharmaceutical composition comprising an isolated streptococcal polypeptide EmaE comprising the amino acid sequence set forth in SEQ ID NO:10 and a pharmaceutically acceptable carrier.

7. The pharmaceutical composition of claim 6, further comprising an active ingredient selected from the group consisting of:

a) Spb1 or Spb2 polypeptide;

b) C protein alpha antigen;

c) Rib polypeptide;

d) Lmb polypeptide;

e) C5a-ase polypeptide;

f) a Group B streptococcal polysaccharide or oligosaccharide; and g) an anti-streptococcal vaccine.

8. A method for preventing infection with a bacterium that expresses a streptococcal EmaE polypeptide comprising administering an immunogenically effective dose of the immunogenic composition of claim 4 to a subject.

9. A method for treating infection with a bacterium that expresses a streptococcal EmaE polypeptide comprising administering a therapeutically effective dose of a pharmaceutical composition of claim 6 to a subject.

10. A method of inducing an immune response in a subject which has been exposed to or infected with a streptococcal bacterium comprising administering to the subject an amount of the pharmaceutical composition of claim 6, thereby inducing an immune response.

* * * * *

UNITED STATES PATENT AND TRADEMARK OFFICE

CERTIFICATE OF CORRECTION

PATENT NO. : 8,529,912 B2
APPLICATION NO. : 13/030660
DATED : September 10, 2013
INVENTOR(S) : |Adderson and Bohnsack It is certified that error appears in the above-identified patent and that said Letters Patent is hereby corrected as shown below:

On the Title Page at item (75), delete “Elizabeth”
On the Title Page at item (75), insert -- Elisabeth --

Signed and Sealed this
Seventeenth Day of December, 2013

Margaret A. Focarino
*Commissioner for Patents of the United States Patent and Trademark Office*

SEQUENCE LISTING

<160> NUMBER OF SEQ ID NOS: 37

<210> SEQ ID NO 1
<211> LENGTH: 737
<212> TYPE: DNA
<213> ORGANISM: Streptococcus agalactiae

<400> SEQUENCE: 1

```
atgacccttg ttaaaaatca agatgctctt gataaagcta ctgcaaatac agatgatgcg     60

gcatttttgg aaattccagt tgcatcaact attaatgaaa aagcagtttt aggaaaagca    120

attgaaaata cttttgaact tcaatatgac catactcctg ataaagctga caatccaaaa    180

ccatctaatc ctccaagaaa accagaagtt catactggtg ggaaacgatt tgtaaagaaa    240

gactcaacag aaacacaaac actaggtggt gctgagtttg atttgttggc ttctgatggg    300

acagcagtaa aatggacaga tgctcttatt aaagcgaata ctaataaaaa ctatattgct    360

ggagaagctg ttactgggca accaatcaaa ttgaaatcac atacagacgg tacgtttgag    420

attaaaggtt tggcttatgc agttgatgcg aatgcagagg gtacagcagt aacttacaaa    480

ttaaaagaaa caaaagcacc agaaggttat gtaatccctg ataaagaaat cgagtttaca    540

gtatcacaaa catcttataa tacaaaacca actgacatca cggttgatag tgctgatgca    600

acacctgata caattaaaaa caacaaacgt ccttcaatcc ctaatactgg tggtattggt    660

acggctatct ttgtcgctat cggtgctgcg gtgatggctt ttgctgttaa ggggatgaag    720

cgtcgtacaa aagataa                                                   737
```

<210> SEQ ID NO 2
<211> LENGTH: 245
<212> TYPE: PRT
<213> ORGANISM: Streptococcus agalactiae

<400> SEQUENCE: 2

```
Met Thr Leu Val Lys Asn Gln Asp Ala Leu Asp Lys Ala Thr Ala Asn
1               5                   10                  15

Thr Asp Asp Ala Ala Phe Leu Glu Ile Pro Val Ala Ser Thr Ile Asn
            20                  25                  30

Glu Lys Ala Val Leu Gly Lys Ala Ile Glu Asn Thr Phe Glu Leu Gln
        35                  40                  45

Tyr Asp His Thr Pro Asp Lys Ala Asp Asn Pro Lys Pro Ser Asn Pro
    50                  55                  60

Pro Arg Lys Pro Glu Val His Thr Gly Gly Lys Arg Phe Val Lys Lys
65                  70                  75                  80

Asp Ser Thr Glu Thr Gln Thr Leu Gly Gly Ala Glu Phe Asp Leu Leu
                85                  90                  95

Ala Ser Asp Gly Thr Ala Val Lys Trp Thr Asp Ala Leu Ile Lys Ala
            100                 105                 110

Asn Thr Asn Lys Asn Tyr Ile Ala Gly Glu Ala Val Thr Gly Gln Pro
        115                 120                 125

Ile Lys Leu Lys Ser His Thr Asp Gly Thr Phe Glu Ile Lys Gly Leu
    130                 135                 140

Ala Tyr Ala Val Asp Ala Asn Ala Glu Gly Thr Ala Val Thr Tyr Lys
145                 150                 155                 160

Leu Lys Glu Thr Lys Ala Pro Glu Gly Tyr Val Ile Pro Asp Lys Glu
                165                 170                 175

Ile Glu Phe Thr Val Ser Gln Thr Ser Tyr Asn Thr Lys Pro Thr Asp
```

180 185 190

Ile Thr Val Asp Ser Ala Asp Ala Thr Pro Asp Thr Ile Lys Asn Asn
195 200 205

Lys Arg Pro Ser Ile Pro Asn Thr Gly Gly Ile Gly Thr Ala Ile Phe
210 215 220

Val Ala Ile Gly Ala Ala Val Met Ala Phe Ala Val Lys Gly Met Lys
225 230 235 240

Arg Arg Thr Lys Asp
245

<210> SEQ ID NO 3
<211> LENGTH: 924
<212> TYPE: DNA
<213> ORGANISM: Streptococcus agalactiae

<400> SEQUENCE: 3
atgaaacaaa cattaaaact tatgttttct tttctgttga tgttagggac tatgtttgga 60
attagccaaa ctgttttagc gcaagaaact catcagttga cgattgttca tcttgaagca 120
agggatattg atcgtccaaa tccacagttg gagattgccc ctaaagaagg gactccaatt 180
gaaggagtac tctatcagtt gtaccaatta aaatcaactg aagatggcga tttgttggca 240
cattggaatt ccctaactat cacagaattg aaaaaacagg cgcagcaggt ttttgaagcc 300
actactaatc aacaaggaaa ggctacattt aaccaactac cagatggaat ttattatggt 360
ctggcggtta aagccggtga aaaaaatcgt aatgtctcag ctttcttggt tgacttgtct 420
gaggataaag tgatttatcc taaaatcatc tggtccacag gtgagttgga cttgcttaaa 480
gttggtgtgg atggtgatac caaaaaacca ctagcaggcg ttgtctttga actttatgaa 540
aagaatggta ggactcctat tcgtgtgaaa aatggggtgc attctcaaga tattgacgct 600
gcaaaacatt tagaaacaga ttcatcaggg catatcagaa tttccgggct catccatggg 660
gactatgtct taaaagaaat cgagacacag tcaggatatc agatcggaca ggcagagact 720
gctgtgacta ttgaaaaatc aaaaacagta acagtaacga ttgaaaataa aaaagttccg 780
acacctaaag tgccatctcg aggaggtctt attcccaaaa caggtgagca acaggcaatg 840
gcacttgtaa ttattggtgg tattttaatt gctttagcct tacgattact atcaaaacat 900
cggaaacatc aaaataagga ttag 924

<210> SEQ ID NO 4
<211> LENGTH: 307
<212> TYPE: PRT
<213> ORGANISM: Streptococcus agalactiae

<400> SEQUENCE: 4

Met Lys Gln Thr Leu Lys Leu Met Phe Ser Phe Leu Leu Met Leu Gly
1 5 10 15

Thr Met Phe Gly Ile Ser Gln Thr Val Leu Ala Gln Glu Thr His Gln
20 25 30

Leu Thr Ile Val His Leu Glu Ala Arg Asp Ile Asp Arg Pro Asn Pro
35 40 45

Gln Leu Glu Ile Ala Pro Lys Glu Gly Thr Pro Ile Glu Gly Val Leu
50 55 60

Tyr Gln Leu Tyr Gln Leu Lys Ser Thr Glu Asp Gly Asp Leu Leu Ala
65 70 75 80

His Trp Asn Ser Leu Thr Ile Thr Glu Leu Lys Lys Gln Ala Gln Gln
85 90 95

```
Val Phe Glu Ala Thr Thr Asn Gln Gln Gly Lys Ala Thr Phe Asn Gln
            100                 105                 110

Leu Pro Asp Gly Ile Tyr Tyr Gly Leu Ala Val Lys Ala Gly Glu Lys
        115                 120                 125

Asn Arg Asn Val Ser Ala Phe Leu Val Asp Leu Ser Glu Asp Lys Val
    130                 135                 140

Ile Tyr Pro Lys Ile Ile Trp Ser Thr Gly Glu Leu Asp Leu Leu Lys
145                 150                 155                 160

Val Gly Val Asp Gly Asp Thr Lys Lys Pro Leu Ala Gly Val Val Phe
                165                 170                 175

Glu Leu Tyr Glu Lys Asn Gly Arg Thr Pro Ile Arg Val Lys Asn Gly
            180                 185                 190

Val His Ser Gln Asp Ile Asp Ala Ala Lys His Leu Glu Thr Asp Ser
        195                 200                 205

Ser Gly His Ile Arg Ile Ser Gly Leu Ile His Gly Asp Tyr Val Leu
    210                 215                 220

Lys Glu Ile Glu Thr Gln Ser Gly Tyr Gln Ile Gly Gln Ala Glu Thr
225                 230                 235                 240

Ala Val Thr Ile Glu Lys Ser Lys Thr Val Thr Val Thr Ile Glu Asn
                245                 250                 255

Lys Lys Val Pro Thr Pro Lys Val Pro Ser Arg Gly Gly Leu Ile Pro
            260                 265                 270

Lys Thr Gly Glu Gln Gln Ala Met Ala Leu Val Ile Ile Gly Gly Ile
        275                 280                 285

Leu Ile Ala Leu Ala Leu Arg Leu Leu Ser Lys His Arg Lys His Gln
    290                 295                 300

Asn Lys Asp
305
```

<210> SEQ ID NO 5
<211> LENGTH: 918
<212> TYPE: DNA
<213> ORGANISM: Streptococcus agalactiae

<400> SEQUENCE: 5

```
atgggacaaa aatcaaaaat atctctagct acgaatattc gtatatggat ttttcgttta     60

attttcttag cgggtttcct tgttttggca tttcccatcg ttagtcaggt catgtacttt    120

caagcctctc acgccaatat taatgctttt aaagaagctg ttaccaagat tgaccgggtg    180

gagattaatc ggcgtttaga acttgcttat gcttataacg ccagtatagc aggtgccaaa    240

actaatggcg aatatccagc gcttaaagac ccctactctg ctgaacaaaa gcaggcaggg    300

gtcgttgagt acgcccgcat gcttgaagtc aaagaacaaa taggtcatgt gattattcca    360

agaattaatc aggatatccc tatttacgct ggctctgctg aagaaaatct tcagaggggc    420

gttggacatt tagaggggac cagtcttcca gtcggtggtg agtcaactca tgccgttcta    480

actgcccatc gagggctacc aacggccaag ctatttacca atttagacaa ggtaacagta    540

ggtgaccgtt tttacattga acacatcggc ggaaagattg cttatcaggt agaccaaatc    600

aaagttatcg cccctgatca gttagaggat ttgtacgtga ttcaaggaga agatcacgtc    660

accctattaa cttgcacacc ttatatgata aatagtcatc gcctcctcgt tcgaggcaag    720

cgaattcctt atgtggaaaa aacagtgcag aaagattcaa agaccttcag gcaacaacaa    780

tacctaacct atgctatgtg ggtagtcgtt ggacttatct tgctgtcgct tctcatttgg    840

tttaaaaaga cgaaacagaa aaagcggaga aagaatgaaa aagcggctag tcaaaatagt    900
```

-continued

```
cacaataatt cgaaataa                                               918


<210> SEQ ID NO 6
<211> LENGTH: 305
<212> TYPE: PRT
<213> ORGANISM: Streptococcus agalactiae

<400> SEQUENCE: 6

Met Gly Gln Lys Ser Lys Ile Ser Leu Ala Thr Asn Ile Arg Ile Trp
1               5                   10                  15

Ile Phe Arg Leu Ile Phe Leu Ala Gly Phe Leu Val Leu Ala Phe Pro
            20                  25                  30

Ile Val Ser Gln Val Met Tyr Phe Gln Ala Ser His Ala Asn Ile Asn
        35                  40                  45

Ala Phe Lys Glu Ala Val Thr Lys Ile Asp Arg Val Glu Ile Asn Arg
    50                  55                  60

Arg Leu Glu Leu Ala Tyr Ala Tyr Asn Ala Ser Ile Ala Gly Ala Lys
65                  70                  75                  80

Thr Asn Gly Glu Tyr Pro Ala Leu Lys Asp Pro Tyr Ser Ala Glu Gln
                85                  90                  95

Lys Gln Ala Gly Val Val Glu Tyr Ala Arg Met Leu Glu Val Lys Glu
            100                 105                 110

Gln Ile Gly His Val Ile Ile Pro Arg Ile Asn Gln Asp Ile Pro Ile
        115                 120                 125

Tyr Ala Gly Ser Ala Glu Glu Asn Leu Gln Arg Gly Val Gly His Leu
    130                 135                 140

Glu Gly Thr Ser Leu Pro Val Gly Gly Glu Ser Thr His Ala Val Leu
145                 150                 155                 160

Thr Ala His Arg Gly Leu Pro Thr Ala Lys Leu Phe Thr Asn Leu Asp
                165                 170                 175

Lys Val Thr Val Gly Asp Arg Phe Tyr Ile Glu His Ile Gly Gly Lys
            180                 185                 190

Ile Ala Tyr Gln Val Asp Gln Ile Lys Val Ile Ala Pro Asp Gln Leu
        195                 200                 205

Glu Asp Leu Tyr Val Ile Gln Gly Glu Asp His Val Thr Leu Leu Thr
    210                 215                 220

Cys Thr Pro Tyr Met Ile Asn Ser His Arg Leu Leu Val Arg Gly Lys
225                 230                 235                 240

Arg Ile Pro Tyr Val Glu Lys Thr Val Gln Lys Asp Ser Lys Thr Phe
                245                 250                 255

Arg Gln Gln Gln Tyr Leu Thr Tyr Ala Met Trp Val Val Val Gly Leu
            260                 265                 270

Ile Leu Leu Ser Leu Leu Ile Trp Phe Lys Lys Thr Lys Gln Lys Lys
        275                 280                 285

Arg Arg Lys Asn Glu Lys Ala Ala Ser Gln Asn Ser His Asn Asn Ser
    290                 295                 300

Lys
305


<210> SEQ ID NO 7
<211> LENGTH: 852
<212> TYPE: DNA
<213> ORGANISM: Streptococcus agalactiae

<400> SEQUENCE: 7

atgaaaaagc ggctagtcaa aatagtcaca ataattcgaa ataataaaat cagaaccctc      60
```

-continued

```
atttttgtga tgggaagtct gattctctta tttccgattg tgagccaggt aagttactac    120

cttgcttcgc atcaaaatat taatcaattt aagcgggaag tcgctaagat tgatactaat    180

acggttgaac gacgcatcgc tttagctaat gcttacaatg agacgttatc aaggaatccc    240

ttgcttatag acccttttac cagtaagcaa aaagaaggtt tgagagagta tgctcgtatg    300

cttgaagttc atgagcaaat aggtcatgtg gcaatcccaa gtatttgggt tgatattcca    360

atttatgctg gaacatccga aactgtgctt cagaaaggta gtgggcattt ggagggaacc    420

agtcttccag tgggaggttt gtcaacccat tcagtactaa ctgcccaccg tggcttgcca    480

acagctaggc tatttaccga cttaaataaa gttaaaaaag gccagatttt ctatgtgacg    540

aacatcaagg aaacacttgc ctacaaagtc gtgtctatca aagttgtgga tccaacagct    600

ttaagtgagg ttaagattgt caatggtaag gattatataa ccttgctgac ttgcacacct    660

tacatgatca atagtcatcg tctcttggta aaaggagagc gtattcctta tgattctacc    720

gaggcggaaa agcacaaaga acaaaccgta caagattatc gtttgtcact agtgttgaag    780

atactactag tattattaat tggactcttc atcgtgataa tgatgagaag atggatgcaa    840

catcgtcaat aa                                                         852


<210> SEQ ID NO 8
<211> LENGTH: 283
<212> TYPE: PRT
<213> ORGANISM: Streptococcus agalactiae

<400> SEQUENCE: 8

Met Lys Lys Arg Leu Val Lys Ile Val Thr Ile Ile Arg Asn Asn Lys
1               5                   10                  15

Ile Arg Thr Leu Ile Phe Val Met Gly Ser Leu Ile Leu Leu Phe Pro
            20                  25                  30

Ile Val Ser Gln Val Ser Tyr Tyr Leu Ala Ser His Gln Asn Ile Asn
        35                  40                  45

Gln Phe Lys Arg Glu Val Ala Lys Ile Asp Thr Asn Thr Val Glu Arg
    50                  55                  60

Arg Ile Ala Leu Ala Asn Ala Tyr Asn Glu Thr Leu Ser Arg Asn Pro
65                  70                  75                  80

Leu Leu Ile Asp Pro Phe Thr Ser Lys Gln Lys Glu Gly Leu Arg Glu
                85                  90                  95

Tyr Ala Arg Met Leu Glu Val His Glu Gln Ile Gly His Val Ala Ile
            100                 105                 110

Pro Ser Ile Gly Val Asp Ile Pro Ile Tyr Ala Gly Thr Ser Glu Thr
        115                 120                 125

Val Leu Gln Lys Gly Ser Gly His Leu Glu Gly Thr Ser Leu Pro Val
    130                 135                 140

Gly Gly Leu Ser Thr His Ser Val Leu Thr Ala His Arg Gly Leu Pro
145                 150                 155                 160

Thr Ala Arg Leu Phe Thr Asp Leu Asn Lys Val Lys Lys Gly Gln Ile
                165                 170                 175

Phe Tyr Val Thr Asn Ile Lys Glu Thr Leu Ala Tyr Lys Val Val Ser
            180                 185                 190

Ile Lys Val Val Asp Pro Thr Ala Leu Ser Glu Val Lys Ile Val Asn
        195                 200                 205

Gly Lys Asp Tyr Ile Thr Leu Leu Thr Cys Thr Pro Tyr Met Ile Asn
    210                 215                 220

Ser His Arg Leu Leu Val Lys Gly Glu Arg Ile Pro Tyr Asp Ser Thr
225                 230                 235                 240
```

Glu Ala Glu Lys His Lys Glu Gln Thr Val Gln Asp Tyr Arg Leu Ser
245 250 255

Leu Val Leu Lys Ile Leu Leu Val Leu Leu Ile Gly Leu Phe Ile Val
260 265 270

Ile Met Met Arg Arg Trp Met Gln His Arg Gln
275 280

<210> SEQ ID NO 9
<211> LENGTH: 2712
<212> TYPE: DNA
<213> ORGANISM: Streptococcus agalactiae

<400> SEQUENCE: 9
atgatgattg tgaataatgg ttatctagaa gggagaaaaa tgaaaaagag acaaaaaata 60
tggagagggt tatcagttac tttactaatc ctgtcccaaa ttccatttgg tatattggta 120
caaggtgaaa cccaagatac caatcaagca cttggaaaag taattgttaa aaaaacggga 180
gacaatgcta caccattagg caaagcgact tttgtgttaa aaaatgacaa tgataagtca 240
gaaacaagtc acgaaacggt agagggttct ggagaagcaa cctttgaaaa cataaaacct 300
ggagactaca cattaagaga agaaacagca ccaattggtt ataaaaaaac tgataaaacc 360
tggaaagtta aagttgcaga taacggagca acaataatcg agggtatgga tgcagataaa 420
gcagagaaac gaaaagaagt tttgaatgcc caatatccaa aatcagctat ttatgaggat 480
acaaaagaaa attacccatt agttaatgta gagggttcca aagttggtga acaatacaaa 540
gcattgaatc caataaatgg aaaagatggt cgaagagaga ttgctgaagg ttggttatca 600
aaaaaaaata caggggtcaa tgatctcgat aagaataaat ataaaattga attaactgtt 660
gagggtaaaa ccactgttga aacgaaagaa cttaatcaac cactagatgt cgttgtgcta 720
ttagataatt caaatagtat gaataatgaa agagccaata attctcaaag agcattaaaa 780
gctggggaag cagttgaaaa gctgattgat aaaattacat caaataaaga caatagagta 840
gctcttgtga catatgcctc aaccattttt gatggtactg aagcgaccgt atcaaaggga 900
gttgccgatc aaaatggtaa agcgctgaat gatagtgtat catgggatta tcataaaact 960
acttttacag caactacaca taattacagt tatttaaatt taacaaatga tgctaacgaa 1020
gttaatattc taaagtcaag aattccaaag gaagcggagc atataaatgg ggatcgcacg 1080
ctctatcaat ttggtgcgac atttactcaa aaagctctaa tgaaagcaaa tgaaatttta 1140
gagacacaaa gttctaatgc tagaaaaaaa cttatttttc acgtaactga tggtgtccct 1200
acgatgtctt atgccataaa ttttaatcct tatatatcaa catcttacca aaaccagttt 1260
aattcttttt taaataaaat accagataga agtggtattc tccaagagga ttttataatc 1320
aatggtgatg attatcaaat agtaaaagga gatggagaga gttttaaact gttttcggat 1380
agaaaagttc ctgttactgg aggaacgaca caagcagctt atcgagtacc gcaaaatcaa 1440
ctctctgtaa tgagtaatga gggatatgca attaatagtg gatatattta tctctattgg 1500
agagattaca actgggtcta tccatttgat cctaagacaa agaaagtttc tgcaacgaaa 1560
caaatcaaaa ctcatggtga gccaacaaca ttatacttta atggaaatat aagacctaaa 1620
ggttatgaca tttttactgt tgggattggt gtaaacggag atcctggtgc aactcctctt 1680
gaagctgaga aatttatgca atcaatatca agtaaaacag aaaattatac taatgttgat 1740
gatacaaata aaatttatga tgagctaaat aaatacttta aaacaattgt tgaggaaaaa 1800
cattctattg ttgatggaaa tgtgactgat cctatgggag agatgattga attccaatta 1860

-continued

```
aaaaatggtc aaagttttac acatgatgat tacgttttgg ttggaaatga tggcagtcaa   1920

ttaaaaaatg gtgtggctct tggtggacca aacagtgatg ggggaatttt aaaagatgtt   1980

acagtgactt atgataagac atctcaaacc atcaaaatca atcatttgaa cttaggaagt   2040

ggacaaaaag tagttcttac ctatgatgta cgtttaaaag ataactatat aagtaacaaa   2100

ttttacaata caaataatcg tacaacgcta agtccgaaga gtgaaaaaga accaaatact   2160

attcgtgatt tcccaattcc caaaattcgt gatgttcgtg agtttccggt actaaccatc   2220

agtaatcaga agaaaatggg tgaggttgaa tttattaaag ttaataaaga caaacattca   2280

gaatcgcttt tgggagctaa gtttcaactt cagatagaaa aagatttttc tgggtataag   2340

caatttgttc cagagggaag tgatgttaca acaaagaatg atggtaaaat ttattttaaa   2400

gcacttcaag atggtaacta taaattatat gaaatttcaa gtccagatgg ctatatagag   2460

gttaaaacga aacctgttgt gacatttaca attcaaaatg gagaagttac gaacctgaaa   2520

gcagatccaa atgctaataa aaatcaaatc gggtatcttg aaggaaatgg taaacatctt   2580

attaccaaca ctcccaaacg cccaccaggt gtttttccta aaacaggggg aattggtaca   2640

attgtctata tattagttgg ttctactttt atgatactta ccatttgttc tttccgtcgt   2700

aaacaattgt aa                                                       2712
```

<210> SEQ ID NO 10
<211> LENGTH: 903
<212> TYPE: PRT
<213> ORGANISM: Streptococcus agalactiae

<400> SEQUENCE: 10

```
Met Met Ile Val Asn Asn Gly Tyr Leu Glu Gly Arg Lys Met Lys Lys
1               5                   10                  15

Arg Gln Lys Ile Trp Arg Gly Leu Ser Val Thr Leu Leu Ile Leu Ser
            20                  25                  30

Gln Ile Pro Phe Gly Ile Leu Val Gln Gly Glu Thr Gln Asp Thr Asn
        35                  40                  45

Gln Ala Leu Gly Lys Val Ile Val Lys Lys Thr Gly Asp Asn Ala Thr
    50                  55                  60

Pro Leu Gly Lys Ala Thr Phe Val Leu Lys Asn Asp Asn Asp Lys Ser
65                  70                  75                  80

Glu Thr Ser His Glu Thr Val Glu Gly Ser Gly Glu Ala Thr Phe Glu
                85                  90                  95

Asn Ile Lys Pro Gly Asp Tyr Thr Leu Arg Glu Glu Thr Ala Pro Ile
            100                 105                 110

Gly Tyr Lys Lys Thr Asp Lys Thr Trp Lys Val Lys Val Ala Asp Asn
        115                 120                 125

Gly Ala Thr Ile Ile Glu Gly Met Asp Ala Asp Lys Ala Glu Lys Arg
    130                 135                 140

Lys Glu Val Leu Asn Ala Gln Tyr Pro Lys Ser Ala Ile Tyr Glu Asp
145                 150                 155                 160

Thr Lys Glu Asn Tyr Pro Leu Val Asn Val Glu Gly Ser Lys Val Gly
                165                 170                 175

Glu Gln Tyr Lys Ala Leu Asn Pro Ile Asn Gly Lys Asp Gly Arg Arg
            180                 185                 190

Glu Ile Ala Glu Gly Trp Leu Ser Lys Lys Asn Thr Gly Val Asn Asp
        195                 200                 205

Leu Asp Lys Asn Lys Tyr Lys Ile Glu Leu Thr Val Glu Gly Lys Thr
    210                 215                 220
```

-continued

```
Thr Val Glu Thr Lys Glu Leu Asn Gln Pro Leu Asp Val Val Val Leu
225                 230                 235                 240

Leu Asp Asn Ser Asn Ser Met Asn Asn Glu Arg Ala Asn Asn Ser Gln
                245                 250                 255

Arg Ala Leu Lys Ala Gly Glu Ala Val Glu Lys Leu Ile Asp Lys Ile
            260                 265                 270

Thr Ser Asn Lys Asp Asn Arg Val Ala Leu Val Thr Tyr Ala Ser Thr
        275                 280                 285

Ile Phe Asp Gly Thr Glu Ala Thr Val Ser Lys Gly Val Ala Asp Gln
    290                 295                 300

Asn Gly Lys Ala Leu Asn Asp Ser Val Ser Trp Asp Tyr His Lys Thr
305                 310                 315                 320

Thr Phe Thr Ala Thr Thr His Asn Tyr Ser Tyr Leu Asn Leu Thr Asn
                325                 330                 335

Asp Ala Asn Glu Val Asn Ile Leu Lys Ser Arg Ile Pro Lys Glu Ala
            340                 345                 350

Glu His Ile Asn Gly Asp Arg Thr Leu Tyr Gln Phe Gly Ala Thr Phe
        355                 360                 365

Thr Gln Lys Ala Leu Met Lys Ala Asn Glu Ile Leu Glu Thr Gln Ser
    370                 375                 380

Ser Asn Ala Arg Lys Lys Leu Ile Phe His Val Thr Asp Gly Val Pro
385                 390                 395                 400

Thr Met Ser Tyr Ala Ile Asn Phe Asn Pro Tyr Ile Ser Thr Ser Tyr
                405                 410                 415

Gln Asn Gln Phe Asn Ser Phe Leu Asn Lys Ile Pro Asp Arg Ser Gly
            420                 425                 430

Ile Leu Gln Glu Asp Phe Ile Ile Asn Gly Asp Asp Tyr Gln Ile Val
        435                 440                 445

Lys Gly Asp Gly Glu Ser Phe Lys Leu Phe Ser Asp Arg Lys Val Pro
    450                 455                 460

Val Thr Gly Gly Thr Thr Gln Ala Ala Tyr Arg Val Pro Gln Asn Gln
465                 470                 475                 480

Leu Ser Val Met Ser Asn Glu Gly Tyr Ala Ile Asn Ser Gly Tyr Ile
                485                 490                 495

Tyr Leu Tyr Trp Arg Asp Tyr Asn Trp Val Tyr Pro Phe Asp Pro Lys
            500                 505                 510

Thr Lys Lys Val Ser Ala Thr Lys Gln Ile Lys Thr His Gly Glu Pro
        515                 520                 525

Thr Thr Leu Tyr Phe Asn Gly Asn Ile Arg Pro Lys Gly Tyr Asp Ile
    530                 535                 540

Phe Thr Val Gly Ile Gly Val Asn Gly Asp Pro Gly Ala Thr Pro Leu
545                 550                 555                 560

Glu Ala Glu Lys Phe Met Gln Ser Ile Ser Ser Lys Thr Glu Asn Tyr
                565                 570                 575

Thr Asn Val Asp Asp Thr Asn Lys Ile Tyr Asp Glu Leu Asn Lys Tyr
            580                 585                 590

Phe Lys Thr Ile Val Glu Glu Lys His Ser Ile Val Asp Gly Asn Val
        595                 600                 605

Thr Asp Pro Met Gly Glu Met Ile Glu Phe Gln Leu Lys Asn Gly Gln
    610                 615                 620

Ser Phe Thr His Asp Asp Tyr Val Leu Val Gly Asn Asp Gly Ser Gln
625                 630                 635                 640

Leu Lys Asn Gly Val Ala Leu Gly Gly Pro Asn Ser Asp Gly Gly Ile
                645                 650                 655
```

```
Leu Lys Asp Val Thr Val Thr Tyr Asp Lys Thr Ser Gln Thr Ile Lys
            660                 665                 670

Ile Asn His Leu Asn Leu Gly Ser Gly Gln Lys Val Val Leu Thr Tyr
        675                 680                 685

Asp Val Arg Leu Lys Asp Asn Tyr Ile Ser Asn Lys Phe Tyr Asn Thr
    690                 695                 700

Asn Asn Arg Thr Thr Leu Ser Pro Lys Ser Glu Lys Glu Pro Asn Thr
705                 710                 715                 720

Ile Arg Asp Phe Pro Ile Pro Lys Ile Arg Asp Val Arg Glu Phe Pro
                725                 730                 735

Val Leu Thr Ile Ser Asn Gln Lys Lys Met Gly Glu Val Glu Phe Ile
            740                 745                 750

Lys Val Asn Lys Asp Lys His Ser Glu Ser Leu Leu Gly Ala Lys Phe
        755                 760                 765

Gln Leu Gln Ile Glu Lys Asp Phe Ser Gly Tyr Lys Gln Phe Val Pro
    770                 775                 780

Glu Gly Ser Asp Val Thr Thr Lys Asn Asp Gly Lys Ile Tyr Phe Lys
785                 790                 795                 800

Ala Leu Gln Asp Gly Asn Tyr Lys Leu Tyr Glu Ile Ser Ser Pro Asp
                805                 810                 815

Gly Tyr Ile Glu Val Lys Thr Lys Pro Val Val Thr Phe Thr Ile Gln
            820                 825                 830

Asn Gly Glu Val Thr Asn Leu Lys Ala Asp Pro Asn Ala Asn Lys Asn
        835                 840                 845

Gln Ile Gly Tyr Leu Glu Gly Asn Gly Lys His Leu Ile Thr Asn Thr
    850                 855                 860

Pro Lys Arg Pro Pro Gly Val Phe Pro Lys Thr Gly Gly Ile Gly Thr
865                 870                 875                 880

Ile Val Tyr Ile Leu Val Gly Ser Thr Phe Met Ile Leu Thr Ile Cys
                885                 890                 895

Ser Phe Arg Arg Lys Gln Leu
            900
```

<210> SEQ ID NO 11
<211> LENGTH: 21
<212> TYPE: DNA
<213> ORGANISM: Artificial sequence
<220> FEATURE:
<223> OTHER INFORMATION: oligonucleotide

<400> SEQUENCE: 11
ctaggtggat ccttcggcaa t 21

<210> SEQ ID NO 12
<211> LENGTH: 10
<212> TYPE: DNA
<213> ORGANISM: Artificial sequence
<220> FEATURE:
<223> OTHER INFORMATION: oligonucleotide

<400> SEQUENCE: 12
cgattgccga 10

<210> SEQ ID NO 13
<211> LENGTH: 25
<212> TYPE: DNA
<213> ORGANISM: Artificial sequence
<220> FEATURE:
<223> OTHER INFORMATION: oligonucleotide

<400> SEQUENCE: 13
aggcaactgt gctaaccgag ggaat 25

<210> SEQ ID NO 14
<211> LENGTH: 11
<212> TYPE: DNA
<213> ORGANISM: Artificial sequence
<220> FEATURE:
<223> OTHER INFORMATION: oligonucleotide

<400> SEQUENCE: 14
cgattccctc g 11

<210> SEQ ID NO 15
<211> LENGTH: 1509
<212> TYPE: DNA
<213> ORGANISM: Streptococcus agalactiae

<400> SEQUENCE: 15
atgaaaaaga aaatgattca atcgctgtta gtggcgagtt tagcatttgg tatggctgta 60
tcaccagtta cgccgatagc ttttgccgct gagacaggga caattacagt tcaagatact 120
caaaaaggcg caacctataa agcatataaa gtttttgatg cagaaataga taatgcaaat 180
gtatctgatt cgaataaaga tggagcttct tatttaattc ctcaaggtaa agaagctgag 240
tataaagctt caactgattt taattctctt tttacgacaa ctactaatgg agggagaaca 300
tatgtaacta aaaaagatac tgcgtcagca aatgagattg cgacatgggc taaatctata 360
tcagctaata ctacaccagt ttccactgtt actgagtcaa ataatgatgg tactgaggtt 420
attaatgttt cccaatatgg atattattat gtttctagca ctgttaataa tggagctgta 480
attatggtta catctgtaac tccaaatgct actattcatg aaaagaatac tgatgcgaca 540
tggggagatg gtggtggaaa aactgtagat caaaaaacgt actcggttgg tgatacagtc 600
aaatatacta ttacttataa gaatgcagtc aattatcatg gtacagaaaa agtgtatcaa 660
tatgttataa aggatactat gccatctgct tctgtagttg atttgaacga agggtcttat 720
gaagtaacta ttactgatgg atcagggaat attacaactc taactcaagg ttcggaaaaa 780
gcaactggga agtataacct gttagaggaa aataataatt tcacgattac tattccgtgg 840
gcagctacca atactccaac cggaaatact caaaatggag ctaatgatga ctttttttat 900
aagggaataa atacaatcac agtcacttat acaggagtat taaagagtgg agctaaacca 960
ggttcagctg atttaccaga aaatacaaac attgcgacca tcaaccccaa tactagcaat 1020
gatgacccag gtcaaaaagt aacagtgagg gatggtcaaa ttactataaa aaaaattgat 1080
ggttccacaa aagcttcatt acaaggtgct atatttgttt taaagaatgc tacgggtcaa 1140
tttctaaact ttaacgatac aaataacgtt gaatggggca cagaagctaa tgcaacagaa 1200
tatacaacag gagcagatgg tataattacc attacaggct tgaaagaagg tacatactat 1260
ctagttgaga aaaaggctcc cttaggttac aatttgttag ataactctca gaaggttatt 1320
ttaggagatg gagccactga tacgactaat tcagataacc ttttagttaa cccaactgtt 1380
gaaaataaca aaggtactga gttgccttca acaggtggta ttggtacaac aattttctac 1440
attataggtg caattttagt aataggagca ggtatcgtgc ttgttgctcg tcgtcgttta 1500
cgttcttaa 1509

<210> SEQ ID NO 16
<211> LENGTH: 502

<212> TYPE: PRT
<213> ORGANISM: Streptococcus agalactiae

<400> SEQUENCE: 16

```
Met Lys Lys Lys Met Ile Gln Ser Leu Leu Val Ala Ser Leu Ala Phe
1               5                   10                  15

Gly Met Ala Val Ser Pro Val Thr Pro Ile Ala Phe Ala Ala Glu Thr
            20                  25                  30

Gly Thr Ile Thr Val Gln Asp Thr Gln Lys Gly Ala Thr Tyr Lys Ala
        35                  40                  45

Tyr Lys Val Phe Asp Ala Glu Ile Asp Asn Ala Asn Val Ser Asp Ser
    50                  55                  60

Asn Lys Asp Gly Ala Ser Tyr Leu Ile Pro Gln Gly Lys Glu Ala Glu
65                  70                  75                  80

Tyr Lys Ala Ser Thr Asp Phe Asn Ser Leu Phe Thr Thr Thr Thr Asn
                85                  90                  95

Gly Gly Arg Thr Tyr Val Thr Lys Lys Asp Thr Ala Ser Ala Asn Glu
            100                 105                 110

Ile Ala Thr Trp Ala Lys Ser Ile Ser Ala Asn Thr Thr Pro Val Ser
        115                 120                 125

Thr Val Thr Glu Ser Asn Asn Asp Gly Thr Glu Val Ile Asn Val Ser
    130                 135                 140

Gln Tyr Gly Tyr Tyr Tyr Val Ser Ser Thr Val Asn Asn Gly Ala Val
145                 150                 155                 160

Ile Met Val Thr Ser Val Thr Pro Asn Ala Thr Ile His Glu Lys Asn
                165                 170                 175

Thr Asp Ala Thr Trp Gly Asp Gly Gly Gly Lys Thr Val Asp Gln Lys
            180                 185                 190

Thr Tyr Ser Val Gly Asp Thr Val Lys Tyr Thr Ile Thr Tyr Lys Asn
        195                 200                 205

Ala Val Asn Tyr His Gly Thr Glu Lys Val Tyr Gln Tyr Val Ile Lys
    210                 215                 220

Asp Thr Met Pro Ser Ala Ser Val Val Asp Leu Asn Glu Gly Ser Tyr
225                 230                 235                 240

Glu Val Thr Ile Thr Asp Gly Ser Gly Asn Ile Thr Thr Leu Thr Gln
                245                 250                 255

Gly Ser Glu Lys Ala Thr Gly Lys Tyr Asn Leu Leu Glu Glu Asn Asn
            260                 265                 270

Asn Phe Thr Ile Thr Ile Pro Trp Ala Ala Thr Asn Thr Pro Thr Gly
        275                 280                 285

Asn Thr Gln Asn Gly Ala Asn Asp Asp Phe Phe Tyr Lys Gly Ile Asn
    290                 295                 300

Thr Ile Thr Val Thr Tyr Thr Gly Val Leu Lys Ser Gly Ala Lys Pro
305                 310                 315                 320

Gly Ser Ala Asp Leu Pro Glu Asn Thr Asn Ile Ala Thr Ile Asn Pro
                325                 330                 335

Asn Thr Ser Asn Asp Asp Pro Gly Gln Lys Val Thr Val Arg Asp Gly
            340                 345                 350

Gln Ile Thr Ile Lys Lys Ile Asp Gly Ser Thr Lys Ala Ser Leu Gln
        355                 360                 365

Gly Ala Ile Phe Val Leu Lys Asn Ala Thr Gly Gln Phe Leu Asn Phe
    370                 375                 380

Asn Asp Thr Asn Asn Val Glu Trp Gly Thr Glu Ala Asn Ala Thr Glu
385                 390                 395                 400
```

```
Tyr Thr Thr Gly Ala Asp Gly Ile Ile Thr Ile Thr Gly Leu Lys Glu
                405                 410                 415

Gly Thr Tyr Tyr Leu Val Glu Lys Lys Ala Pro Leu Gly Tyr Asn Leu
            420                 425                 430

Leu Asp Asn Ser Gln Lys Val Ile Leu Gly Asp Gly Ala Thr Asp Thr
        435                 440                 445

Thr Asn Ser Asp Asn Leu Leu Val Asn Pro Thr Val Glu Asn Asn Lys
    450                 455                 460

Gly Thr Glu Leu Pro Ser Thr Gly Gly Ile Gly Thr Thr Ile Phe Tyr
465                 470                 475                 480

Ile Ile Gly Ala Ile Leu Val Ile Gly Ala Gly Ile Val Leu Val Ala
                485                 490                 495

Arg Arg Arg Leu Arg Ser
            500


<210> SEQ ID NO 17
<211> LENGTH: 5
<212> TYPE: PRT
<213> ORGANISM: Artificial sequence
<220> FEATURE:
<223> OTHER INFORMATION: consensus
<220> FEATURE:
<221> NAME/KEY: MISC_FEATURE
<222> LOCATION: (3)..(3)
<223> OTHER INFORMATION: x= any amino acid

<400> SEQUENCE: 17

Leu Pro Xaa Thr Gly
1               5


<210> SEQ ID NO 18
<211> LENGTH: 1683
<212> TYPE: DNA
<213> ORGANISM: Streptococcus agalactiae

<400> SEQUENCE: 18

atggtgatcg tattccggat tatacagata ttacaaggga ttatatccaa gatccttcag      60

gtacatatta ttataagtat gattcacgag ataaagatcc cgactcaact aaagatgcct     120

attatacgac agatactagt ctcatcaaat gttgatacaa caactaagta caagtacgta     180

aaagacgctt acaaattagt cggttggtat tatgttaatc catatggtag tattagacct     240

tataactttt caggtgctgt aactcaagat atcaatttaa gagctatttg gcgaaaggct     300

ggagattatc atattatata cagcaatgat gctgttggta cagatggaaa gccagcattg     360

gatgcttctg gtcagcaatt acaaacaagt aatgagccta ctgaccctga ttcctatgac     420

gatggctccc attcagcctt actgagacgt ccgacaatgc cagatggcta tcgtttccgt     480

ggctggtggt acaatggtaa aatttataac ccatatgatt ccattgatat tgacgcccat     540

ttagcagatg ctaataaaaa tatcaccata aaacctgtca ttattccagt aggagatatc     600

aaattagaag atacctccat caaatacaat ggtaacggtg gtactagagt agaaaatggt     660

aatgtggtaa cacaagtgga gacaccgcgt atggagttga atagcacaac tacaattcct     720

gaaaaccaat actttacaag gacaggttac aaccttattg gttggcatca tgataaggat     780

ttagctgata caggacgtgt ggaatttaca gcaggtcaat caataggtat tgataacaac     840

cttgatgcaa caaatacctt atatgctgtt tggcaaccta aagaatacac cgtcggagta     900

agtaaaactg tcgttggact agatgaagat aagacgaaag acttcttgtt taatccaagt     960

gaaacgttgc aacaagagaa ttttccgctg agagatggtc agactaagga atttaaagta    1020
```

```
ccttatggaa cttctatatc aatagatgaa caagcctacg atgaatttaa agtatctgag   1080

tcaattacag aaaaaaatct agcaactggt gaagctgata aaacttatga tgctaccggc   1140

ttacaatccc tgacagtttc aggagacgta gatattagct ttaccaatac acgtatcaag   1200

caaaaagtac gactacagaa agttaatgtc gaaaatgata ataatttttt agcaggtgca   1260

gtttttgata tttatgaatc agatgctaat gggaataaag cttcacatcc tatgtattca   1320

gggctggtga caaacgataa aggcttgtta ttagtggatg ctaataacta cctcagtttg   1380

ccagtaggaa aatactacct aacagagaca aaggcccctc cagggtacct actacctaaa   1440

aatgatgata tatcagtatt agtgatttct acgggagtta cctttgaaca aaatggtaat   1500

aatgcgacac caataaaaga gaatttagtg gatggaagta cagtatatac ttttaaaatt   1560

actaacagta aaggaacaga attgcctagt actggaggta ttggaacaca catttatatc   1620

ctagttggtt tagctttagc tctaccatca ggattaatat tatactatcg aaaaaaaata   1680

tga                                                                 1683
```

<210> SEQ ID NO 19
<211> LENGTH: 560
<212> TYPE: PRT
<213> ORGANISM: Streptococcus agalactiae

<400> SEQUENCE: 19

```
Met Val Ile Val Phe Arg Ile Ile Gln Ile Leu Gln Gly Ile Ile Ser
1               5                   10                  15

Lys Ile Leu Gln Val His Ile Ile Ile Ser Met Ile His Glu Ile Lys
            20                  25                  30

Ile Pro Thr Gln Leu Lys Met Pro Ile Ile Arg Gln Ile Leu Val Ser
        35                  40                  45

Ser Asn Val Asp Thr Thr Thr Lys Tyr Lys Tyr Val Lys Asp Ala Tyr
    50                  55                  60

Lys Leu Val Gly Trp Tyr Tyr Val Asn Pro Tyr Gly Ser Ile Arg Pro
65                  70                  75                  80

Tyr Asn Phe Ser Gly Ala Val Thr Gln Asp Ile Asn Leu Arg Ala Ile
                85                  90                  95

Trp Arg Lys Ala Gly Asp Tyr His Ile Ile Tyr Ser Asn Asp Ala Val
            100                 105                 110

Gly Thr Asp Gly Lys Pro Ala Leu Asp Ala Ser Gly Gln Gln Leu Gln
        115                 120                 125

Thr Ser Asn Glu Pro Thr Asp Pro Asp Ser Tyr Asp Asp Gly Ser His
    130                 135                 140

Ser Ala Leu Leu Arg Arg Pro Thr Met Pro Asp Gly Tyr Arg Phe Arg
145                 150                 155                 160

Gly Trp Trp Tyr Asn Gly Lys Ile Tyr Asn Pro Tyr Asp Ser Ile Asp
                165                 170                 175

Ile Asp Ala His Leu Ala Asp Ala Asn Lys Asn Ile Thr Ile Lys Pro
            180                 185                 190

Val Ile Ile Pro Val Gly Asp Ile Lys Leu Glu Asp Thr Ser Ile Lys
        195                 200                 205

Tyr Asn Gly Asn Gly Gly Thr Arg Val Glu Asn Gly Asn Val Val Thr
    210                 215                 220

Gln Val Glu Thr Pro Arg Met Glu Leu Asn Ser Thr Thr Thr Ile Pro
225                 230                 235                 240

Glu Asn Gln Tyr Phe Thr Arg Thr Gly Tyr Asn Leu Ile Gly Trp His
                245                 250                 255
```

-continued

His Asp Lys Asp Leu Ala Asp Thr Gly Arg Val Glu Phe Thr Ala Gly
260 265 270

Gln Ser Ile Gly Ile Asp Asn Asn Leu Asp Ala Thr Asn Thr Leu Tyr
275 280 285

Ala Val Trp Gln Pro Lys Glu Tyr Thr Val Gly Val Ser Lys Thr Val
290 295 300

Val Gly Leu Asp Glu Asp Lys Thr Lys Asp Phe Leu Phe Asn Pro Ser
305 310 315 320

Glu Thr Leu Gln Gln Glu Asn Phe Pro Leu Arg Asp Gly Gln Thr Lys
325 330 335

Glu Phe Lys Val Pro Tyr Gly Thr Ser Ile Ser Ile Asp Glu Gln Ala
340 345 350

Tyr Asp Glu Phe Lys Val Ser Glu Ser Ile Thr Glu Lys Asn Leu Ala
355 360 365

Thr Gly Glu Ala Asp Lys Thr Tyr Asp Ala Thr Gly Leu Gln Ser Leu
370 375 380

Thr Val Ser Gly Asp Val Asp Ile Ser Phe Thr Asn Thr Arg Ile Lys
385 390 395 400

Gln Lys Val Arg Leu Gln Lys Val Asn Val Glu Asn Asp Asn Asn Phe
405 410 415

Leu Ala Gly Ala Val Phe Asp Ile Tyr Glu Ser Asp Ala Asn Gly Asn
420 425 430

Lys Ala Ser His Pro Met Tyr Ser Gly Leu Val Thr Asn Asp Lys Gly
435 440 445

Leu Leu Leu Val Asp Ala Asn Asn Tyr Leu Ser Leu Pro Val Gly Lys
450 455 460

Tyr Tyr Leu Thr Glu Thr Lys Ala Pro Pro Gly Tyr Leu Leu Pro Lys
465 470 475 480

Asn Asp Asp Ile Ser Val Leu Val Ile Ser Thr Gly Val Thr Phe Glu
485 490 495

Gln Asn Gly Asn Asn Ala Thr Pro Ile Lys Glu Asn Leu Val Asp Gly
500 505 510

Ser Thr Val Tyr Thr Phe Lys Ile Thr Asn Ser Lys Gly Thr Glu Leu
515 520 525

Pro Ser Thr Gly Gly Ile Gly Thr His Ile Tyr Ile Leu Val Gly Leu
530 535 540

Ala Leu Ala Leu Pro Ser Gly Leu Ile Leu Tyr Tyr Arg Lys Lys Ile
545 550 555 560

<210> SEQ ID NO 20
<211> LENGTH: 6
<212> TYPE: PRT
<213> ORGANISM: Artificial sequence
<220> FEATURE:
<223> OTHER INFORMATION: consensus

<400> SEQUENCE: 20

Leu Pro Ser Thr Gly Gly
1 5

<210> SEQ ID NO 21
<211> LENGTH: 6
<212> TYPE: PRT
<213> ORGANISM: Artificial sequence
<220> FEATURE:
<223> OTHER INFORMATION: consensus
<220> FEATURE:
<221> NAME/KEY: MISC_FEATURE
<222> LOCATION: (1)..(1)

<223> OTHER INFORMATION: x=any amino acid
<220> FEATURE:
<221> NAME/KEY: MISC_FEATURE
<222> LOCATION: (3)..(3)
<223> OTHER INFORMATION: x=any amino acid

<400> SEQUENCE: 21

Xaa Pro Xaa Thr Gly Gly
1 5

<210> SEQ ID NO 22
<211> LENGTH: 2714
<212> TYPE: DNA
<213> ORGANISM: Streptococcus pneumoniae

<400> SEQUENCE: 22
caatcagaaa ttaccacgtg gcaatgttga ctttatgaag gtggatggtc ggaccaatac 60
ctctcttcaa ggggcaatgt tcaaagtcat gaaagaagaa agcggacact atactcctgt 120
tcttcaaaat ggtaaggaag tagttgtaac atcagggaaa gatggtcgtt tccgagtgga 180
aggtctagag tatgggacat actatttatg ggagctccaa gctccaactg gttatgttca 240
attaacatcg cctgtttcct ttacaatcgg gaaagatact cgtaaggaac tggtaacagt 300
ggttaaaaat aacaagcgac cacggattga tgtgccagat acaggggaag aaaccttgta 360
tatcttgatg cttgttgcca ttttgttgtt tggtagtggt tattatctta cgaaaaaacc 420
aaataactga tattcaatgt acatcattat gaaaaagata gcaggctgaa gggaagacca 480
gagtactctg aggtgatgtt aatcaggaat catggtgatg tggcatgaat cacaataacg 540
gatatgaggc tgggcagatt gtgccagcct cattgtgggt tattgtttgt aaaacgatag 600
gactggtctg gtaatcattt taggaatgga caggactggg attctgattt aaaatggatg 660
gtgaatcaga aagaaatgag attttctcgt ttctcttagc agataggatt gtctgttagg 720
aaaagcgata aaatgatgag tttgaagata aagggatgct gataaaaatg gtaaaaacaa 780
aaaagcaaaa acgaaataat ctcctattag gagtggtatt tttcattgga atggcggtaa 840
tggcgtatcc gctggtgtct cgcttgtatt atcgagtgga atcaaatcaa caaattgctg 900
actttgataa ggaaaaagca acgttggatg aggctgacat tgatgaacga atgaaattgg 960
cacaagcctt caatgactct ttgaataatg tagtgagtgg cgatccttgg tcggaagaaa 1020
tgaagaaaaa agggcgagca gagtatgcac gtatgttaga aatccatgag cggatggggc 1080
atgtggaaat ccccgttatt gacgtggatt tgccggttta tgctggtact gctgaagagg 1140
tattgcagca aggggctggg catctagagg gaacttctct gccgatcgga ggcaattcga 1200
cccatgcggt gattacggca catacaggtt tgccaacagc taagatgttt acggatttga 1260
ccaaacttaa agttggggat aagttttatg tgcacaatat caaggaagtg atggcctatc 1320
aagtggatca agtaaaggtg attgagccga cgaactttga tgatttattg attgtaccag 1380
gtcatgatta tgtgaccttg ctgacttgta cgccatacat gatcaatacc catcgtctat 1440
tggttcgggg gcatcggata ccgtacgtag cagaggttga ggaagaattt attgcagcaa 1500
acaaactcag tcatctctat cgctacctgt tttatgtggc agttggtttg attgtgattc 1560
ttttatggat tattcgacgc ttgcgcaaga agaaaaaaca accggaaaag gctttgaagg 1620
cgctgaaagc agcaaggaag gaagtgaagg tggaggatgg acaacagtag acgttcacga 1680
aaaaaaggca caaaaaagaa gaaacatccg ctgatccttc ttctgatttt cttagtagga 1740
ttcgccgttg cgatatatcc attggtgtct cgttattatt atcgtattga gtcaaacgag 1800
gttattaaag agtttgatga gacggtttcc cagatggata aggcagaact tgaggagcgt 1860

```
tggcgcttgg ctcaagcctt caatgcgacc ttgaaaccat ctgaaattct tgatcctttt   1920

acagagcaag agaaaaagaa aggcgtctca gaatatgcca atatgctaaa ggtccatgag   1980

cggattggct atgtggaaat tcctgcgatt gatcaggaaa ttccgatgta tgtcggaacg   2040

agtgaggaca ttcttcagaa aggggcaggg ctgttagaag ggcttcgct  gcctgttgga   2100

ggtgaaaata cccatacagt gatcactgct cacagaggat tgccaacggc agaattgttc   2160

agtcaattgg ataagatgaa aaaaggggat atcttttatc ttcacgtttt agatcaggtg   2220

ttggcctacc aagtggatca gatagtgacg gtggagccga atgactttga gcctgtcttg   2280

attcaacatg ggaagatta  tgcgaccttg ttgacttgta caccgtatat gattaacagt   2340

catcgtctgt tggtacgtgg gaagcggatt ccgtatacgg caccaattgc agagcggaat   2400

cgagcggtga gagagcgtgg gcaattctgg ttgtggttat tactaggagc gatggcggtc   2460

atccttctct tgctgtatcg cgtgtatcgt aatcgacgga ttgtcaaagg actagaaaag   2520

caattggagg ggcgtcatgt caaggactaa actacgagcc ttattgggat acttgttgat   2580

gttggtagcc tgtttgattc ctatttattg ttttggacag atggtgttgc agtctcttgg   2640

acaggtgaaa ggtcatgcta catttgtgaa atccatgaca actgaaatgt accaagaaca   2700

acagaaccat tctc                                                     2714
```

```
<210> SEQ ID NO 23
<211> LENGTH: 297
<212> TYPE: PRT
<213> ORGANISM: Streptococcus pneumoniae

<400> SEQUENCE: 23

Met Asp Asn Ser Arg Arg Ser Arg Lys Lys Gly Thr Lys Lys Lys Lys
1               5                   10                  15

His Pro Leu Ile Leu Leu Leu Ile Phe Leu Val Gly Phe Ala Val Ala
            20                  25                  30

Ile Tyr Pro Leu Val Ser Arg Tyr Tyr Tyr Arg Ile Glu Ser Asn Glu
        35                  40                  45

Val Ile Lys Glu Phe Asp Glu Thr Val Ser Gln Met Asp Lys Ala Glu
    50                  55                  60

Leu Glu Glu Arg Trp Arg Leu Ala Gln Ala Phe Asn Ala Thr Leu Lys
65                  70                  75                  80

Pro Ser Glu Ile Leu Asp Pro Phe Thr Glu Gln Glu Lys Lys Lys Gly
                85                  90                  95

Val Ser Glu Tyr Ala Asn Met Leu Lys Val His Glu Arg Ile Gly Tyr
            100                 105                 110

Val Glu Ile Pro Ala Ile Asp Gln Glu Ile Pro Met Tyr Val Gly Thr
        115                 120                 125

Ser Glu Asp Ile Leu Gln Lys Gly Ala Gly Leu Leu Glu Gly Ala Ser
    130                 135                 140

Leu Pro Val Gly Gly Glu Asn Thr His Thr Val Ile Thr Ala His Arg
145                 150                 155                 160

Gly Leu Pro Thr Ala Glu Leu Phe Ser Gln Leu Asp Lys Met Lys Lys
                165                 170                 175

Gly Asp Ile Phe Tyr Leu His Val Leu Asp Gln Val Leu Ala Tyr Gln
            180                 185                 190

Val Asp Gln Ile Val Thr Val Glu Pro Asn Asp Phe Glu Pro Val Leu
        195                 200                 205

Ile Gln His Gly Glu Asp Tyr Ala Thr Leu Leu Thr Cys Thr Pro Tyr
    210                 215                 220
```

-continued

Met Ile Asn Ser His Arg Leu Leu Val Arg Gly Lys Arg Ile Pro Tyr
225 230 235 240

Thr Ala Pro Ile Ala Glu Arg Asn Arg Ala Val Arg Glu Arg Gly Gln
245 250 255

Phe Trp Leu Trp Leu Leu Leu Gly Ala Met Ala Val Ile Leu Leu Leu
260 265 270

Leu Tyr Arg Val Tyr Arg Asn Arg Arg Ile Val Lys Gly Leu Glu Lys
275 280 285

Gln Leu Glu Gly Arg His Val Lys Asp
290 295

<210> SEQ ID NO 24
<211> LENGTH: 894
<212> TYPE: DNA
<213> ORGANISM: Streptococcus pneumoniae

<400> SEQUENCE: 24
atggacaaca gtagacgttc acgaaaaaaa ggcacaaaaa agaagaaaca tccgctgatc 60
cttcttctga ttttcttagt aggattcgcc gttgcgatat atccattggt gtctcgttat 120
tattatcgta ttgagtcaaa cgaggttatt aaagagtttg atgagacggt ttcccagatg 180
gataaggcag aacttgagga gcgttggcgc ttggctcaag ccttcaatgc gaccttgaaa 240
ccatctgaaa ttcttgatcc ttttacagag caagagaaaa agaaaggcgt ctcagaatat 300
gccaatatgc taaaggtcca tgagcggatt ggctatgtgg aaattcctgc gattgatcag 360
gaaattccga tgtatgtcgg aacgagtgag gacattcttc agaaaggggc agggctgtta 420
gaaggggctt cgctgcctgt tggaggtgaa aatacccata cagtgatcac tgctcacaga 480
ggattgccaa cggcagaatt gttcagtcaa ttggataaga tgaaaaaagg ggatatcttt 540
tatcttcacg ttttagatca ggtgttggcc taccaagtgg atcagatagt gacggtggag 600
ccgaatgact ttgagcctgt cttgattcaa catggggaag attatgcgac cttgttgact 660
tgtacaccgt atatgattaa cagtcatcgt ctgttggtac gtgggaagcg gattccgtat 720
acggcaccaa ttgcagagcg gaatcgagcg gtgagagagc gtgggcaatt ctggttgtgg 780
ttattactag gagcgatggc ggtcatcctt ctcttgctgt atcgcgtgta tcgtaatcga 840
cggattgtca aggactaga aaagcaattg gaggggcgtc atgtcaagga ctaa 894

<210> SEQ ID NO 25
<211> LENGTH: 3010
<212> TYPE: DNA
<213> ORGANISM: Streptococcus pneumoniae

<400> SEQUENCE: 25
tgttaggaaa agcgataaaa tgatgagttt gaagataaag ggatgctgat aaaaatggta 60
aaaacaaaaa agcaaaaacg aaataatctc ctattaggag tggtattttt cattggaatg 120
gcggtaatgg cgtatccgct ggtgtctcgc ttgtattatc gagtggaatc aaatcaacaa 180
attgctgact ttgataagga aaaagcaacg ttggatgagg ctgacattga tgaacgaatg 240
aaattggcac aagccttcaa tgactctttg aataatgtag tgagtggcga tccttggtcg 300
gaagaaatga agaaaaaagg gcgagcagag tatgcacgta tgttagaaat ccatgagcgg 360
atggggcatg tggaaatccc cgttattgac gtggatttgc cggtttatgc tggtactgct 420
gaagaggtat tgcagcaagg ggctgggcat ctagagggaa cttctctgcc gatcggaggc 480
aattcgaccc atgcggtgat tacggcacat acaggtttgc caacagctaa gatgtttacg 540

-continued

```
gatttgacca aacttaaagt tggggataag ttttatgtgc acaatatcaa ggaagtgatg    600
gcctatcaag tggatcaagt aaaggtgatt gagccgacga actttgatga tttattgatt    660
gtaccaggtc atgattatgt gaccttgctg acttgtacgc catacatgat caatacccat    720
cgtctattgg ttcgggggca tcggataccg tacgtagcag aggttgagga agaatttatt    780
gcagcaaaca aactcagtca tctctatcgc tacctgtttt atgtggcagt tggtttgatt    840
gtgattcttt tatggattat tcgacgcttg cgcaagaaga aaaaacaacc ggaaaaggct    900
ttgaaggcgc tgaaagcagc aaggaaggaa gtgaaggtgg aggatggaca acagtagacg    960
ttcacgaaaa aaaggcacaa aaaagaagaa acatccgctg atccttcttc tgattttctt   1020
agtaggattc gccgttgcga tatatccatt ggtgtctcgt tattattatc gtattgagtc   1080
aaacgaggtt attaaagagt ttgatgagac ggtttcccag atggataagg cagaacttga   1140
ggagcgttgg cgcttggctc aagccttcaa tgcgaccttg aaaccatctg aaattcttga   1200
tcctttttaca gagcaagaga aaaagaaagg cgtctcagaa tatgccaata tgctaaaggt   1260
ccatgagcgg attggctatg tggaaattcc tgcgattgat caggaaattc cgatgtatgt   1320
cggaacgagt gaggacattc ttcagaaagg ggcagggctg ttagaagggg cttcgctgcc   1380
tgttggaggt gaaaataccc atacagtgat cactgctcac agaggattgc caacggcaga   1440
attgttcagt caattggata agatgaaaaa aggggatatc ttttatcttc acgttttaga   1500
tcaggtgttg gcctaccaag tggatcagat agtgacggtg gagccgaatg actttgagcc   1560
tgtcttgatt caacatgggg aagattatgc gaccttgttg acttgtacac cgtatatgat   1620
taacagtcat cgtctgttgg tacgtgggaa gcggattccg tatacggcac caattgcaga   1680
gcggaatcga gcggtgagag agcgtgggca attctggttg tggttattac taggagcgat   1740
ggcggtcatc cttctcttgc tgtatcgcgt gtatcgtaat cgacggattg tcaaaggact   1800
agaaaagcaa ttggaggggc gtcatgtcaa ggactaaact acgagcctta ttgggatact   1860
tgttgatgtt ggtagcctgt ttgattccta tttattgttt tggacagatg gtgttgcagt   1920
ctcttggaca ggtgaaaggt catgctacat ttgtgaaatc catgacaact gaaatgtacc   1980
aagaacaaca gaaccattct ctcgcctaca atcaacgctt ggcttcgcaa aatcgcattg   2040
tagatccttt tttggcggag ggatatgagg tcaattacca agtgtctgac gaccctgatg   2100
cagtctatgg ttacttgtct attccaagtt tggaaatcat ggagccggtt tatttgggag   2160
cagattatca tcatttaggg atgggcttgg ctcatgtgga tggtacaccg ctgcctctgg   2220
atggtacagg gattcgctca gtgattgctg ggcaccgtgc agagccaagc catgtctttt   2280
tccgccattt ggatcagcta aaagttggag atgctcttta ttatgataat ggccaggaaa   2340
ttgtagaata tcagatgatg gacacagaga ttattttacc gtcggaatgg gaaaaattag   2400
aatcggttag ctctaaaaat atcatgacct tgataacctg cgatccgatt cctaccttta   2460
ataaacgctt attagtgaat tttgaacgag tcgctgttta tcaaaaatca gatccacaaa   2520
cagctgcagt tgcgagggtt gcttttacga aagaaggaca atctgtatcg cgtgttgcaa   2580
cctctcaatg gttgtaccgt gggctagtgg tactggcatt tctgggaatc ctgtttgttt   2640
tgtggaagct agcacgttta ctacgaggga aataaaaaga aatgaaagga aagctaaggc   2700
tgttcctttt tccggctctt tgtcaactgt agtgggttga aaaaaagcta agctcgagaa   2760
aggacaaatt ttgtcctttc ttttttgata ttcagagcga taaaaatccg ttttttgaag   2820
ttttcaaagt ttcgaaaacc aaaggcattg cgcttgataa gtttgatgag attattggtc   2880
gcttccagtt tggcattaga atagtgtagt tgaagggcgt tgataacctt ttctttatct   2940
```

ttgaggaagg ttttaaagac agtctgaaaa ataggatgaa cctgcttaag attgtcctcg 3000
ataagttcga 3010

<210> SEQ ID NO 26
<211> LENGTH: 304
<212> TYPE: PRT
<213> ORGANISM: Streptococcus pneumoniae

<400> SEQUENCE: 26

Met Leu Ile Lys Met Val Lys Thr Lys Lys Gln Lys Arg Asn Asn Leu
1 5 10 15

Leu Leu Gly Val Val Phe Phe Ile Gly Met Ala Val Met Ala Tyr Pro
20 25 30

Leu Val Ser Arg Leu Tyr Tyr Arg Val Glu Ser Asn Gln Gln Ile Ala
35 40 45

Asp Phe Asp Lys Glu Lys Ala Thr Leu Asp Glu Ala Asp Ile Asp Glu
50 55 60

Arg Met Lys Leu Ala Gln Ala Phe Asn Asp Ser Leu Asn Asn Val Val
65 70 75 80

Ser Gly Asp Pro Trp Ser Glu Glu Met Lys Lys Lys Gly Arg Ala Glu
85 90 95

Tyr Ala Arg Met Leu Glu Ile His Glu Arg Met Gly His Val Glu Ile
100 105 110

Pro Val Ile Asp Val Asp Leu Pro Val Tyr Ala Gly Thr Ala Glu Glu
115 120 125

Val Leu Gln Gln Gly Ala Gly His Leu Glu Gly Thr Ser Leu Pro Ile
130 135 140

Gly Gly Asn Ser Thr His Ala Val Ile Thr Ala His Thr Gly Leu Pro
145 150 155 160

Thr Ala Lys Met Phe Thr Asp Leu Thr Lys Leu Lys Val Gly Asp Lys
165 170 175

Phe Tyr Val His Asn Ile Lys Glu Val Met Ala Tyr Gln Val Asp Gln
180 185 190

Val Lys Val Ile Glu Pro Thr Asn Phe Asp Asp Leu Leu Ile Val Pro
195 200 205

Gly His Asp Tyr Val Thr Leu Leu Thr Cys Thr Pro Tyr Met Ile Asn
210 215 220

Thr His Arg Leu Leu Val Arg Glu His Arg Ile Pro Tyr Val Ala Glu
225 230 235 240

Val Glu Glu Glu Phe Ile Ala Ala Asn Lys Leu Ser His Leu Tyr Arg
245 250 255

Tyr Leu Phe Tyr Val Ala Val Gly Leu Ile Val Ile Leu Leu Trp Ile
260 265 270

Ile Arg Arg Leu Arg Lys Lys Lys Lys Gln Pro Glu Lys Ala Leu Lys
275 280 285

Ala Leu Lys Ala Ala Arg Lys Glu Val Lys Val Glu Asp Gly Gln Gln
290 295 300

<210> SEQ ID NO 27
<211> LENGTH: 915
<212> TYPE: DNA
<213> ORGANISM: Streptococcus pneumoniae

<400> SEQUENCE: 27
atgctgataa aaatggtaaa aacaaaaaag caaaaacgaa ataatctcct attaggagtg 60
gtatttttca ttggaatggc ggtaatggcg tatccgctgg tgtctcgctt gtattatcga 120

```
gtggaatcaa atcaacaaat tgctgacttt gataaggaaa aagcaacgtt ggatgaggct    180

gacattgatg aacgaatgaa attggcacaa gccttcaatg actctttgaa taatgtagtg    240

agtggcgatc cttggtcgga agaaatgaag aaaaaagggc gagcagagta tgcacgtatg    300

ttagaaatcc atgagcggat ggggcatgtg gaaatccccg ttattgacgt ggatttgccg    360

gtttatgctg gtactgctga agaggtattg cagcaagggg ctgggcatct agagggaact    420

tctctgccga tcggaggcaa ttcgacccat gcggtgatta cggcacatac aggtttgcca    480

acagctaaga tgtttacgga tttgaccaaa cttaaagttg ggataagtt ttatgtgcac    540

aatatcaagg aagtgatggc ctatcaagtg gatcaagtaa aggtgattga gccgacgaac    600

tttgatgatt tattgattgt accaggtcat gattatgtga ccttgctgac ttgtacgcca    660

tacatgatca atacccatcg tctattggtt cgggggcatc ggataccgta cgtagcagag    720

gttgaggaag aatttattgc agcaaacaaa ctcagtcatc tctatcgcta cctgttttat    780

gtggcagttg gtttgattgt gattctttta tggattattc gacgcttgcg caagaagaaa    840

aaacaaccgg aaaaggcttt gaaggcgctg aaagcagcaa ggaaggaagt gaaggtggag    900

gatggacaac agtag                                                     915
```

<210> SEQ ID NO 28
<211> LENGTH: 2199
<212> TYPE: DNA
<213> ORGANISM: Enterococcus faecalis

<400> SEQUENCE: 28

```
actaaaattc gtttacttta tgcatttaaa tgaaaaagca gatcctacga aaggctttaa     60

aaatgaggcg aatgttgata acggtcatac cgacgaccaa acaccaccaa ctgttgaagt    120

tgtgacaggt gggaaacgtt tcattaaagt cgatggcgat gtgacagcga cacaagcctt    180

ggcgggagct tcctttgtcg tccgtgatca aaacagcgac acagcaaatt atttgaaaat    240

cgatgaaaca acgaaagcag caacttgggt gaaaacaaaa gctgaagcaa ctacttttac    300

aacaacggct gatggattag ttgatatcac agggcttaaa tacggtacct attatttaga    360

agaaactgta gctcctgatg attatgtctt gttaacaaat cggattgaat ttgtggtcaa    420

tgaacaatca tatggcacaa cagaaaacct agtttcacca gaaaaagtac caaacaaaca    480

caaaggtacc ttaccttcaa caggtggcaa aggaatctac gtttacttag gaagtggcgc    540

agtcttgcta cttattgcag gagtctactt tgctagacgt agaaaagaaa atgcttaatt    600

tctagcatca ccgaagaaat ttttagaaaa acaaagagcc tgggccaatc actgtcccag    660

gctctcatgc tttattttta aggaggaagc aatgaagtca aaaaagaaac gtcgtatcat    720

tgatggtttt atgattcttt tactgattat tggaataggt gcatttgcgt atcctttttgt    780

tagcgatgca ttaaataact atctggatca acaaattatc gctcattatc aagcaaaagc    840

aagccaagaa aacaccaaag aaatggctga acttcaagaa aaaatggaaa agaaaaacca    900

agaattagcg aaaaaaggca gcaatcctgg attagatcct ttttctgaaa cgcaaaaaac    960

aacgaaaaaa ccagacaaat cctattttga aagtcatacg attggtgttt taaccattcc   1020

aaaaataaat gtccgtttac caatttttga taaaacgaat gcattgctat tggaaaaagg   1080

aagctccttg ttagaaggaa cctcctatcc tacaggtggt acgaatacac atgcggtcat   1140

ttcaggccat cgtggtctcc ctcaagccaa attatttaca gatttgccag aattaaaaaa   1200

aggcgatgaa ttttatatcg aagtcaatgg gaagacgctt gcttatcaag tagatcaaat   1260

aaaaaccgtt gaaccaactg atacaaaaga tttacacatt gagtctggcc aagatctcgt   1320
```

```
cactttatta acttgcacac cgtatatgat aaacagtcat cggttattag ttcgaggaca   1380

tcgtatccca tatcaaccag aaaaagcagc agcggggatg aaaaaagtgg cacaacaaca   1440

aaatttacta ttatggacat tacttttaat tgcctgtgcg ttaattatta gcggcttcat   1500

tatctggtac aagcgacgga aaaagacgac cagaaaacca aagtagtatg acgaaaaggc   1560

taaacatact aaaaaaaaga gtaaaaaaat agcttttcaa tttttaatcc tccttatcgt   1620

gcataattga accagagaaa cagaagtatt aacgaaataa ctaaaagagc aagccctgaa   1680

taaaaagcga caaagggcca atcaatcgac tgtttaaatt cctgccaagt ttggattttt   1740

ctgttttttt tcgcgctatc ctcaagcgtg agtaaataat tcaatagtaa gaggagtagc   1800

aacaccgtga aatcatttgt ggtaaaaagc acatgtaaaa atagaatgac aaagacaaca   1860

cgggataaca ctcgattccg caaaattaaa aataacttag cacgcataat aaaccaccat   1920

ttcttatcag agataatgaa tctgtttttg tctactcttt agttatatca taaaattctt   1980

aataatgaaa aaatgactcg agaaaataat tgaaaaaagt ttttttcct gaatcattat   2040

tttcgtaaat aaagaataaa cgtgttactc ttggcttatc aaatttggaa ggagtgttaa   2100

aaatgaaata tctggatatt attgctttaa ttttattgat tgtcggaggt ttaaactggt   2160

tattagttgg tgcatttaat tttgatttag ttgcaacaa                          2199
```

<210> SEQ ID NO 29
<211> LENGTH: 284
<212> TYPE: PRT
<213> ORGANISM: Enterococcus faecalis

<400> SEQUENCE: 29

```
Met Lys Ser Lys Lys Lys Arg Arg Ile Ile Asp Gly Phe Met Ile Leu
1               5                   10                  15

Leu Leu Ile Ile Gly Ile Gly Ala Phe Ala Tyr Pro Phe Val Ser Asp
            20                  25                  30

Ala Leu Asn Asn Tyr Leu Asp Gln Gln Ile Ile Ala His Tyr Gln Ala
        35                  40                  45

Lys Ala Ser Gln Glu Asn Thr Lys Glu Met Ala Glu Leu Gln Glu Lys
    50                  55                  60

Met Glu Lys Lys Asn Gln Glu Leu Ala Lys Lys Gly Ser Asn Pro Gly
65                  70                  75                  80

Leu Asp Pro Phe Ser Glu Thr Gln Lys Thr Thr Lys Lys Pro Asp Lys
                85                  90                  95

Ser Tyr Phe Glu Ser His Thr Ile Gly Val Leu Thr Ile Pro Lys Ile
            100                 105                 110

Asn Val Arg Leu Pro Ile Phe Asp Lys Thr Asn Ala Leu Leu Leu Glu
        115                 120                 125

Lys Gly Ser Ser Leu Leu Glu Gly Thr Ser Tyr Pro Thr Gly Gly Thr
    130                 135                 140

Asn Thr His Ala Val Ile Ser Gly His Arg Gly Leu Pro Gln Ala Lys
145                 150                 155                 160

Leu Phe Thr Asp Leu Pro Glu Leu Lys Lys Gly Asp Glu Phe Tyr Ile
                165                 170                 175

Glu Val Asn Gly Lys Thr Leu Ala Tyr Gln Val Asp Gln Ile Lys Thr
            180                 185                 190

Val Glu Pro Thr Asp Thr Lys Asp Leu His Ile Glu Ser Gly Gln Asp
        195                 200                 205

Leu Val Thr Leu Leu Thr Cys Thr Pro Tyr Met Ile Asn Ser His Arg
    210                 215                 220
```

```
Leu Leu Val Arg Gly His Arg Ile Pro Tyr Gln Pro Glu Lys Ala Ala
225                 230                 235                 240

Ala Gly Met Lys Lys Val Ala Gln Gln Gln Asn Leu Leu Leu Trp Thr
                245                 250                 255

Leu Leu Leu Ile Ala Cys Ala Leu Ile Ile Ser Gly Phe Ile Ile Trp
            260                 265                 270

Tyr Lys Arg Arg Lys Lys Thr Thr Arg Lys Pro Lys
        275                 280


<210> SEQ ID NO 30
<211> LENGTH: 855
<212> TYPE: DNA
<213> ORGANISM: Enterococcus faecalis

<400> SEQUENCE: 30

atgaagtcaa aaaagaaacg tcgtatcatt gatggtttta tgattctttt actgattatt      60

ggaataggtg catttgcgta tccttttgtt agcgatgcat taaataacta tctggatcaa     120

caaattatcg ctcattatca agcaaaagca agccaagaaa acaccaaaga aatggctgaa     180

cttcaagaaa aaatggaaaa gaaaaaccaa gaattagcga aaaaaggcag caatcctgga     240

ttagatcctt tttctgaaac gcaaaaaaca acgaaaaaac cagacaaatc ctattttgaa     300

agtcatacga ttggtgtttt aaccattcca aaaataaatg tccgtttacc aatttttgat     360

aaaacgaatg cattgctatt ggaaaaagga agctccttgt tagaaggaac ctcctatcct     420

acaggtggta cgaatacaca tgcggtcatt tcaggccatc gtggtctccc tcaagccaaa     480

ttatttacag atttgccaga attaaaaaaa ggcgatgaat tttatatcga agtcaatggg     540

aagacgcttg cttatcaagt agatcaaata aaaaccgttg aaccaactga tacaaaagat     600

ttacacattg agtctggcca agatctcgtc actttattaa cttgcacacc gtatatgata     660

aacagtcatc ggttattagt tcgaggacat cgtatcccat atcaaccaga aaaagcagca     720

gcggggatga aaaaagtggc acaacaacaa aatttactat tatggacatt acttttaatt     780

gcctgtgcgt taattattag cggcttcatt atctggtaca agcgacggaa aaagacgacc     840

agaaaaccaa agtag                                                      855


<210> SEQ ID NO 31
<211> LENGTH: 2687
<212> TYPE: DNA
<213> ORGANISM: Corynebacterium diphtheriae

<400> SEQUENCE: 31

gtggtccgga gtatgacaag aacgctccgg ttcaggtaaa cggcactggt aacggtaacg      60

atctcgtggt cacctctgac aagaacggca acgtccactt cgagggcctg ttcgtctccg     120

acgaccagaa tgatccggga aagtcagctg cgcagcgctg ctacgtcctc gtcgagaccg     180

aggccccgac gggcttcgtt actccgaaag atgggacggt cttcccagtt gctgtaaaga     240

ttggacagac tgctaccact acctacgacg caaaggtcga gaacgtcaag cgcgataccc     300

ctgacctgcc gctgaccggt ggcaagggtg tgctgttcct gatgattgcc ggtggtctgt     360

tgctgctggt tgctgttggt gctggtttcg tctttgtacg ccgtatcaac gagtaattga     420

tttgtcgcgt gattaaataa tcgcgttgcg ccgcccaatg cagggcatca aatgccccgc     480

cggcgggcat aaacgccggc ggggtgcggt ggctttccac cgcacccccca cattctttgt     540

cagagatttg ctgtttggcc tgtgccaccc ggcatccccc tatatgagaa acggacgtac     600

ctgtcatggt taccaccgcg tcaccgcgct ctaccggacc ggataaccca gacgcgcaac     660
```

-continued

```
caaagcgtcg ttgggtcttt tccggactcg cattgtttgc gtgtataacg gcgctagccg    720
gcctcatgtt ggggttgtat ccatctactg cagcgtggtt taacgcccgc gaacaggcca    780
aactggtaga tctctatgat tccaaaattg aaaatgcaac ccctcttagc gcggaacaat    840
tacttgaact cgcgcaccgt tataacgacc gcctgaccgt aggcgctgct ctcgatccct    900
gggctaacgt cccccgcgga gcgggcaaag aagacggcga cggtatggcc tataaagacc    960
agttgcgtgt tgaccgtacg gatgtcatgg ctcgtatacg tatcccctct atcaaggtgg   1020
atctaccgat ctatcacggc acgagcgata acactctaaa gaagggcgct ggccatttgg   1080
aaggtacctc gttaccggtg ggaggaccac gcacccattc cgttatcact gcacaccgtg   1140
gcttagctga ggccaccatg ttcactaatc tcaacaaggt tggggtaggg gatagattca   1200
ccattgaggt gatgggcgaa gtccttacgt atgaagtgcg tgaaactcgt gtggtcagcc   1260
cagaggacac taggttcctg caaactcaag acgatcgtga ccttgtcaca ctcgttactt   1320
gtactccgtt gggcatcaat acacatcgca ttctggtgac agctgagcgc attactccca   1380
ccccgcaatc cgatatcgat gcagcacgtc aagcttccca aatcggcttc ccttggtggg   1440
cggtcatttt cgcagtggga tttagcttta tcgccttgtt cttctggcgt tcgggttaca   1500
tgattcctcc aaagaagaag gaagaagaca tcgaaagcga agctgatggc gatgaactct   1560
gaaacggcgg ggaaggaacc caacgtggtc agtaccgacg ctaaacactc caccggtacc   1620
agttccaatg cgggtaccgg tgagagctca gcgaaaaaga aagcgcagac ggcaattgct   1680
gcgatagtca tgcttttgtg cggactgtta gggctggtga ttctgttcta tccagtcgtg   1740
tccactcaac ttaacaatta tgaacagtct aaactcgccc gacagtttgg tgcagacgct   1800
gcccaagctg accctgccgt agttgctgct gctcttgatg ctgcccatgc ctacaacgat   1860
tcgctagaaa atggacccct gcaggatccg tggaccggtg gagatagcac taaggatcct   1920
gcctatcagg catacgagaa actcttaggg gaatatccgg cgatggctca gatctctatc   1980
ccggctattt ccgtgaacct tcccatttac cacgggacaa gcgacgccac actcctcaaa   2040
ggtgttgggc acctttacgg tactgcgcta cccgttggtg gactggggac gcgttcggtt   2100
ctaacagcgc attcaggtat ccaaaaatcg accttctttg acaatttaga aaaggtcaaa   2160
aagggtgacg ccatttatgt acgcaatatt ggtgagaccc tgaaatacca agtacgcgac   2220
atcgaaatca tccgtccagc ggagattgac cgtatccagc caatcccaga ccgagactta   2280
attaccctcg tgacctgtac accctatgga atcaataccc ataggctttt ggttactgcc   2340
gaacgtgtcc ctatggaacc cggtgaggcg gaccgtgcat ttgccggtga cggaattgtc   2400
tggcagtggt ggatgaagct agctatcggt gtgttggtgg tcatccttct cctaactggg   2460
tggctcatta tccgtatttt gcgagctagg aaattcgcga agaaaacagc tggagcagac   2520
gctgctaaat ctgttgaacc tggtgatatt gaggcgtcgc taagcgcttc agcggccgag   2580
gagtcccagt aatatgcaga aaccaatttc cccaacacat gcaaacaccc aagcagtcgc   2640
ccattcctga aaggacgccc tactatgaag aagactcact tgttccg                 2687
```

<210> SEQ ID NO 32
<211> LENGTH: 348
<212> TYPE: PRT
<213> ORGANISM: Corynebacterium diphtheriae

<400> SEQUENCE: 32

```
Met Ala Met Asn Ser Glu Thr Ala Gly Lys Glu Pro Asn Val Val Ser
1               5                   10                  15
```

-continued

```
Thr Asp Ala Lys His Ser Thr Gly Thr Ser Ser Asn Ala Gly Thr Gly
            20                  25                  30

Glu Ser Ser Ala Lys Lys Lys Ala Gln Thr Ala Ile Ala Ala Ile Val
        35                  40                  45

Met Leu Leu Cys Gly Leu Leu Gly Leu Val Ile Leu Phe Tyr Pro Val
    50                  55                  60

Val Ser Thr Gln Leu Asn Asn Tyr Glu Gln Ser Lys Leu Ala Arg Gln
65                  70                  75                  80

Phe Gly Ala Asp Ala Ala Gln Ala Asp Pro Ala Val Val Ala Ala Ala
                85                  90                  95

Leu Asp Ala Ala His Ala Tyr Asn Asp Ser Leu Glu Asn Gly Pro Leu
            100                 105                 110

Gln Asp Pro Trp Thr Gly Gly Asp Ser Thr Lys Asp Pro Ala Tyr Gln
        115                 120                 125

Ala Tyr Glu Lys Leu Leu Gly Glu Tyr Pro Ala Met Ala Gln Ile Ser
    130                 135                 140

Ile Pro Ala Ile Ser Val Asn Leu Pro Ile Tyr His Gly Thr Ser Asp
145                 150                 155                 160

Ala Thr Leu Leu Lys Gly Val Gly His Leu Tyr Gly Thr Ala Leu Pro
                165                 170                 175

Val Gly Gly Leu Gly Thr Arg Ser Val Leu Thr Ala His Ser Gly Ile
            180                 185                 190

Gln Lys Ser Thr Phe Phe Asp Asn Leu Glu Lys Val Lys Lys Gly Asp
        195                 200                 205

Ala Ile Tyr Val Arg Asn Ile Gly Glu Thr Leu Lys Tyr Gln Val Arg
    210                 215                 220

Asp Ile Glu Ile Ile Arg Pro Ala Glu Ile Asp Arg Ile Gln Pro Ile
225                 230                 235                 240

Pro Asp Arg Asp Leu Ile Thr Leu Val Thr Cys Thr Pro Tyr Gly Ile
                245                 250                 255

Asn Thr His Arg Leu Leu Val Thr Ala Glu Arg Val Pro Met Glu Pro
            260                 265                 270

Gly Glu Ala Asp Arg Ala Phe Ala Gly Asp Gly Ile Val Trp Gln Trp
        275                 280                 285

Trp Met Lys Leu Ala Ile Gly Val Leu Val Val Ile Leu Leu Leu Thr
    290                 295                 300

Gly Trp Leu Ile Ile Arg Ile Leu Arg Ala Arg Lys Phe Ala Lys Lys
305                 310                 315                 320

Thr Ala Gly Ala Asp Ala Ala Lys Ser Val Glu Pro Gly Asp Ile Glu
                325                 330                 335

Ala Ser Leu Ser Ala Ser Ala Ala Glu Glu Ser Gln
            340                 345
```

<210> SEQ ID NO 33
<211> LENGTH: 1047
<212> TYPE: DNA
<213> ORGANISM: Corynebacterium diphtheriae

<400> SEQUENCE: 33

```
atggcgatga actctgaaac ggcggggaag gaacccaacg tggtcagtac cgacgctaaa      60

cactccaccg gtaccagttc caatgcgggt accggtgaga gctcagcgaa aaagaaagcg     120

cagacggcaa ttgctgcgat agtcatgctt ttgtgcggac tgttagggct ggtgattctg     180

ttctatccag tcgtgtccac tcaacttaac aattatgaac agtctaaact cgcccgacag     240

tttggtgcag acgctgccca agctgaccct gccgtagttg ctgctgctct tgatgctgcc     300
```

```
catgcctaca acgattcgct agaaaatgga cccctgcagg atccgtggac cggtggagat    360

agcactaagg atcctgccta tcaggcatac gagaaactct taggggaata tccggcgatg    420

gctcagatct ctatcccggc tatttccgtg aaccttccca tttaccacgg gacaagcgac    480

gccacactcc tcaaaggtgt tgggcacctt tacggtactg cgctacccgt tggtggactg    540

gggacgcgtt cggttctaac agcgcattca ggtatccaaa aatcgacctt ctttgacaat    600

ttagaaaagg tcaaaaaggg tgacgccatt tatgtacgca atattggtga gaccctgaaa    660

taccaagtac gcgacatcga aatcatccgt ccagcggaga ttgaccgtat ccagccaatc    720

ccagaccgag acttaattac cctcgtgacc tgtacaccct atggaatcaa tacccatagg    780

cttttggtta ctgccgaacg tgtccctatg gaacccggtg aggcggaccg tgcatttgcc    840

ggtgacggaa ttgtctggca gtggtggatg aagctagcta tcggtgtgtt ggtggtcatc    900

cttctcctaa ctgggtggct cattatccgt attttgcgag ctaggaaatt cgcgaagaaa    960

acagctggag cagacgctgc taaatctgtt gaacctggtg atattgaggc gtcgctaagc   1020

gcttcagcgg ccgaggagtc ccagtaa                                       1047
```

<210> SEQ ID NO 34
<211> LENGTH: 19
<212> TYPE: PRT
<213> ORGANISM: Artificial sequence
<220> FEATURE:
<223> OTHER INFORMATION: consensus/Streptococcus pyogenes
<220> FEATURE:
<221> NAME/KEY: MISC_FEATURE
<222> LOCATION: (12)..(12)
<223> OTHER INFORMATION: x=S or T
<220> FEATURE:
<221> NAME/KEY: MISC_FEATURE
<222> LOCATION: (18)..(18)
<223> OTHER INFORMATION: x=R or K

<400> SEQUENCE: 34

```
Thr Leu Leu Thr Cys Thr Pro Tyr Met Ile Asn Xaa His Arg Leu Leu
1               5                   10                  15

Val Xaa Gly
```

<210> SEQ ID NO 35
<211> LENGTH: 19
<212> TYPE: PRT
<213> ORGANISM: Corynebacterium diphtheriae

<400> SEQUENCE: 35

```
Thr Leu Val Thr Cys Thr Pro Tyr Gly Ile Asn Thr His Arg Leu Leu
1               5                   10                  15

Val Thr Ala
```

<210> SEQ ID NO 36
<211> LENGTH: 19
<212> TYPE: PRT
<213> ORGANISM: Streptococcus pyogenes

<400> SEQUENCE: 36

```
Thr Leu Val Thr Cys Thr Pro Tyr Gly Val Asn Thr Lys Arg Leu Leu
1               5                   10                  15

Val Arg Gly
```

<210> SEQ ID NO 37
<211> LENGTH: 150
<212> TYPE: PRT

-continued

```
<213> ORGANISM: Streptococcus pyogenes

<400> SEQUENCE: 37

Ile Glu Asn Asn Asp Ile Met Gly Tyr Val Glu Val Pro Ser Ile Lys
1               5                   10                  15

Val Thr Leu Pro Ile Tyr His Tyr Thr Thr Asp Glu Val Leu Thr Lys
            20                  25                  30

Gly Ala Gly His Leu Phe Gly Ser Ala Leu Pro Val Gly Gly Asp Gly
        35                  40                  45

Thr His Thr Val Ile Ser Ala His Arg Gly Leu Pro Ser Ala Glu Met
    50                  55                  60

Phe Thr Asn Leu Asn Leu Val Lys Lys Gly Asp Thr Phe Tyr Phe Arg
65                  70                  75                  80

Val Leu Asn Lys Val Leu Ala Tyr Lys Val Asp Gln Ile Leu Thr Val
                85                  90                  95

Glu Pro Asp Gln Val Thr Ser Leu Ser Gly Val Met Gly Lys Asp Tyr
            100                 105                 110

Ala Thr Leu Val Thr Cys Thr Pro Tyr Gly Val Asn Thr Lys Arg Leu
        115                 120                 125

Leu Val Arg Gly His Arg Ile Ala Tyr His Tyr Lys Lys Tyr Gln Gln
    130                 135                 140

Ala Lys Lys Ala Met Lys
145                 150
```